US010292933B2

(12) United States Patent
Machluf et al.

(10) Patent No.: US 10,292,933 B2
(45) Date of Patent: *May 21, 2019

(54) LIPOSOMAL COMPOSITIONS AND USES OF SAME

(71) Applicant: Technion Research & Development Foundation Limited, Haifa (IL)

(72) Inventors: Marcelle Machluf, Haifa (IL); Tomer Bronshtein, Zikhron-Yaakov (IL)

(73) Assignee: Technion Research & Development Foundation Limited, Haifa (IL)

( * ) Notice: Subject to any disclaimer, the term of this patent is extended or adjusted under 35 U.S.C. 154(b) by 0 days.

This patent is subject to a terminal disclaimer.

(21) Appl. No.: 15/498,526

(22) Filed: Apr. 27, 2017

(65) Prior Publication Data

US 2017/0224618 A1 Aug. 10, 2017

Related U.S. Application Data

(63) Continuation of application No. 13/392,575, filed as application No. PCT/IL2010/000703 on Aug. 26, 2010, now Pat. No. 9,642,817.

(60) Provisional application No. 61/237,306, filed on Aug. 27, 2009.

(51) Int. Cl.
*A61K 9/127* (2006.01)
*A61K 9/51* (2006.01)
*C12N 15/88* (2006.01)
*A61K 47/69* (2017.01)
*A61K 47/48* (2006.01)

(52) U.S. Cl.
CPC .......... *A61K 9/1271* (2013.01); *A61K 9/1277* (2013.01); *A61K 9/5176* (2013.01); *A61K 47/48776* (2013.01); *A61K 47/48815* (2013.01); *A61K 47/6901* (2017.08); *A61K 47/6911* (2017.08); *C12N 15/88* (2013.01)

(58) Field of Classification Search
None
See application file for complete search history.

(56) References Cited

U.S. PATENT DOCUMENTS

| 6,120,797 A | 9/2000 | Meers et al. |
| 2011/0003008 A1 | 1/2011 | Lim |
| 2012/0164214 A1 | 6/2012 | Machluf et al. |

FOREIGN PATENT DOCUMENTS

WO  WO 2011/024172  3/2011

OTHER PUBLICATIONS

Examiniation Report Under Sections 12 & 13 of the Patents Act, 1970 and the Patents Rules, 2003 dated Oct. 17, 2017 From the Government of India, Intellectual Property India, Patents, Designs, Trade Marks, Geographical Indications Re. Application No. 484/MUMNP/2012. (6 Pages).
Communication Pursuant to Article 94(3) EPC dated Aug. 1, 2014 From the European Patent Office Re. Application No. 10761069.3.
International Preliminary Report on Patentability dated Mar. 8, 2012 From the International Bureau of WIPO Re. Application No. PCT/IL2010/000703.
International Search Report and the Written Opinion dated Apr. 5, 2011 From the International Searching Authority Re. Application No. PCT/IL2010/000703.
Notice of Amendment dated Nov. 15, 2016 From the State Intellectual Property Office of the People's Republic of China Re. Application No. 201610416895.6 and Its Summary Into English. (2 Pages).
Notice of Reexamination dated Aug. 7, 2015 From the Patent Reexamination Board of State Intellectual Property Office of the People's Republic of China Re. Application No. 201080048954.X and Its Translation Into English.
Notification of the Decision of Rejection dated Apr. 14, 2014 From the State Intellectual Property Office of the People's Republic of China Re. Application No. 201080048954.X and Its Translation Into English.
Official Action dated Aug. 12, 2016 From the US Patent and Trademark Office Re. U.S. Appl. No. 13/392,575.
Official Action dated Jan. 15, 2016 From the US Patent and Trademark Office Re. U.S. Appl. No. 13/392,575.
Reexamination Decision (Decision No. 106615) dated Mar. 15, 2016 From the Patent Reexamination Board of the State Intellectual Property Office of the People's Republic of China Re. Application No. 201080048954.X and Its Translation Into English.
Restriction Official Action dated Jul. 16, 2015 From the US Patent and Trademark Office Re. U.S. Appl. No. 13/392,575.
Summons to Attend Oral Proceedings Pursuant to Rule 115(1) EPC dated Jun. 17, 2016 From the European Patent Office Re. Application No. 10761069.3.
Translation of Notification of Office Action dated Dec. 21, 2012 From the State Intellectual Property Office of the People's Republic of China Re. Application No. 201080048954.X.
Translation of Notification of Office Action dated Aug. 22, 2013 From the State Intellectual Property Office of the People's Republic of China Re. Application No. 201080048954.X.
Translation of Search Report dated Dec. 21, 2012 From the State Intellectual Property Office of the People's Republic of China Re. Application No. 201080048954.X.
Translation of Search Report dated Aug. 22, 2013 From the State Intellectual Property Office of the People's Republic of China Re. Application No. 201080048954.X.
Boone et al. "Isolation of Plasma Membrane Fragments From HeLa Cells", The Journal of Cell Biology, 41: 378-392, May 1, 1969.
Estelles et al. "Exosome Nanovesicles Displaying G Protein-Coupled Receptors for Drug Discovery", International Journal of Nanomedicine, 2(4): 751-760, Published Online Dec. 2007.
Fadeel et al. "The Ins and Outs of Phospholipid Asymmetry in the Plasma Membrane: Roles in Health and Disease", Critical Reviews in Biochemistry and Molecular Biology, 44(5): 264-277, 2009.
Immordino et al. "Stealth Liposomes: Review of the Basic Science, Rationale, and Clinical Applications, Existing and Potential", International Journal of Nanomedicine, XP009145524, 1(3): 297-315, Jan. 1, 2006. p. 302-305.

(Continued)

*Primary Examiner* — Robert M Kelly

(57) ABSTRACT

Compositions comprising liposomes composed of whole cell membrane fraction are provided. The liposomes may be attached to, or encapsulate a pharmaceutical agent. Also provided are methods of generating and using these liposomes.

16 Claims, 10 Drawing Sheets
(3 of 10 Drawing Sheet(s) Filed in Color)

(56) References Cited

OTHER PUBLICATIONS

Kang et al. "Proteomic Analysis of Exosomes from Human Neural Stem Cells by Flow Field-Flow Fractionation and Nanoflow Liquid Chromatography-Tandem Mass Spectrometry", Journal of Proteome Research, 7(8): 3475-3480, Published Online Jun. 21, 2008.

Tan et al. "Therapeutic MSC Exosomes Are Derived from Lipid Raft Microdomains in the Plasma Membrane", Journal of Extracellular Vesicles, 2: P., 1-10, 2013.

Westerman et al. "Induction of Tumor-Specific Immunity in Mice by Immunization With Reconstituted Tumor Membrane Liposomes Containing Recombinant B7-2 (CD86)", Journal of Immunotherapy, 23(4): 456-463, 2000.

Westerman et al. "Liposomes Composed of Reconstituted Membranes for Induction of Tumor-Specific Immunity", Methods in Enzymology, XP009145463, 373: 118-127, Jan. 1, 2003. p. 118, 121.

Zhang et al. "Advance of Study on Mesenchymal Stem Cell Homing", Journal of Experimental Hematology, 15(6): 1345-1348, Dec. 31, 2007.

Notification of Office Action and Search Report dated Jan. 14, 2019 From the State Intellectual Property Office of the People's Republic of China Re. Application No. 201610416895.6. (9 Pages).

Translation dated Mar. 10, 2019 of Notification of Office Action and Search Report dated Jan. 14, 2019 From the State Intellectual Property Office of the People's Republic of China Re. Application No. 20160416895.6. (14 Pages).

Gaudreault et al. "Erythrocyte Membrane-Bound Daunorubicin as a Delivery System in Anticancer Treatment", Anticancer Research, 9(4): 1201-1205, Jul.-Aug. 1989.

Lejeune et al. "Nanoerythrosome, A New Derivative of Reythrocyte Ghost: Preparation and Antineoplastic Potential as Drug Carrier for Daunorubicin", Anticancer Research, 14(3A): 915-920, May-Jun. 1994.

Shi et al. "Membrane Loaded Liposomes Enhance the Immunity of the Immunocytes In Vitro", Science Technology and Engineering, 9(12): 3217-3221, Jun. 15, 2009. English Abstract.

Xin et al. "Targeted Delivery of CX3CL1 to Multiple Lung Tumors by Mesenchymal Stem Cells", Stem Cells, 25(7): 1618-1626, Published Online Apr. 5, 2007.

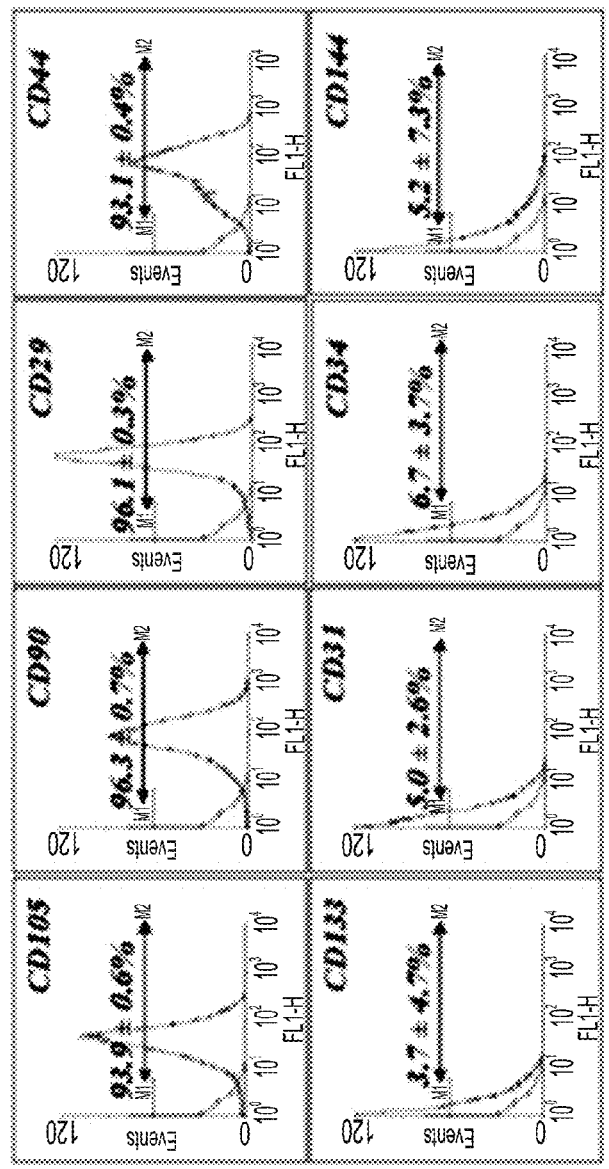
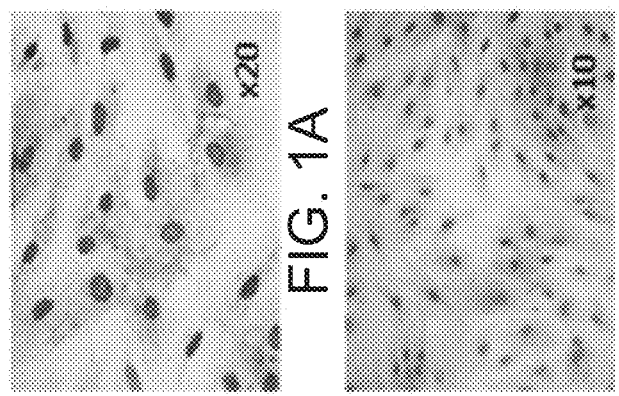
FIG. 1C
FIG. 1A
FIG. 1B

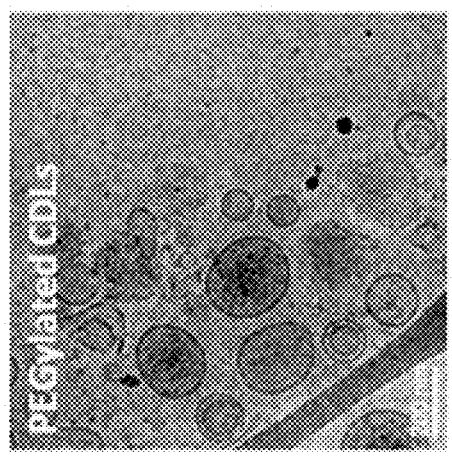
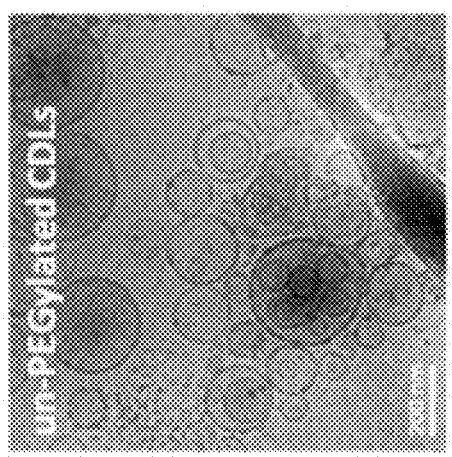
FIG. 4A  FIG. 4B
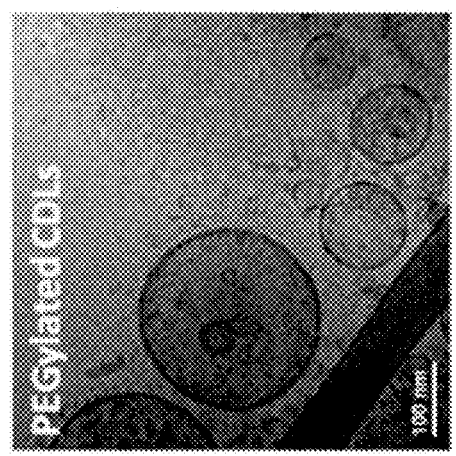
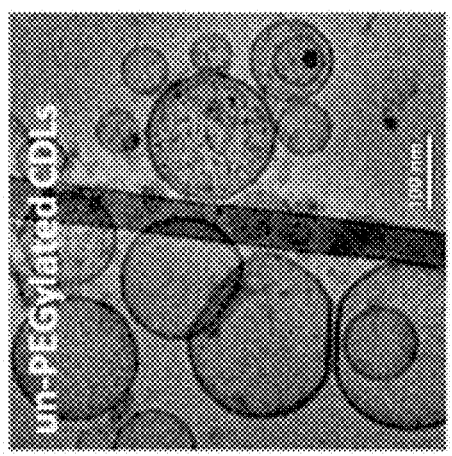

LIPOSOMAL COMPOSITIONS AND USES OF SAME

RELATED APPLICATIONS

This application is a continuation of U.S. patent application Ser. No. 13/392,575 filed on Feb. 27, 2012 now U.S. Pat. No. 9,642,817, which is a National Phase of PCT Patent Application No. PCT/IL2010/000703 having International Filing Date of Aug. 26, 2010, which claims the benefit of priority under 35 USC 119(e) of U.S. Provisional Patent Application No. 61/237,306 filed Aug. 27, 2009, the contents of which are incorporated herein by reference in their entirety.

FIELD AND BACKGROUND OF THE INVENTION

The present invention, in some embodiments thereof, relates to liposomal compositions and uses of same.

Liposome based DNA and drug delivery systems have been extensively investigated in the last four decades, and used as a mean to treat various conditions. Liposomal systems allow the efficient entrapment of both hydrophilic and hydrophobic compounds in a well-characterized, biocompatible and non-immunogenic lipid vesicle that can range from nanometers to micrometers in diameter. Liposomes can also be targeted using specific ligands such as protein conjugates or antibodies that bind specific cellular receptors. In cancer therapy, liposomal systems are of the most popular and well-investigated drug carriers. This is mainly due to the enhanced permeability and retention (EPR) effect, which refers to the increased vascular permeability of tumor vessels due to tumor angiogenesis. The EPR effect results in the accumulation of liposomes in the tumor extracellular fluid, which is exploited as a passive targeting mechanism. State of the art technologies in liposomal drug delivery for cancer therapy primarily include drugs that are approved for clinical use (e.g., DaunoXome™, Myocet™, Doxil™, Caelyx™). Several approaches are currently investigated for the targeting of liposomal systems to cancer, which include the binding of targeting moieties to the liposome surface (e.g., antibodies). Synthetic cationic liposomes are the most common vectors for DNA delivery although their cytotoxicity remains a concern irrespective of the preferred route of DNA transfer both in vitro and in vivo. On the other hand, anionic liposomes that better resemble cell-derived liposomes (in term of their electric charge) were also shown to mediate gene transfer, but suffer from poor encapsulation efficiency due to the large size and the negative charge of the uncondensed DNA. Improving encapsulation efficiency and protecting DNA from degradation was achieved by complexation of the DNA with cations or poly-cations that subsequently also significantly improved the transfection efficiencies.

In the last decade several studies have revealed that certain primary cells, such as adult mesenchymal stem cells (MSC), adult hematopoietic stem cells (HSC) and endothelial cells, accumulate at tumor microenvironments, when administered to tumor bearing animals. Recent data suggests that isolated membrane fractions of tumor cells appear to contain potent MSC attractants, more so than the cytoplasmic fractions isolated from the same cells. This data implies that the mechanism of MSC targeting to tumor cells is mainly governed by cell-to-cell interactions via the binding of surface molecules found on tumors and MSC. However, cellular response to different soluble factors (i.e., chemokines) secreted by angiogenic blood vessels and tumor cells is suggested to take some part in the MSC homing mechanism as well. The homing mechanism motivated studies on the use of these cells as a targeted delivery vehicle for cancer therapy. In these studies, primary cells were isolated and transduced with different genes of interest, either anti-cancer or reporter genes. The cells were transplanted to tumor bearing animals and their homing to the tumor microenvironment was demonstrated using the expressed reporter proteins. Tumor inhibition was achieved using the expressed anti-cancer proteins.

Liposomes, which are derived from the cytoplasmatic membrane of mammalian cells, have been commonly used as a tool in the study of membranes and cellular mechanisms. Cell derived liposomes (CDL or CDLs in plural) have been also investigated as a tool for cancer immunotherapy. In these studies, liposomes were prepared from the membranes of tumor cells and were used as adjuvant to evoke the immune system towards tumor antigens located on the liposome membrane. However, cell derived liposomes have never been produced from stem cells, nor used as a delivery vehicle. Furthermore, no CDL system has ever been developed as a targeting platform.

RELATED ART

Boone, C. W., Ford, L. E., Bond, H. E., Stuart, D. C. & Lorenz, D. Isolation of plasma membrane fragments from HeLa cells. J Cell Biol 41, 378-392 (1969).

Westerman and Jensen Methods Enzymol. 2003; 373:118-27.

SUMMARY OF THE INVENTION

According to an aspect of some embodiments of the present invention there is provided a composition-of matter comprising a liposome attached to, or encapsulating a pharmaceutical agent, the liposome being composed of a whole cell membrane fraction.

According to some embodiments of the invention, the cell is a human cell.

According to some embodiments of the invention, a cell source for the whole cell membrane is selected from the group consisting of a stem cell, a primary cell, a cell-line, a non-tumorigenic cell, a cancer cell and an immune cell.

According to an aspect of some embodiments of the present invention, there is provided a composition-of matter comprising a liposome composed of a whole cell membrane fraction of a stem cell.

According to some embodiments of the invention, the stem cell comprises a human mesenchymal stem cell.

According to an aspect of some embodiments of the present invention there is provided a composition-of matter comprising a liposome composed of a whole cell membrane fraction of a primary human cell.

According to an aspect of some embodiments of the present invention there is provided a composition-of matter comprising a liposome composed of a whole cell membrane fraction of a non-tumorigenic human cell.

According to some embodiments of the invention, the cell membrane is genetically modified to express an exogenous protein.

According to some embodiments of the invention, the exogenous protein is selected from the group consisting of a cell marker, a targeting moiety and the pharmaceutical agent.

According to some embodiments of the invention, the liposome encapsulates, or attached to a pharmaceutical agent.

According to some embodiments of the invention, the pharmaceutical agent is a therapeutic agent.

According to some embodiments of the invention, the composition-of-matter is non-immunogenic in a human subject.

According to some embodiments of the invention, a cell source of the whole cell membrane fraction comprises cells autologous to a host subject.

According to some embodiments of the invention, a cell source of the whole cell membrane fraction comprises cells non-autologous to a host subject.

According to some embodiments of the invention, said liposome is attached to a synthetic polymer at an external surface thereof.

According to some embodiments of the invention, the pharmaceutical agent is a diagnostic agent.

According to some embodiments of the invention, the liposome is unilamellar.

According to some embodiments of the invention, the liposome is attached to a synthetic polymer at an external surface thereof.

According to some embodiments of the invention, the synthetic polymer is a poly-ethylene-glycol (PEG).

According to some embodiments of the invention, the liposome has a size range of 30-1000 nm.

According to an aspect of some embodiments of the present invention there is provided a method of producing liposomes comprising,
(a) subjecting cells to hypotonic conditions, so as to obtain ruptured cell membranes and/or ghosts; and
(b) homogenizing the ruptured cell membranes and/or ghosts to thereby produce liposomes.

According to some embodiments of the invention, the homogenizing is effected by:
(c) sonicating the ruptured cell membrane and/or ghosts; and optionally
(d) extruding the ruptured membrane and/or ghosts through a matrix of pre-determined porosity.

According to some embodiments of the invention, the method further comprises conjugating a synthetic polymer to the liposomes following step (c).

According to an aspect of some embodiments of the present invention there is provided a method of encapsulating a pharmaceutical agent in a liposome, the method comprising making the liposomes according to the method above and adding the pharmaceutical agent prior to the step of homogenizing.

According to an aspect of some embodiments of the present invention there is provided a pharmaceutical composition comprising as an active ingredient the composition-of-matter and a pharmaceutically acceptable carrier.

According to an aspect of some embodiments of the present invention there is provided a method of delivering a pharmaceutical agent, the method comprising administering to a subject in need thereof the composition of matter, thereby delivering the pharmaceutical agent.

According to some embodiments of the invention, the cell source of the whole cell membrane fraction is autologous to the subject.

According to some embodiments of the invention, a cell source of the whole cell membrane fraction is non-autologous to said subject.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE SEVERAL VIEWS OF THE DRAWINGS

The patent or application file contains at least one drawing executed in color. Copies of this patent or patent application publication with color drawing(s) will be provided by the Office upon request and payment of the necessary fee.

Some embodiments of the invention are herein described, by way of example only, with reference to the accompanying images and drawings. [1-10 images, 11 drawing]. With specific reference now to the images/drawings in detail, it is stressed that the particulars shown are by way of example and for purposes of illustrative discussion of embodiments of the invention. In this regard, the description taken with the images/drawings makes apparent to those skilled in the art how embodiments of the invention may be practiced.

In the drawings:

FIGS. 1A-1C characterize human MSCs. Cell morphology as visualized by Giemsa staining (FIGS. 1A, 1B) and typical MSC (positive and negative) surface markers analyzed by flow cytometry (FIG. 1C).

Figure 2:
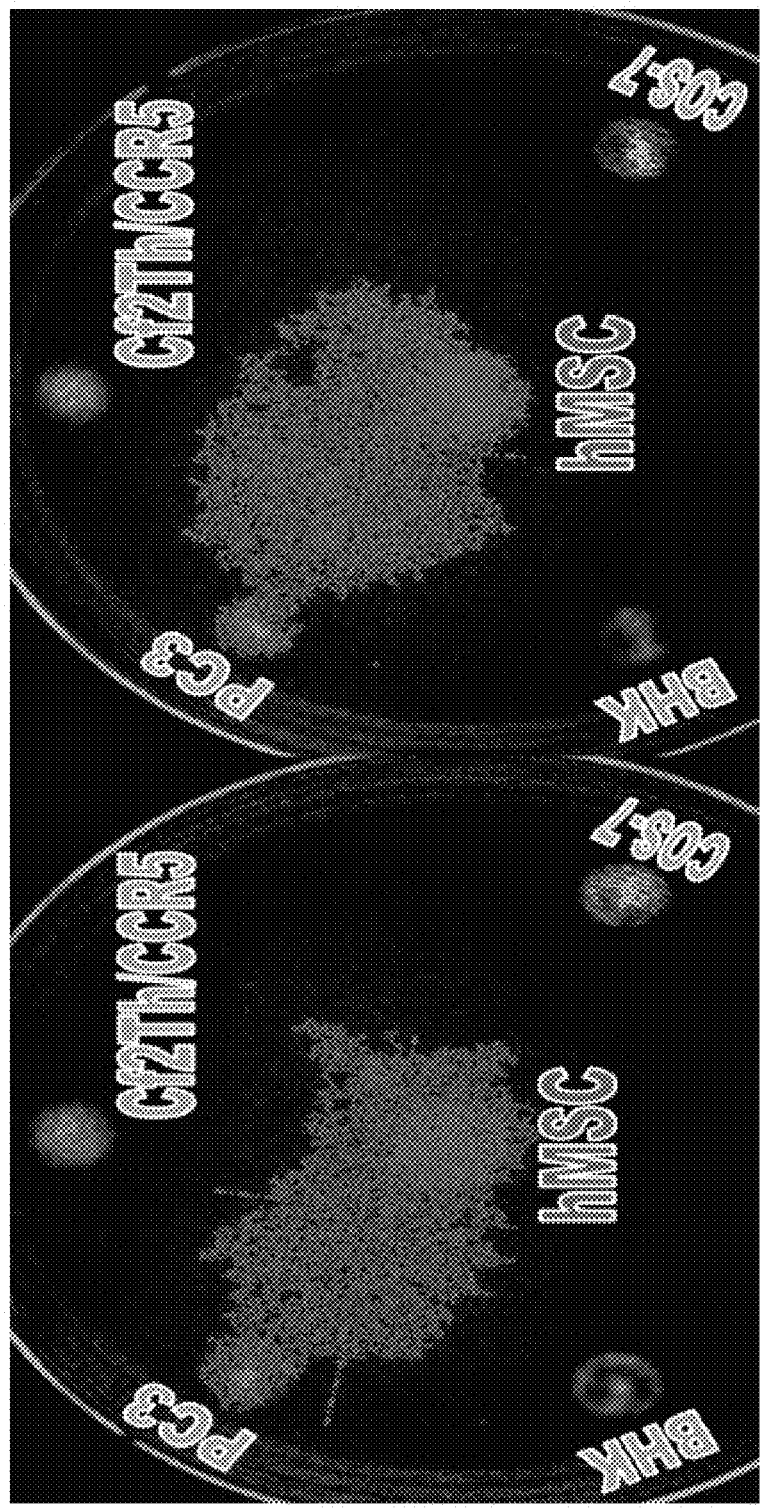

FIG. 2 is a photograph showing the migration of hMSCs towards cancer cells. DiI (red) labeled hMSC and DiO (green) labeled BHK, PC3, Cf2Th and COS-7 cells were drop-wise seeded. Maestro imaging following 72 hrs incubation demonstrated specific migration of the hMSCs towards PC3 prostate cells while "avoiding" other cell-lines.

Figure 3:
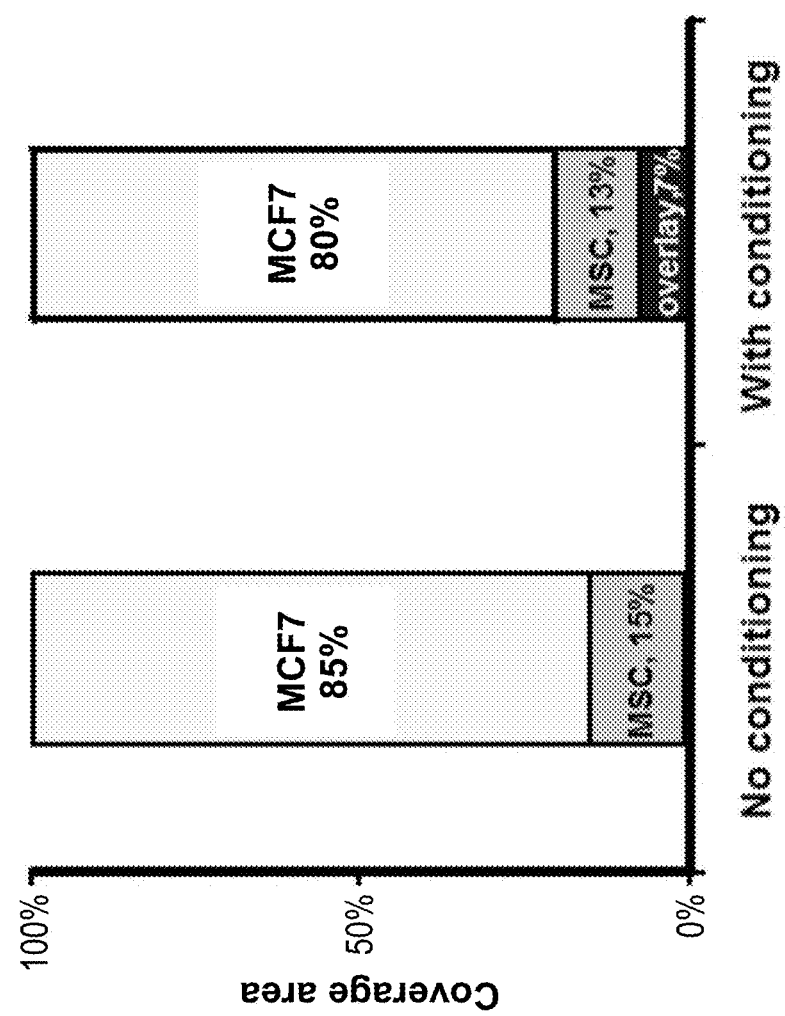

FIG. 3 is a graph showing targeting of MCF7 breast cancer cell-line by hMSCs stimulated by MCF7-derived condition media.

FIGS. 4A-4B are Cryo-TEM images of cell-derived liposomes. Cell-derived liposomes were prepared from the cytoplasmatic membranes of hMSCs and were PEGylated by conjugation with monomethoxy-PEG. The resulting PEGylated (FIG. 4A) and un-PEGylated (FIG. 4B) CDLs were then imaged by Cryo-TEM.

Figure 5A:
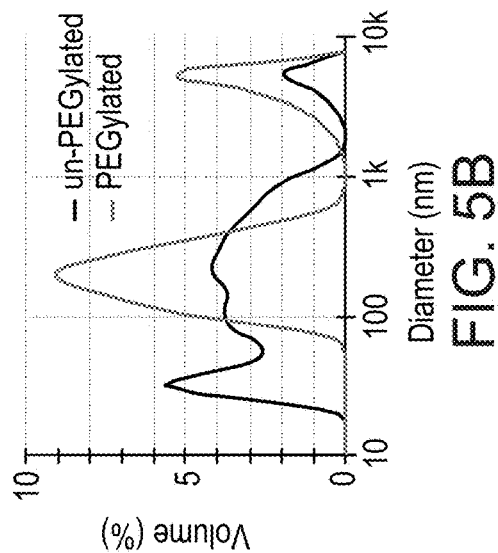
Figure 5B:
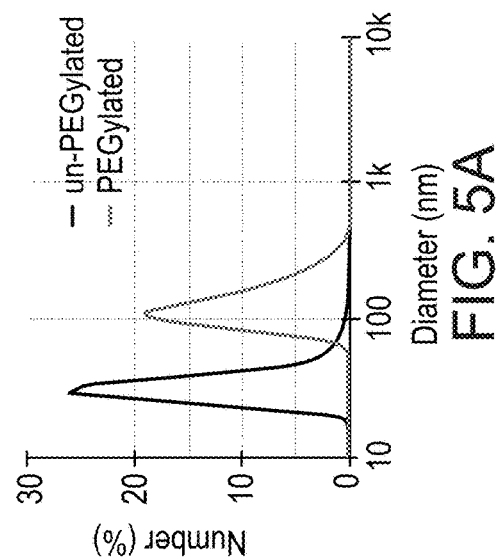
Figure 5C:
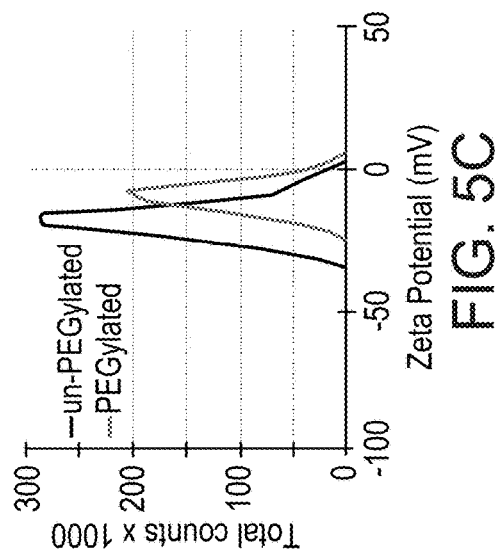

FIGS. 5A-5C are graphs showing DLS and Zeta-Potential analysis of CDLs. Un-PEGyltated and PEGylated hMSC derived CDLs were analyzed for size, size distribution and charge by Number-weight DLS (FIG. 5A), Volume-Weight DLS (FIG. 5B) and Zeta-potential (FIG. 5C).

Figure 6:
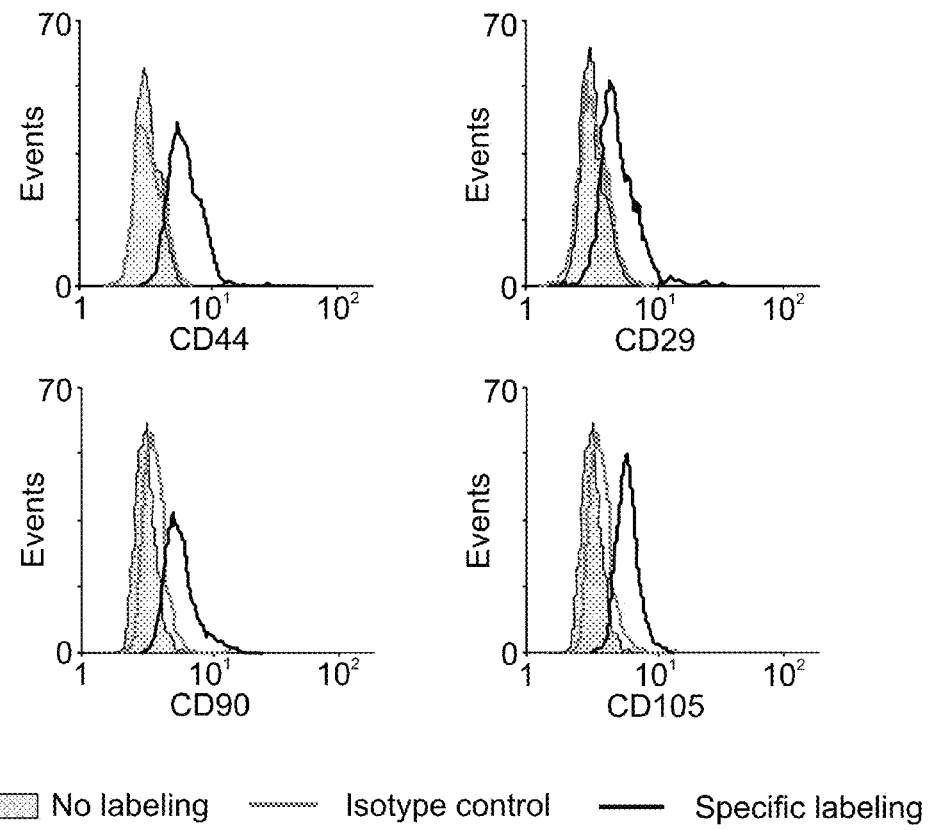

FIG. 6 shows the surface marker characterization of hMSCs derived liposomes. CDL's were prepared from hMSCs, conjugated with Tosyl-activated Dynabeads™ and analyzed by FACS for hMSCs specific membranal markers (i.e., CD44, CD29, CD90 and CD105).

Figure 7A:
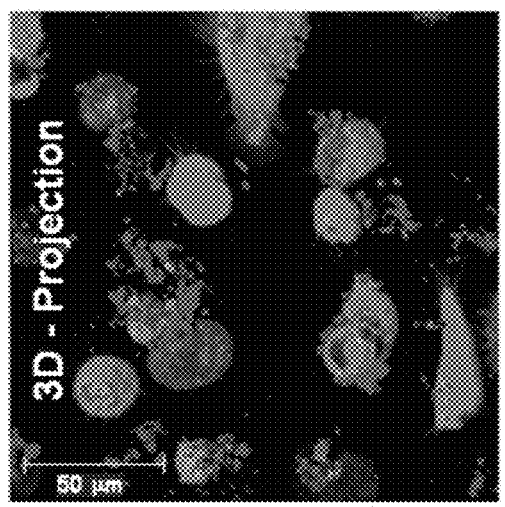
Figure 7B:
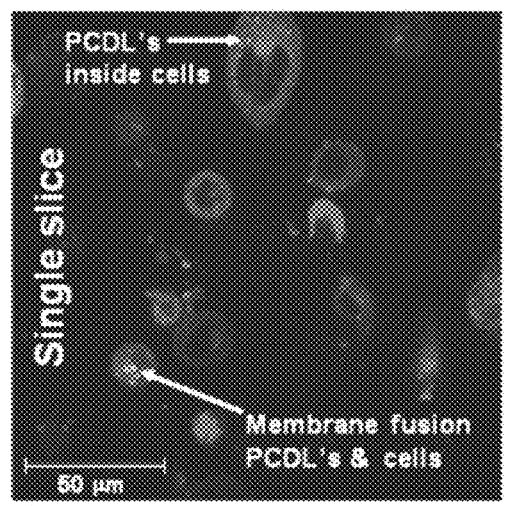

FIGS. 7A-7B show the binding of CDLs prepared from hMSCs to prostate cancer cell-line (PC3). PC3 cells were labeled with DiO (green) and incubated with CDLs that were previously labeled with DiI (red). Cultures were imaged following 12 hrs incubation. Representative 3D-projection (FIG. 7A) and single-slice (FIG. 7B) images are presented.

Figure 8A:
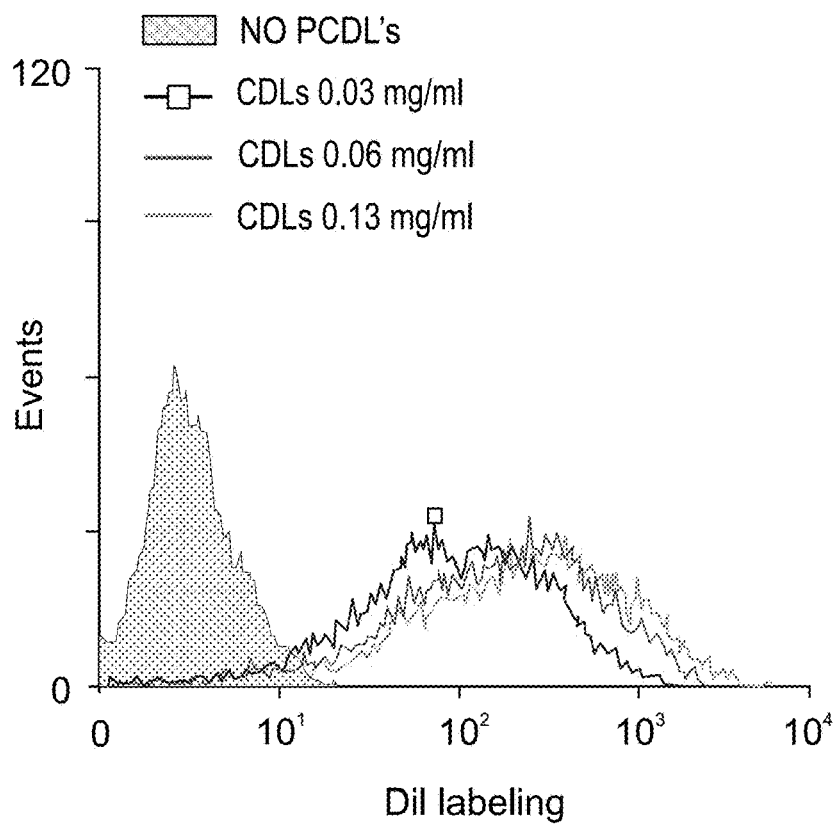
Figure 8B:
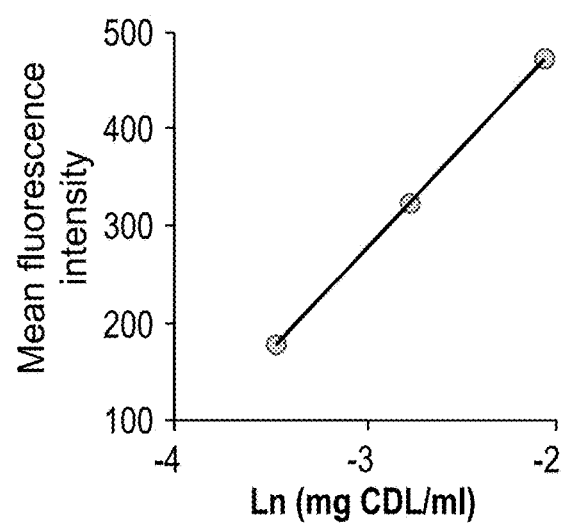

FIGS. 8A-8B are graphs and FACS histograms showing concentration-dependent binding of CDLs prepared from hMSCs to prostate cancer cell-line (PC3). PC3 cells were incubated with various concentrations of CDLs that were previously labeled with a red fluorescent dye (DiI). Following 24 hrs incubation, cells were washed, harvested and analyzed by FACS (FIG. 8A). The mean fluorescence intensity of the cells was calculated and plotted vs. the natural logarithm of CDLs concentration (FIG. 8B).

Figure 9:
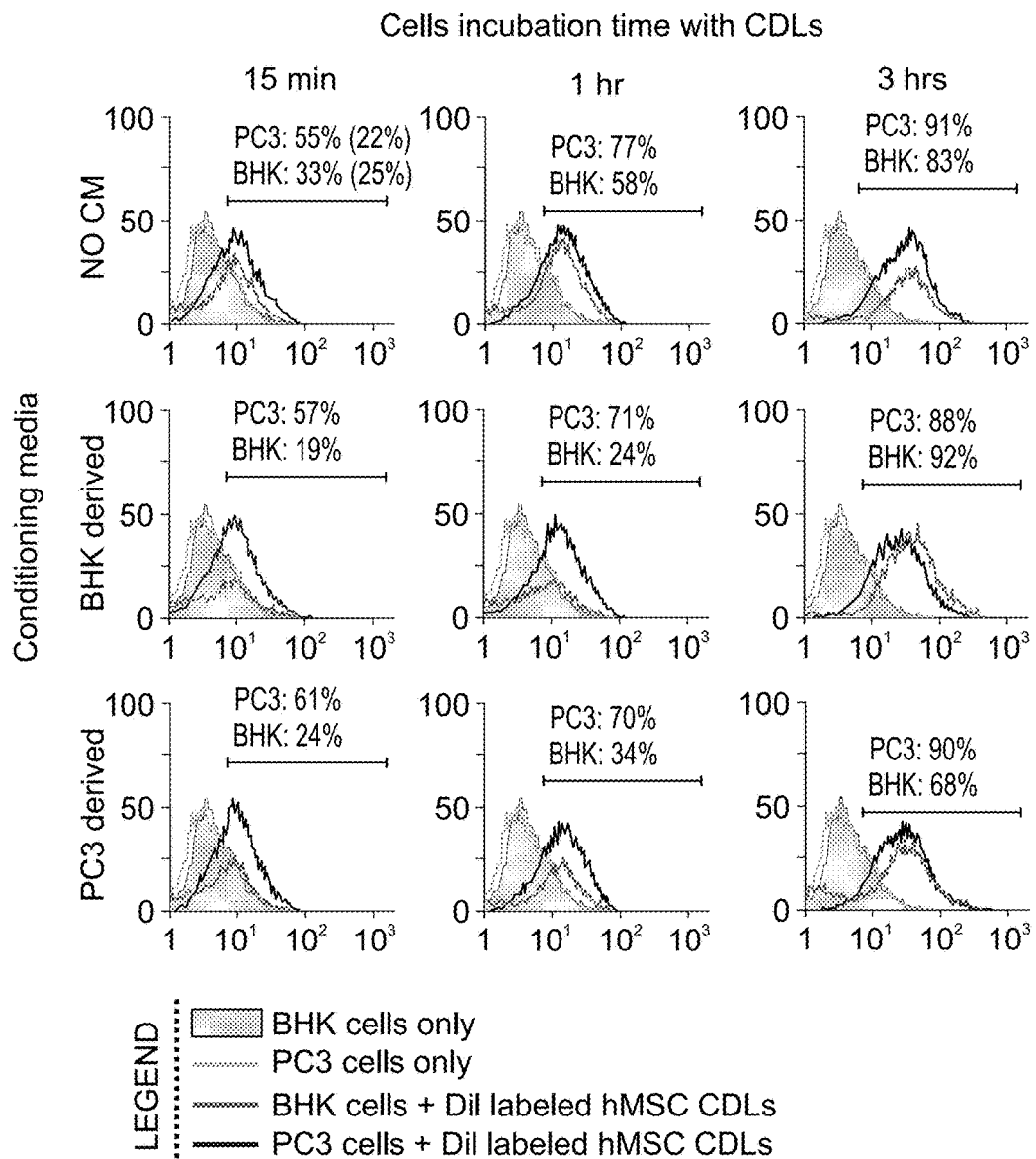

FIG. 9 show the specific binding of CDLs, prepared from conditioned hMSCs (i.e cell cultured with conditioned media of cancer cells), to prostate cancer cell-line (PC3). DiI-labeled CDLs were prepared from hMSCs which were previously incubated for 24 hrs with condition media derived from a prostate cancer cell-line (PC3) and from a non-human cell-line (BHK). The resulting "conditioned" CDLs, as well as CDLs prepared from unconditioned hMSCs (control, NO CM), were incubated with PC3 and BHK cells for 15 min, 1 hr and 3 hrs. Following incubation, the cells were washed, harvested and analyzed by FACS. The percentage in the marker refers to the ratio of DiI-labeled cells within the marker. The percentage in brackets, designated on the upper-left histogram only, refers to the ratio of unlabeled cells within the marker. The marker and the ratio of unlabeled cells within the marker are identical for all histograms.

Figure 10A:
Figure 10A:
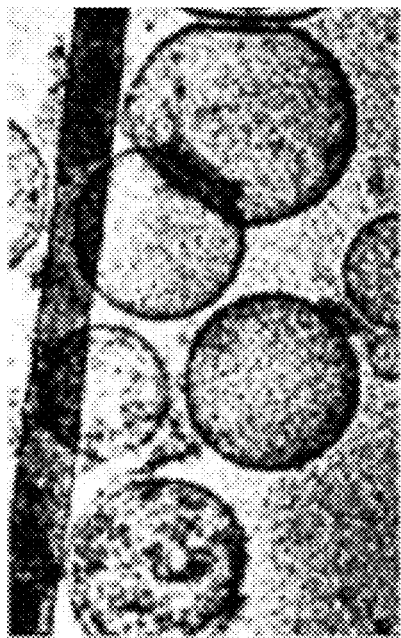
Figure 10A:
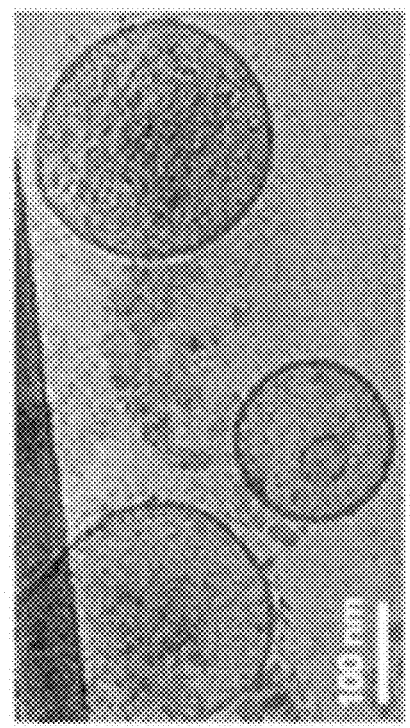
Figure 10B:
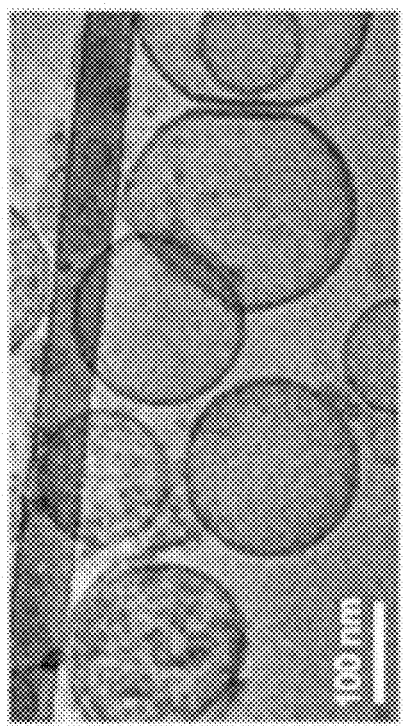

FIGS. 10A-10B are cryo-TEM images of hMSCs derived liposomes entrapping soluble Tumor necrosis factor-related apoptosis-inducing ligand (sTRAIL). sTRAIL-containing CDLs (FIG. 10A) and empty CDLs (FIG. 10B) were prepared at the same final concentration and imaged by Cryo-TEM under the same conditions. To emphasize CDLs' content, the original grey-scale Cryo-TEM images (left pane) were re-colored to black and white (right pane).

Figure 11:
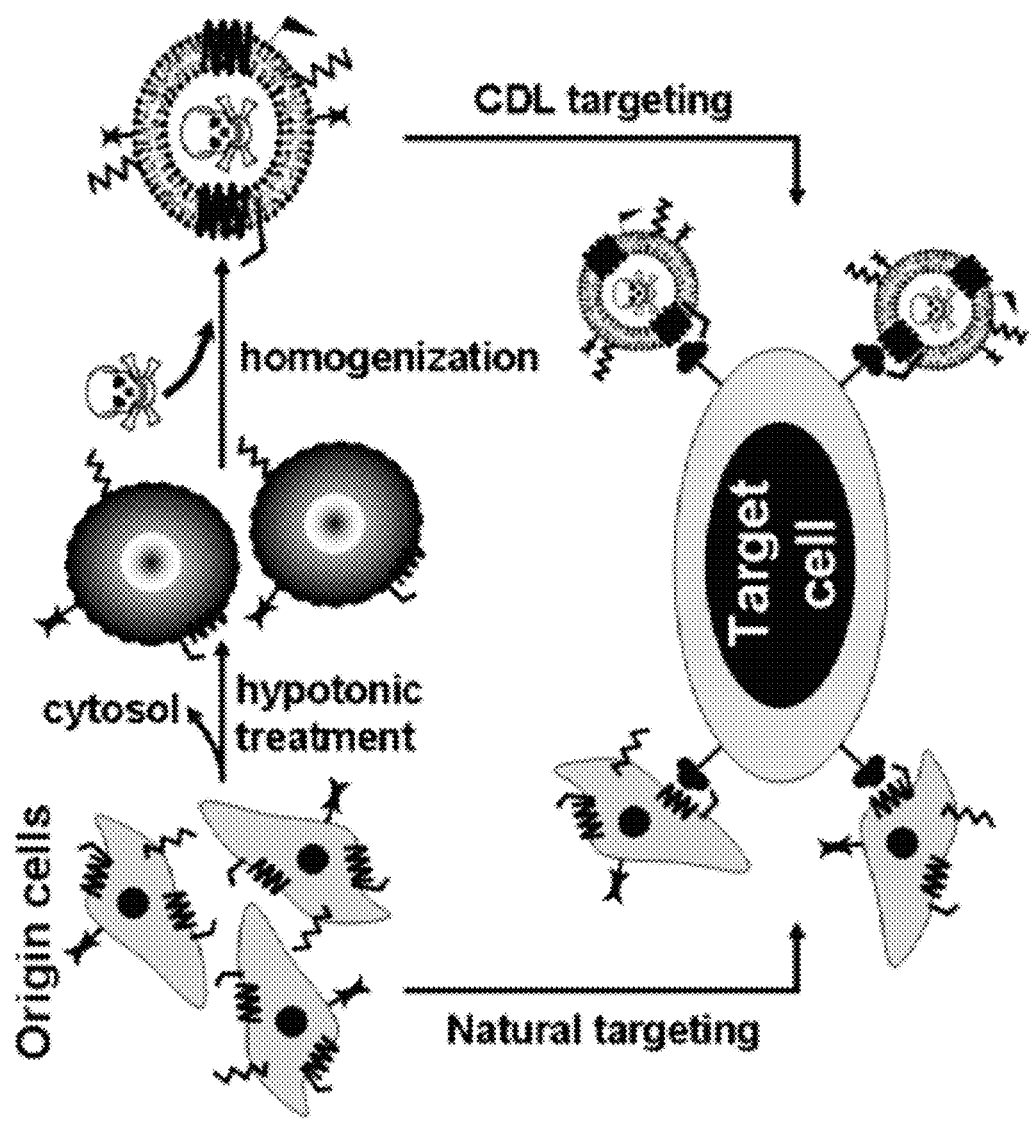

FIG. 11 is a schematic illustration of the overall design of targeted carriers based on cell-derived liposomes (CDL). Origin cells that naturally and specifically interact with target cells are selected as a source for cell derived liposomes. For example, MSC membranally interact with cancer cells therefore are selected as a source for cancer targeting carriers. Source cells undergo hypotonic treatment to generate ghost cells, which are then homogenized to produce CDL. Resulting CDL are then able to specifically bind their target cells in a similar manner to the cells they are derived from.

DESCRIPTION OF SPECIFIC EMBODIMENTS OF THE INVENTION

The present invention, in some embodiments thereof, relates to liposomal compositions and uses of same.

Before explaining at least one embodiment of the invention in detail, it is to be understood that the invention is not necessarily limited in its application to the details set forth in the following description or exemplified by the Examples. The invention is capable of other embodiments or of being practiced or carried out in various ways.

A major challenge facing cancer therapy is achieving a cytotoxic effect towards cancer cells, while sparing the healthy ones. The importance of the development of novel targeted therapeutic delivery strategies for cancer therapy has long been recognized worldwide.

The present inventors have designed a novel delivery vehicle for targeted delivery of therapeutic and diagnostic agents into cells and tissues. The delivery vehicle is liposome-based composed of a whole cell membrane fraction which comprises both natural lipids and proteins. By employing native cell membranes, the delivery vehicles of the present invention may be formulated to be of low immunogenic potential, easily home to the target tissue and can be genetically modified to express therapeutic or targeting moieties.

As is illustrated below and in the examples section, which follows and further depicted in FIG. 12, the present inventors have generated liposomes composed of whole cell membranes of mesenchymal stem cells, which are well-known for their homing capacities as well as their immunosuppressive abilities (i.e., their ability to reduce inflammation and suppress immune cells) and hypo-immunogenic features (i.e., stealth-like features that makes them less immunogenic and less recognizable as foreign matter when heterologously transplanted). The liposomes exhibit the protein signature of mesenchymal stem cells and as such are expected to mediate similar immunosuppression and migratory properties as intact mesenchymal stem cells. These cell derived liposomes were further PEGylated to increase their bioavailability and dispersion and reduce their coagulation. The cell derived liposomes were also treated to encapsulate a therapeutic agent. Altogether these findings, place the present delivery system as a pivotal tool in the diagnosis and treatment of human disease such as cancer.

Thus, according to an aspect of the present invention there is provided a composition-of-matter comprising a liposome attached to, or encapsulating a pharmaceutical agent, said liposome being composed of a whole cell membrane fraction.

As used herein the term "liposome" refers to fully closed carrier molecules comprising a spherical lipid membrane which itself is in a liquid crystalline phase or a liquid gel phase, in which an entrapped liquid volume is contained. The two liquid phases are immiscible. Thus, liposomes of the present invention (also referred to herein as cell derived liposomes (CDLs), similar to membranes of cells, are in an entirely gel/liquid state and/or liquid crystal state and not in a solid state.

The liposomes of some embodiments of the present invention have an expected protein to lipid ration of about 0.8 w/w.

Of note, the protein content of hMSCc CDLs is about 0.8 mg/$10^8$ cells (as determined by Bradford assay). The lipid content can be easily determined using the Stewart phospholipids assay. It is expected to be about 1 mg/$10^8$ cells.

The following calculation can be used to determine the theoretical phospholipids content. Since the dry mass of a single mammalian cell is in the magnitude of $10^{-7}$ mg[1] and since phospholipids constitutes approximately 10% of the dry cell mass[2] then the theoretical yield of the cell derived liposomes' production process (assumed 100% efficiency) should be in the magnitude of $10^{-8}$ mg phospholipids per single cell or 1 mg per $10^8$ cells.

Liposomes include niosomes, transfersomes, emulsions, foams, micelles, liquid crystals, dispersions, lamellar layers and the like.

The liposomes may be unilamellar or multilamellar.

According to a specific embodiment of the invention, the liposomes are unilamellar, as determined by Cryo-TEM.

According to a specific embodiment of the invention, the liposomes exhibit native membrane symmetry and expression of native markers.

Liposomes of the present invention are composed of a whole cell membrane fraction.

As used herein the phrase "cell membrane" or "cellular membrane" (which may be interchangeably used) refers to a biological membrane, which surrounds the cell or is an integral part of an organelle thereof (e.g., chloroplast, ER, golgi, mitochondrion, vacuole, nucleus and a lysosome).

According to a specific embodiment of the present invention the cell membrane refers to the plasma membrane. The use of plasma membrane is of a specific advantage since it presents proteins, which are associated with cell-to-cell interactions, as well as other recognition molecules, such as receptors that bind soluble ligands.

As used herein "a whole cell membrane fraction" refers to a fraction, which does not include lipids alone but also includes membrane proteins.

Examples of membrane proteins include, but are not limited to, integral proteins, transmembrane proteins, lipid anchored proteins and glycoproteins.

According to an embodiment of the invention the whole cell membrane fraction also includes carbohydrates.

According to a specific embodiment the cell is a eukaryotic cell [e.g., mammalian (such as human), plant, insect cell].

According to an additional specific embodiment the eukaryotic cell is a mammalian cell.

According to yet an additional embodiment the cell can be a primary cell (i.e., non-immortalized and at times not cultured) or a cell-line.

According to yet an additional embodiment the cell can be an embryonic cell.

Use of a primary cell may be advantageous for clinical use where non-cultured cells are used in autologous or non-autologous (syngeneic allogeneic or xenogeneic) settings.

According to a specific embodiment the eukaryotic cell is a stem cell.

As used herein, the phrase "stem cells" refers to cells, which are capable of remaining in an undifferentiated state (e.g., pluripotent or multipotent stem cells) for extended periods of time in culture until induced to differentiate into other cell types having a particular, specialized function (e.g., fully differentiated cells). Preferably, the phrase "stem cells" encompasses embryonic stem cells (ESCs), induced pluripotent stem cells (iPS), adult stem cells, mesenchymal stem cells and hematopoietic stem cells.

According to a specific embodiment the stem cell is a mesenchymal stem cell.

Mesenchymal stem cells are the formative pluripotent blast cells. Mesenchymal stem cells (MSCs) give rise to one or more mesenchymal tissues (e.g., adipose, osseous, cartilaginous, elastic and fibrous connective tissues, myoblasts, cardiac like cells) as well as to tissues other than those originating in the embryonic mesoderm (e.g., neural cells) depending upon various influences from bioactive factors such as cytokines. MSCs can be isolated from embryonic yolk sac, placenta, umbilical cord, fetal and adolescent skin, blood, bone marrow, adipose and other tissues, although their abundance in the bone marrow far exceeds their abundance in other tissues. MSCs have been shown to have immunosuppressive functions in various settings, including autoimmune diseases and transplantation, rendering liposomes generated therefrom ultimate tools in inflammatory and autoimmune settings.

Methods of isolating, purifying and expanding mesenchymal stem cells (MSCs) are known in the arts and include, for example, those disclosed by Caplan and Haynesworth in U.S. Pat. No. 5,486,359 and Jones E. A. et al., 2002, Isolation and characterization of bone marrow multipotential mesenchymal progenitor cells, Arthritis Rheum. 46(12): 3349-60.

Preferably, mesenchymal stem cell cultures are generated by diluting BM aspirates (usually 20 ml) with equal volumes of Hank's balanced salt solution (HBSS; GIBCO Laboratories, Grand Island, N.Y., USA) and layering the diluted cells over about 10 ml of a Ficoll column (Ficoll-Paque; Pharmacia, Piscataway, N.J., USA). Following 30 minutes of centrifugation at 2,500×g, the mononuclear cell layer is removed from the interface and suspended in HBSS.Cells are then centrifuged at 1,500×g for 15 minutes and resuspended in a complete medium (MEM, α medium without deoxyribonucleotides or ribonucleotides; GIBCO); 20% fetal calf serum (FCS) derived from a lot selected for rapid growth of MSCs (Atlanta Biologicals, Norcross, Ga.); 100 units/ml penicillin (GIBCO), 100 µg/ml streptomycin (GIBCO); and 2 mM L-glutamine (GIBCO). Resuspended cells are plated in about 25 ml of medium in a 10 cm culture dish (Corning Glass Works, Corning, N.Y.) and incubated at 37° C. with 5% humidified $CO_2$. Following 24 hours in culture, nonadherent cells are discarded, and the adherent cells are thoroughly washed twice with phosphate buffered saline (PBS). The medium is replaced with a fresh complete medium every 3 or 4 days for about 14 days. Adherent cells are then harvested with 0.25% trypsin and 1 mM EDTA (Trypsin/EDTA, GIBCO) for 5 min at 37° C., replated in a 6-cm plate and cultured for another 14 days. Cells are then trypsinized and counted using a cell counting device such as for example, a hemocytometer (Hausser Scientific, Horsham, Pa.). Cultured cells are recovered by centrifugation and resuspended with 5% DMSO and 30% FCS at a concentration of 1 to $2\times10^6$ cells per ml. Aliquots of about 1 ml each are slowly frozen and stored in liquid nitrogen.

To expand the mesenchymal stem cell fraction, frozen cells are thawed at 37° C., diluted with a complete medium and recovered by centrifugation to remove the DMSO. Cells are resuspended in a complete medium and plated at a concentration of about 5,000 cells/cm$^2$. Following 24 hours in culture, nonadherent cells are removed and the adherent cells are harvested using Trypsin/EDTA, dissociated by passage through a narrowed Pasteur pipette, and preferably replated at a density of about 1.5 to about 3.0 cells/cm$^2$. Under these conditions, MSC cultures can grow for about 50 population doublings and be expanded for about 2000 fold [Colter DC., et al. Rapid expansion of recycling stem cells in cultures of plastic-adherent cells from human bone marrow. Proc Natl Acad Sci USA. 97: 3213-3218, 2000].

MSC cultures utilized by the present invention preferably include three groups of cells, which are defined by their morphological features: small and agranular cells (referred to as RS-1, herein below), small and granular cells (referred to as RS-2, herein below) and large and moderately granular cells (referred to as mature MSCs, herein below). The presence and concentration of such cells in culture can be assayed by identifying a presence or absence of various cell surface markers, by using, for example, immunofluorescence, in situ hybridization, and activity assays.

When MSCs are cultured under the culturing conditions of the present invention they exhibit negative staining for the hematopoietic stem cell markers CD34, CD11B, CD43 and CD45. A small fraction of cells (less than 10%) are dimly positive for CD31 and/or CD38 markers. In addition, mature MSCs are dimly positive for the hematopoietic stem cell marker, CD117 (c-Kit), moderately positive for the osteogenic MSCs marker, Stro-1 [Simmons, P. J. & Torok-Storb, B. (1991). Blood 78, 5562] and positive for the thymocytes and peripheral T lymphocytes marker, CD90 (Thy-1). On the other hand, the RS-1 cells are negative for the CD117 and Stro1 markers and are dimly positive for the CD90 marker, and the RS-2 cells are negative for all of these markers.

Other cells, which may be used as an effective source for whole cell membrane fraction include, but are not limited to, endothelial cells, hepatic cells, pancreatic cells, bone cells, chondrocytes, neuronal cells and the like.

The cells can be used native (i.e., not manipulated by genetic modification) or genetically modified to manipulate the membrane composition of the cell.

The advantage of genetic modification is in its increased efficiency. Essentially all (>95%) the CDLs generated from genetically modified cells express the gene-of-interest. The gene-of-interest may be constitutively expressed on the cell source (by integration to the cells genome) or transiently expressed (episomal expression) such as to avoid hazardous implications of stable transfection agents (e.g., lentiviral and retroviral vectors).

Thus, the cells may be genetically modified to express a gene-of-interest (i.e., not naturally expressed in the native membrane but also in order to enhance the expression of endogenous proteins that are naturally expressed on the cell's membrane but in lower levels).

According to specific embodiments, the gene-of-interest encodes a membrane protein. The gene-of-interest may be a native membrane protein or modified to have a membrane localization signal and other motifs needed for membrane anchorage e.g., a transmembrane domain.

Examples of membrane proteins which may be heterologously (exogenously) expressed include, but are not limited to, a targeting protein (e.g., antibodies, receptors, membrane anchored ligands, decoys), a protein which affects the chemistry of the membrane (e.g., structural proteins, charged proteins), a diagnostic protein (e.g., an enzyme as described in length below) and a therapeutic protein (as described in length below).

A targeting moiety includes a targeting protein such as an antibody, a receptor ligand and a non-proteinecious molecule such as carbohydrates, which binds cell surface or extra-cellular matrix markers. For example, prostate-specific membrane antigen (PSMA) that is over-expressed on prostate cancer cells can be targeted by its ligand NAAG[3] conjugated to a transmembranal motif (e.g, truncated LIME)[4]. This may be achieved, by genetically engineering the cells (of which the CDLs are derived from) to express the chimeric or natural form of NAAG. For example, the expression plasmid encoding LIME is constructed by PCR and subsequent insertion of the corresponding fragment into pcDNA3.1 (Invitrogen). The primers also have BamHI (5' primer and 3' primer) site extension to facilitate the subcloning. The PCR product is digested with BamHI and inserted into corresponding sites in pcDNA3.1(+) (CLONTECH Laboratories, Inc.). For expression vector encoding LIME-acetylaspartylglutamate (NAAG), the open reading frame can be inserted into plasmid coding LIME such that the NAAG is conjugated trough its N-terminus and maintains its C-terminus free to react with PSMA [i.e., LIME (C)-(N)NAAG-COOH]. Alternatively, expression plasmid encoding NAAG-LIME chimera can be constructed following the method described previously described for CD8-LIME chimera[5]. Fragments corresponding to NAAG and LIME transmembrane region were generated by PCR. Primers encoding the 3' sequences of the NAAG and the 5' sequences of the LIME fragment were designed to overlap, such that annealing of the two products yielded a hybrid template. From this template, the chimera is amplified using external primers containing XbaI sites. The NAAG-LIME chimera is inserted into pcDNA3.1(+).

As used herein, the phrase "surface marker", refers to any chemical structure, which is specifically displayed at uniquely high density, and/or displayed in a unique configuration by a cell surface or extracellular matrix of the target cell/tissue.

For example, the targeting moiety may be useful for targeting to tumor cells. For example, it is generally accepted that the intracellular environment of tumor cells is more alkaline compared to their immediate extracellular environment, which in turn is more acidic than the microenvironment found in the angiogenic blood vessels feeding the tumor. In addition, many previous studies have shown that the surface charges of tumor cells is more negative compared to benign normal cells and even less invasive tumor cells. Accordingly, it may be useful to express membrane-bound enzymes and/or proteins, which will render the liposomes with a positive charge only in the acidic intermediate extracellular environment of the tumor. For example, any membranal protein with a pI of about 7.2-7.4 that falls between the high alkaline pH of the angiogenic blood vessels (pH>7.4) and the low acidic pH of the tumor immediate extracellular environment (pH<7.2) can be used. Such proteins can be specifically identified by cross referencing the RCSB Protein Data Bank (PDB) for human plasma membrane proteins. The expected desirable pI (7.2-7.4) for those proteins can be calculated using the standard iterative algorithm[10, 11] that gives relatively precise results of pI calculations for raw protein sequences[12, 13]. The algorithm is used in the Compute pI/Mw tool at the ExPASy server. Such liposomes are expected to have negative or neutral charge in the alkaline microenvironment of the angiogenic tumor vessels and positive charge in the more acidic immediate extracellular environment of the tumor. Accordingly, this charge alteration will assist both liposomal extravasation, which is significantly enhanced for negative of neutral particles, and intra-tumor delivery which is more easily accomplished with positively charge particles[8, 14, 15].

Ample guidance regarding surface markers specifically over-expressed in diseases such as cancer, and antibodies specific for such surface markers is provided in the literature of the art (for example, refer to: A M Scott, C Renner. "Tumour Antigens Recognised by Antibodies." In: Encyclopedia of Life Sciences, Nature Publishing Group, Macmillan, London, UK, www(dot)els(dot)net, 2001).

Diseases associated with a target cell/tissue specifically displaying a growth factor receptor/TAA surface marker which are amenable to treatment by the method of the present invention include, for example, some of the numerous diseases which specifically display growth factor receptors/TAAs, such as EGF receptor, platelet derived growth factor (PDGF) receptor, insulin like growth factor receptor, vascular endothelial growth factor (VEGF) receptor, fibroblast growth factor (FGF) receptor, transferrin receptor, and folic acid receptor. Specific examples of such diseases and the growth factor receptors/TAAs which these specifically display are listed in Table 1, below.

TABLE 1

| Review reference | Malignancy type | Receptor* |
|---|---|---|
| Kim, E. S. et al., 2001. Curr Opin Oncol 13, 506-13; Kuan et al., 2000. Brain Tumor Pathol. 2000; 17: 71-8 | Malignant glioma, glioblastoma, head and neck, breast, colon, lung, prostate, kidney, ovary, brain, pancreas, bladder | EGF receptor |
| George, D., 2001. Semin Oncol 28, 27-33 | Brain, prostate | PDGF receptor |
| Wang, Y., and Sun, Y., 2002. Curr Cancer Drug Targets 2, 191-207 | Breast, lung, colon, prostate | IGF receptor |
| Rosen, L. S., 2001. Cancer J 7 Suppl 3, S120-8; Giles, F. J., 2001. Oncologist 6, 32-9 | Solid tumors, acute and chronic leukemias, myeloproliferative diseases, multiple myeloma, non-Hodgkin's lymphomas, and Hodgkin's disease | VEGF receptor |
| Lappi, D. A., 1995. Semin Cancer Biol 6, 279-88 | Melanoma, Caposi sarcoma, pancreas | FGF receptor |
| Singh, M., 1999. Curr Pharm Des 5, 443-51 | Leukemia, brain, colon, kidney, bladder | Transferrin receptor |

*Abbreviations: EGF - epidermal growth factor, PDGF - platelet derived growth factor, IGF - insulin like growth factor, VEGF - vascular endothelial growth factor, FGF - fibroblast growth factor.

In a preferred embodiment, the ligand is an antibody or an antibody fragment, targeting antigens specific to a receptor on a target cell. Antibodies can be monoclonal antibodies, polyclonal antibodies or antibody fragments, which are target specific. In an embodiment, the antibodies attached to the liposomes are anti-CD19, anti-CD20, or anti-CD22, for specific binding to a B-cell epitope. These antibodies or antibody fragments are typically derived from hybridomas that show positive reactivity toward the affected B-cells. It is contemplated that other antibodies or antibody fragments targeting any other cell in the body can be similarly used. For example, anti-CD19 antibodies are used to target liposome containing an entrapped agent to malignant B-cells. The antibody recognizes a unique epitope, the CD19 surface antigen, on the B-cells.

Methods of expressing heterologous proteins in eukaryotic cells are well known in the art.

Thus, an exogenous polynucleotide sequence designed and constructed to express at least a functional portion of the gene-of-interest may be expressed in the cells from which membranes are later extracted. Accordingly, the exogenous polynucleotide sequence may be a DNA or RNA sequence of the gene-of-interest.

The phrase "functional portion" as used herein refers to part of the encoded protein (i.e., a polypeptide), which exhibits functional properties of the enzyme such as binding to a substrate. For example, the functional portion of an antibody may be the variable region conferring specificity and additional/or alternatively the constant region, i.e., Fc, which may activate complement and induce cell killing. For example, cells can be transfected with genes encoding one or more members from the GPCRs family (e.g., CCR5, CXCR4 etc.) that will render the liposomes targeted against abundant of cellular pathologies including auto-immune and viral diseases (e.g., HIV/AIDS).

To express exogenous gene-of-interest in eukaryotic (e.g., mammalian) cells, a polynucleotide sequence encoding the gene-of-interest is preferably ligated into a nucleic acid construct suitable for eukaryotic cell expression. Such a nucleic acid construct includes a promoter sequence for directing transcription of the polynucleotide sequence in the cell in a constitutive or inducible manner.

Constitutive promoters suitable for use for mammalian expression with the present invention are promoter sequences, which are active under most environmental conditions and most types of cells such as the cytomegalovirus (CMV) and Rous sarcoma virus (RSV). Inducible promoters suitable for use with the present invention include for example the inducible promoter of the tetracycline-inducible promoter (Zabala M, et al., Cancer Res. 2004, 64(8): 2799-804).

The nucleic acid construct (also referred to herein as an "expression vector") of the present invention includes additional sequences, which render this vector suitable for replication and integration in prokaryotes, eukaryotes, or preferably both (e.g., shuttle vectors). In addition, a typical cloning vector may also contain a transcription and translation initiation sequence, transcription and translation terminator and a polyadenylation signal. By way of example, such constructs will typically include a 5' LTR, a tRNA binding site, a packaging signal, an origin of second-strand DNA synthesis, and a 3' LTR or a portion thereof.

The nucleic acid construct of the present invention typically includes a signal sequence for directing the translated polypeptide to the membrane and additionally a membrane anchor domain such as a transmembrane domain or a lipid based anchor (e.g., GPI).

Eukaryotic promoters typically contain two types of recognition sequences, the TATA box and upstream promoter elements. The TATA box, located 25-30 base pairs upstream of the transcription initiation site, is thought to be involved in directing RNA polymerase to begin RNA synthesis. The other upstream promoter elements determine the rate at which transcription is initiated.

Preferably, the promoter utilized by the nucleic acid construct of the present invention is active in the specific cell population transformed. Examples of cell type-specific and/or tissue-specific promoters include promoters such as albumin that is liver specific [Pinkert et al., (1987) Genes Dev. 1:268-277], lymphoid specific promoters [Calame et al., (1988) Adv. Immunol. 43:235-275]; in particular promoters of T-cell receptors [Winoto et al., (1989) EMBO J. 8:729-733] and immunoglobulins; [Banerji et al. (1983) Cell 33729-740], neuron-specific promoters such as the neurofilament promoter [Byrne et al. (1989) Proc. Natl. Acad. Sci. USA 86:5473-5477], pancreas-specific promoters [Edlunch et al. (1985) Science 230:912-916] or mammary gland-specific promoters such as the milk whey promoter (U.S. Pat. No. 4,873,316 and European Application Publication No. 264,166).

Enhancer elements can stimulate transcription up to 1,000 fold from linked homologous or heterologous promoters. Enhancers are active when placed downstream or upstream from the transcription initiation site. Many enhancer elements derived from viruses have a broad host range and are active in a variety of tissues. For example, the SV40 early gene enhancer is suitable for many cell types. Other enhancer/promoter combinations that are suitable for the present invention include those derived from polyoma virus, human or murine cytomegalovirus (CMV), the long term repeat from various retroviruses such as murine leukemia virus, murine or Rous sarcoma virus and HIV. See, Enhancers and Eukaryotic Expression, Cold Spring Harbor Press, Cold Spring Harbor, N.Y. 1983, which is incorporated herein by reference.

In the construction of the expression vector, the promoter is preferably positioned approximately the same distance from the heterologous transcription start site as it is from the transcription start site in its natural setting. As is known in the art, however, some variation in this distance can be accommodated without loss of promoter function.

Polyadenylation sequences can also be added to the expression vector in order to increase the efficiency of mRNA translation. Two distinct sequence elements are required for accurate and efficient polyadenylation: GU or U rich sequences located downstream from the polyadenylation site and a highly conserved sequence of six nucleotides, AAUAAA, located 11-30 nucleotides upstream. Termination and polyadenylation signals that are suitable for the present invention include those derived from SV40.

In addition to the elements already described, the expression vector of the present invention may typically contain other specialized elements intended to increase the level of expression of cloned nucleic acids or to facilitate the identification of cells that carry the recombinant DNA. For example, a number of animal viruses contain DNA sequences that promote the extra chromosomal replication of the viral genome in permissive cell types. Plasmids bearing these viral replicons are replicated episomally as long as the appropriate factors are provided by genes either carried on the plasmid or with the genome of the host cell.

The vector may or may not include a eukaryotic replicon. If a eukaryotic replicon is present, then the vector is amplifiable in eukaryotic cells using the appropriate selectable marker. If the vector does not comprise a eukaryotic replicon, no episomal amplification is possible. Instead, the recombinant DNA integrates into the genome of the engineered cell, where the promoter directs expression of the desired nucleic acid.

The expression vector of the present invention can further include additional polynucleotide sequences that allow, for example, the translation of several proteins from a single mRNA such as an internal ribosome entry site (IRES) and sequences for genomic integration of the promoter-chimeric polypeptide.

Examples for mammalian expression vectors include, but are not limited to, pcDNA3, pcDNA3.1(+/−), pGL3, pZeoSV2(+/−), pSecTag2, pDisplay, pEF/myc/cyto, pCMV/myc/cyto, pCR3.1, pSinRep5, DH26S, DHBB, pNMT1, pNMT41, pNMT81, which are available from Invitrogen, pCI which is available from Promega, pMbac, pPbac, pBK-RSV and pBK-CMV which are available from Strategene, pTRES which is available from Clontech, and their derivatives.

Expression vectors containing regulatory elements from eukaryotic viruses such as lentiviruses and retroviruses can be also used. SV40 vectors include pSVT7 and pMT2. Vectors derived from bovine papilloma virus include pBV-1MTHA, and vectors derived from Epstein Bar virus include pHEBO, and p2O5. Other exemplary vectors include pMSG, pAV009/A⁺, pMT010/A⁺, pMAMneo-5, baculovirus pDSVE, and any other vector allowing expression of proteins under the direction of the SV-40 early promoter, SV-40 later promoter, metallothionein promoter, murine mammary tumor virus promoter, Rous sarcoma virus promoter, polyhedrin promoter, or other promoters shown effective for expression in eukaryotic cells.

Alternatively, cells, membranes, ghosts or CDLs (either of which may be native or genetically modified), may be chemically treated such as to present a protein, a saccharide, a synthetic polymer, a peptide or any combination of same. Methods of modifying the membrane with a synthetic polymer are described herein below and in the examples section, which follows. Such a chemical attachment may be effected at any stage from live cultured or suspended cells to produced CDLs.

For example, the CDLs may be also chemically conjugated with folate that may further enhance their targeting and attachment to tumor cells, which are known to express higher levels of folate receptors compared to benign cells.

According to another example, it is also possible to permanently modulate the CDLs to have a more positive surface charge by treating them with cations, salts or polycations (e.g., Polybrene®, polyethyleneimine and Poly-L-Lysine) rendering them more positive to better target the tumor angiogenic vasculature.

Non-native material can be also introduced to the surface of the CDLs by fusion (e.g., PEG or detergent induced) with other liposomes (e.g., cell-derived or synthetic) that may be comprised of well characterized lipids, proteins and additives. Such fusion, creating hybrid CDLs, can be used to conjugate any moieties (e.g., targeting, therapeutic, diagnostic, stealth-rendering etc.) to the CDLs and to alter their surface properties. See Example 5 for further guidance on liposomal fusion.

Synthetic polymers are typically used to prevent or reduce coagulation, increase dispersion, reduce interaction with blood components, evade non-specific uptake by the mononuclear phagocytic system and prolong the particle circulation time to a large extent thus, rendering the liposomes with properties and features that are commonly referred to as stealth properties or long-circulating liposomes. Accordingly, the pH nano-environment at the particle surface may also be dependent upon the length of these molecules.

There are numerous polymers, which may be attached to lipids. Polymers typically used as lipid modifiers include, without being limited thereto: polyethylene glycol (PEG), polysialic acid, polylactic (also termed polylactide), polyglycolic acid (also termed polyglycolide), apolylactie-polyglycolic acid' polyvinyl alcohol, polyvinylpyrrolidone, polymethoxazoline, polyethyloxazoline, polyllydroxyetlyloxazolille, solyhydroxypryloxazoline, polyaspartarllide, polyhydroxypropyl methacrylamide, polymethacrylamide, polydimethylacrylamide, polyvinylmethylether, polyhydroxyethyl acrylate, derivatized celluloses such as hydroxymethylcellulose or hydroxyethylcellulose.

The polymers may be employed as homopolymers or as block or random copolymers.

The most commonly used and commercially available lipids derivatized into lipopolymers are those based on phosphatidyl ethanolamine (PE), usually distearylphosphatidylethanolamine (DSPE).

A specific family of lipopolymers, which may be employed by the invention include PEG-DSPE (with different lengths of PEG chains) in which the PEG polymer is linked to the lipid via a carbamate linkage and Polyethyleneglycol distearoylglycerol. The PEG moiety headgroup preferably has a molecular weight from about 750 Da to about 20,000 Da. More preferably, the molecular weight is from about 750 Da to about 12,000 Da and most preferably between about 1,000 Da to about 5,000 Da. Two exemplary DSPE-PEG are those wherein PEG has a molecular weight of 2000 Da, and of 5000a designated herein DSPE-PEG (2000) (DSPE-PEG2k) and DSPE-PEG(5000) (DSPE-PEG5k).

Specific families of lipopolymers, which may be also employed by the invention, include C8 and C16 mPEG Ceramides (with different lengths of PEG chains) in which the PEG-Ceramides contain ester linkages between the PEG and ceramide moieties that allow the compound to be easily metabolized. The PEG moiety headgroup preferably has a molecular weight from about 750 Da to about 2,000 Da. More preferably, the molecular weight is about 2,000 Da.

Conventional post-insertion PEGylation of common liposomes requires heating or solublization in a detergent containing solution that might damage surface proteins and lead to encapsulate leakage. Therefore, CDLs may be also PEGylated by the two following described methods or their combination. Primarily, PEGylated CDLs will be prepared by detergent-dialysis incorporation of PEGylated lipids into the ghost cell membrane (prior to CDLs preparation). Following, direct PEGylation of the CDLs may be performed with monomethoxy-PEG activated by succinimidyl succinate, which has been proven to increase the transfection efficiency and reduce serum mediated inactivation of PEGylated lentiviral particles, used as gene transduction vectors[16].

Chemical binding of non-proteinaceous components (e.g., synthetic polymers, carbohydrates and the like) to the liposomal surface may be employed. Thus, a non-proteinaceous moiety, may be covalently or non-covalently linked to, embedded or adsorbed onto the liposome using any linking or binding method and/or any suitable chemical linker known in the art. The exact type and chemical nature of such cross-linkers and cross linking methods is preferably adapted to the type of affinity group used and the nature of the liposome. Methods for binding or adsorbing or linking the enzyme and/or targeting moiety are also well known in the art.

For example, the enzyme and/or targeting moiety may be attached to a group at the interface via, but not limited to, polar groups such as amino, SH, hydroxyl, aldehyde, formyl, carboxyl, His-tag or other polypeptides. In addition, the enzyme and/or targeting moiety may be attached via, but not limited to, active groups such as succinimidyl succinate, cyanuric chloride, tosyl activated groups, imidazole groups, CNBr, NHS, Activated CH, ECH, EAH, Epoxy, Thiopropyl, Activated Thiol, etc. Moreover, the enzyme and/or targeting moiety may be attached via, but not limited to, hydrophobic bonds (Van Der Waals) or electrostatic interactions that may or may not include cross-linking agents (e.g., bivalent anions, poly-anions, poly-cations etc.).

Once the cell source is available the liposomes are made. Thus, there is provided a method of producing liposomes comprising,
(a) subjecting cells to hypotonic conditions, so as to obtain ruptured cell membranes and/or ghost cells (also termed ghosts); and
(b) homogenizing the ruptured cell membranes and/or ghosts to thereby produce liposomes.

The method may be practiced according to other well accepted protocols known in the art such as that of Boone, C. W., Ford, L. E., Bond, H. E., Stuart, D. C. & Lorenz, D. Isolation of plasma membrane fragments from HeLa cells. J Cell Biol 41, 378-392 (1969); and Westerman and Jensen Methods Enzymol. 2003; 373:118-27 (each of which is incorporated herein by reference) with or without modifications.

As used herein, the term "ghosts" refers to a cell that all of its cytoplasmic contents and/or nucleolus were removed by cell lysis and/or membrane rapture so that only its outer cytoplasmatic/cell membrane remains; and Without being bound to a specific protocol it is suggested in a specific embodiment that liposomes of the present invention are made in a step-wise manner. First, plasma membranes are isolated from cells ($10^9$ cells) primarily by using hypotonic treatment such that the cell ruptures and ghost cells are formed. Alternatively, ghost cells can be formed using mild sonication, freeze-thaw, French-press, needle-passaging or solublization in detergent-containing solutions. According to a specific embodiment hypotonic treatment is effected in Tris-magnesium buffer (e.g., pH 7.4 or pH 8.6 at 4° C., pH adjustment made with HCl). Cell swelling is monitored by phase-contrast microscopy. Once the cells swell and ghosts are formed, the suspension is placed in a homogenizer. Typically, about 95% cell rupture is sufficient. The membranes/ghosts are then placed in Sucrose (0.25 M or higher) for preservation. To avoid adherence, the ghosts are placed in plastic tubes and centrifuged. A laminated pellet is produced in which the topmost lighter gray lamina consists only entirely of ghosts. However, the entire pellet is processed, to increase yields. Centrifugation (e.g., 3,000 rpm for 15 min at 4° C.) and washing (e.g., 20 volumes of Tris magnesium/TM-sucrose pH 7.4) may be repeated.

In the next step, the ghost fraction is separated by floatation in a discontinuous sucrose density gradient. A small excess of supernatant is left over the washed pellet, which now contains ghosts, nuclei, and incompletely ruptured whole cells. Additional 60% w/w sucrose in TM, pH 8.6 is added to the suspension to give a reading of 45% sucrose on a refractometer. After this step, all solutions contain TM pH 8.6. 15 ml of suspension are placed in SW-25.2 cellulose nitrate tubes and discontinuous gradient is formed over the suspension by adding 15 ml layers, respectively, of 40% and 35% w/w sucrose, and then adding 5 ml of TM-sucrose (0.25 M). The material is now centrifuged at 20,000 rpm for 10 min, 4° C. The nuclei sediment form a pellet, the incompletely ruptured whole cells are collect at the 40%-45% interface, and the ghosts are collected at the 35%-40% interface. The ghosts are collected and pooled.

In the next step, the ghosts are homogenized such as by sonication which may be followed by extrusion.

A specific sonication protocol relates to 5 second sonication using an MSE sonicator with microprobe at an amplitude setting of 8 (Instrumentation Associates, N.Y.). This short period of sonication is enough to cause the plasma membrane of the ghosts to break up into cell derived liposomes (CDLs). Under these specific conditions organelle membranes are not disrupted and these are removed by centrifugation (3,000 rpm, 15 min 4° C.). Plasma membrane vesicles (CDLs) are then purified by sedimentation in a continuous sucrose density gradient.

Liposomes comprising one or more pharmaceutical agent of the present invention are preferably in the size range of 20-1000 nm e.g., 30-1000 nm, 0.02-1.0 µm, more preferably 0.05-1.0 µm, more preferably 0.07-0.5 µm and more preferably 0.1-0.3 µm. An advantage of liposomes smaller or about 0.2 µm is that they can easily permeate through tumor vasculature (due to the EPR effect), they are not readily uptaken by macrophages and they can undergo filter sterilization.

Extrusion of liposomes through a commercially available polycarbonate membrane (e.g., from Sterlitech, Wash.) or an asymmetric ceramic membrane (e.g., Membralox), commercially available from Pall Execia, France is an effective method for reducing liposome sizes to a relatively well defined size distribution. Typically, the suspension is cycled through the membrane one or more times until the desired liposome size distribution is achieved. The liposomes may be extruded through successively smaller pore membranes (e.g., 400 nm, 100 nm and/or 50 nm pore size) to achieve a gradual reduction in liposome size and uniform distribution.

At any step prior to the homogenization, sonication and/or extrusion, that is, typically following ghosts preparation, a pharmaceutical agent may be added to the reaction mixture such that the resultant liposomes encapsulate the pharmaceutical agent.

As used herein the phrase "pharmaceutical agent" refers to a therapeutic agent or diagnostic agent, which can be used to treat or diagnose a medical condition, respectively.

According to a specific embodiment, the composition comprising the pharmaceutical agent and the liposome is hypo or non-immunogenic especially when the cell source is a mesenchymal stem cell.

Thus, the liposome of the present invention may have a pharmaceutical agent adsorbed to a surface thereof or encapsulated therein either within the intra-liposomal polar phase or the lamellar non-polar lipid phase.

Methods of conjugating molecules (e.g., targeting moieties, pharmaceutical agents, synthetic polymers and the like) to liposomes are well known in the art. For example, the pharmaceutical agent (or any other molecule) may be attached, conjugated or adsorbed to surface of the liposomes, ghosts or the cells of which the liposomes derive from based on hydrophobic interactions (Van Der Waals bonds) or electrostatic interactions with or without the use of cross-linking agents (e.g. anions and poly-anions). Hydrophobic and/or amphipathic pharmaceutical agent (or any other hydrophobic and/or amphipathic molecule) may be soulibilized, partially soulibilized or partitioned into the cells, ghosts or liposomal lipid membranes with or without the use of detergent and/or by detergent dialysis. A pharmaceutical agent (or any other molecule) may be attached, conjugated or adsorbed to surface of the liposomes, ghosts or the cells of which the liposomes derive from based on covalent bonds with active groups. A pharmaceutical agent may be attached, conjugated or adsorbed to surface of the liposomes, ghosts or the cells of which the liposomes derive from as a conjugate of an antibody or part of that specifically recognized a natural moiety found on the liposomes, ghosts or cells. For example, pharmaceutical agent may be adsorbed to the surface (inner or outer) of the liposomes via, but not limited to, polar groups such as amino, SH, hydroxyl, aldehyde, formyl, carboxyl, His-tag or other polypeptides. In addition, the pharmaceutical agents may be adsorbed via, but not limited to, active groups such as succinimidyl succinate, cyanuric chloride, tosyl activated groups, imidazole groups, CNBr, NHS, Activated CH, ECH, EAH, Epoxy, Thiopropyl, Activated Thiol, etc.

Entrapped in, adsorbed, expressed, conjugated, attached, and/or solubilized on the liposomes' surface or membrane is a therapeutic agent for delivery to the target cells and/or tissues by one or more of, but not limited to, the following mechanisms:

Direct intracellular delivery of the agent by means of membrane fusion between the liposomes and cells and/or liposomal uptake by endocytosis, phagocytosis or by any kind of transmembranal transport mechanism.

Diffusion and/or leakage of the agent from the liposome and consequent binding to the surface of the target cells/tissue and/or uptake into the target cell/tissue by diffusion, endocytosis, phagocytosis or by any kind of transmembranal transport mechanism.

Binding to the surface of the target cells and/or tissues of an agent which is permanently, constantly or transiently expressed, attached, adsorbed, conjugated and/or solubilized on the liposomes' surface or membrane.

A variety of therapeutic agents can be entrapped in lipid vesicles, including water-soluble agents that can be stably encapsulated in the aqueous compartment of the liposome, lipophilic compounds that stably partition in the lipid phase of the vesicles, or agents that can be stably or transiently attached, conjugated, adsorbed or expressed on to the outer or inner surfaces of the liposomes, e.g., by electrostatic, covalent or hydrophobic interactions.

Exemplary water-soluble compounds include small molecules (i.e., less than 1000 Daltons) or large molecules (i.e., above 1000 Daltons); biomolecules (e.g. proteinaceous molecules, including, but not limited to, peptide, polypeptide, post-translationally modified protein, antibodies etc.) or a nucleic acid molecule (e.g. double-stranded DNA, single-stranded DNA, ds/ss RNA (e.g., siRNA, antisense, ribozymes), or triple helix nucleic acid molecules or chemicals. Therapeutic agents may be natural products derived from any known organism (including, but not limited to, animals, plants, bacteria, fungi, protista, or viruses) or from a library of synthetic molecules. Therapeutic agents can be monomeric as well as polymeric compounds.

As mentioned above, the therapeutic agent may be a protein, such as an enzyme which compensates for loss in activity or poor expression of an endogenous enzyme e.g., the enzyme hexosaminidase A, a shortage of which results in Tay-Sachs disease.

Examples of therapeutic agents which may be delivered across a blood barrier to the brain, eye, testis or mammary gland include, but are not limited to antibiotic agents, anti-neoplastic agents, anti-inflammatory agents, antiparasitic agents, antifungal agents, antimycobacterial agents, antiviral agents, anticoagulant agents, radiotherapeutic agents, chemotherapeutic agents, cytotoxic agents, cytostatic agents, vasodilating agents, anti-oxidants, analeptic agents, anti-convulsant agents, antihistamine agents, neurotrophic agents, psychotherapeutic agents, anxiolytic sedative agents, stimulant agents, sedative agents, analgesic agents, anesthetic agents, birth control agents, neurotransmitter agents, neurotransmitter analog agents, scavenging agents and fertility-enhancing agents.

The liposome-entrapped compound may also be a diagnostic agent such as an imaging or a contrast agent as indium and technetium, enzymes such as horseradish peroxidase and alkaline phosphatase, MRI contrast media containing gadolinium, X-ray contrast media containing iodine, ultrasonography contrast media such as $CO_2$, europium derivatives, fluorescent substances such as carboxyfluorescein and illuminants such as N-methylacrydium derivatives.

Once the liposomes are formed (i.e., with or without a pharmaceutical agent), they may be characterized for their size distribution, composition, concentration, zeta potential, electrical surface potential, surface (local) pH, protein to lipid ratio and therapeutic efficacy in vitro and in vivo.

Experimentally tested liposomes of the present invention have the following size values as described on Table 2 below:

TABLE 2

| Without PEGylation: | With PEGylation: |
|---|---|
| Avg. by number 30 nm | Avg. by number 100 nm |
| Avg. by volume 200 nm | Avg. by volume 215 nm |
| Aggregation factor: 200/30 = 7 | Aggregation factor: 215/100 = 2 |

Empty liposomes or liposomes comprising one or more pharmaceutical agent of the present invention are preferably in the size range of 30-3000-nm, more preferably 50-500 nm, more preferably 30-300 nm, more preferably 50-200 nm and more preferably 70-150 nm. An advantage of liposomes smaller or about 100-nm is its ability to penetrate through very narrow blood vessels which is of great significance in diagnostic and treatment.

Any method known in the art can be used to determine the size of the liposome. For example, a Nicomp Submicron Particle Sizer (model 370, Nicomp, Santa Barabara, Calif.) utilizing laser light scattering can be used. Other methods of measuring liposome size include photocorrelation spectroscopy, laser diffraction, low-angle laser light scattering (LALLS), medium-angle laser light scattering (MALLS), light obscuration methods (Coulter method, for example), rheology, or microscopy (light or electron). The preferred average effective particle size depends on factors such as the intended route of administration, formulation, solubility, toxicity and bioavailability of the compound.

Values of Zeta potential in experimentally tested liposomes are provided infra. CDLs without PEGylation −17.9 to −15.5 mV.

With PEGylation (of ghosts-indirect): −13.2 mV. With PEGylation (of CDls-direct): −10.2 mV.

Thus, liposomes of the present invention are characterized by a zeta potential of −20 to −15 mV without PEGylation and −15 to −10 mV with PEGylation.

As mentioned, liposomes of the present invention are advantageously used in the clinic.

Thus, according to an aspect of the invention there is provided a method of delivering a pharmaceutical agent, the method comprising administering to a subject in need thereof the above-describe liposome, wherein the pharmaceutical agent is enclosed therein or adsorbed thereon, thereby delivering the pharmaceutical agent.

According to an embodiment, the cells are target cells and the liposomes contain a targeting moiety, either chemically conjugated, heterologously added, as described above, or natively presented in the membranes from which the liposome is comprised (e.g., as in MSCs, which migrate to tumor cells).

The cell source for the liposomes may be autologous or non-autologous (e.g., allogeneic, xenogeneic) to the subject.

The "target cell" referred to herein is a cell or a cluster of cells (of homogenous or heterogeneous population) and/or tissue to which a substance is to be delivered by using the liposome. Examples thereof include cancer cells, vascular endothelial cells of angiogenic cancer tissues, cancer stem cells, interstitial cells of cancer tissues, cells affected by genetic abnormality, cells infected by a pathogen and the like. The "target molecule" may be any molecule presented the surface of the target cells or cells adjacent to the target cells. Another form of the target molecule includes molecules which are released from cells. Examples thereof includes extracellular matrix components, secretions or architectures of cancer cells or interstitial cells of cancer tissues, and specific examples thereof include tumor markers, structures between cells and the like.

Delivering can be for diagnostic reasons (e.g., the liposome includes a diagnostic agent) or for treating (i.e., as a drug delivery tool, delivering a therapeutic agent).

The liposomes may be administered to the subject per se, or as part of a pharmaceutical composition.

As used herein a "pharmaceutical composition" refers to a preparation of one or more of the active ingredients described herein with other chemical components such as physiologically suitable carriers and excipients. The purpose of the pharmaceutical composition is to facilitate administration of the active ingredients to the subject.

Herein the term "active ingredient" refers to the therapeutic agent (with or without the liposome) accountable for the biological effect. It is to be appreciated that the liposome per se may have immunomodulatory function such as when prepared from membranes of MSCs or other immunomodulatory cells (e.g., immune B and T lymphocytes etc.). It is also to be appreciated that the liposome per se may have a cytoxoic effect on the target cells as due to membrane fusion with target cells and consequent disruption to cell membrane, cytoskeleton and functions. In such a case measures are taken to include a targeting moiety such that the cytotoxic effect becomes specific.

Hereinafter, the phrases "physiologically acceptable carrier" and "pharmaceutically acceptable carrier" which may be interchangeably used refer to a carrier or a diluent that does not cause significant irritation to the subject and does not abrogate the biological activity and properties of the administered active ingredients. An adjuvant is included under these phrases.

Herein, the term "excipient" refers to an inert substance added to the pharmaceutical composition to further facilitate administration of an active ingredient of the present invention or to increase shelf-life stability. Examples, without limitation, of excipients include calcium carbonate, calcium phosphate, various sugars and salts and types of starch, cellulose derivatives, gelatin, vegetable oils, EDTA, EGTA, Poly-L-Lysine, polyethyleneimine, Polybrene (hexadimethrine bromide), polyethylene glycols and other poly or single anions. The pharmaceutical composition may advantageously take the form of foam, aerosol or a gel.

Techniques for formulation and administration of drugs may be found in "Remington's Pharmaceutical Sciences," Mack Publishing Co., Easton, Pa., latest edition, which is incorporated herein by reference.

Suitable routes of administration include any of various suitable systemic and/or local routes of administration.

Suitable routes of administration may, for example, include the inhalation, oral, buccal, rectal, transmucosal, topical, transdermal, intradermal, transnasal, intestinal and/or parenteral routes; the intramuscular, subcutaneous and/or intramedullary injection routes; the intrathecal, direct intraventricular, intravenous, intraperitoneal, intranasal, and/or intraocular injection routes, Catheterization with or without angio balloons; and/or the route of direct injection into a tissue region of the subject.

The pharmaceutical composition may be manufactured by processes well known in the art, e.g., by means of conventional mixing, dissolving, granulating, dragee-making, levigating, emulsifying, encapsulating, entrapping or lyophilizing processes.

Pharmaceutical compositions for use in accordance with the present invention thus may be formulated in conventional manner using one or more physiologically acceptable carriers comprising excipients and auxiliaries, which facilitate processing of the active ingredients into preparations which, can be used pharmaceutically. Proper formulation is dependent upon the route of administration chosen.

For injection, the active ingredients of the pharmaceutical composition may be formulated in aqueous solutions, preferably in physiologically compatible buffers such as Hank's solution, Ringer's solution, or physiological salt buffer.

For transmucosal administration, penetrants appropriate to the barrier to be permeated are used in the formulation. Such penetrants are generally known in the art.

For oral administration, the pharmaceutical composition can be formulated readily by combining the active ingredients with pharmaceutically acceptable carriers well known in the art. Such carriers enable the pharmaceutical composition to be formulated as tablets, pills, dragees, capsules, liquids, gels, syrups, slurries, suspensions, and the like, for oral ingestion by a patient. Pharmacological preparations for oral use can be made using a solid excipient, optionally grinding the resulting mixture, and processing the mixture of granules, after adding suitable auxiliaries if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carbomethylcellulose; and/or physiologically acceptable polymers such as polyvinylpyrrolidone (PVP). If desired, disintegrating agents may be added, such as cross-linked polyvinyl pyrrolidone, agar, or alginic acid or a salt thereof such as sodium alginate.

Dragee cores are provided with suitable coatings. For this purpose, concentrated sugar solutions may be used which may optionally contain gum arabic, talc, polyvinyl pyrrolidone, carbopol gel, polyethylene glycol, titanium dioxide, lacquer solutions and suitable organic solvents or solvent mixtures. Dyestuffs or pigments may be added to the tablets or dragee coatings for identification or to characterize different combinations of active ingredient doses.

Pharmaceutical compositions which can be used orally include push-fit capsules made of gelatin as well as soft, sealed capsules made of gelatin and a plasticizer, such as glycerol or sorbitol. The push-fit capsules may contain the active ingredients in admixture with filler such as lactose, binders such as starches, lubricants such as talc or magnesium stearate and, optionally, stabilizers. In soft capsules, the active ingredients may be dissolved or suspended in suitable liquids, such as fatty oils, liquid paraffin, or liquid polyethylene glycols. In addition, stabilizers may be added. All formulations for oral administration should be in dosages suitable for the chosen route of administration.

For buccal administration, the compositions may take the form of tablets or lozenges formulated in conventional manner.

For administration via the inhalation route, the active ingredients for use according to the present invention can be delivered in the form of an aerosol/spray presentation from a pressurized pack or a nebulizer with the use of a suitable propellant, e.g., a fluorochlorohydrocarbon such as dichlorodifluoromethane, trichlorofluoromethane, dichloro-tetrafluoroethane; carbon dioxide; or a volatile hydrocarbon such as butane, propane, isobutane, or mixtures thereof. In the case of a pressurized aerosol, the dosage unit may be determined by providing a valve to deliver a metered amount. Capsules and cartridges of, e.g., gelatin for use in a dispenser may be formulated containing a powder mix of the active ingredients and a suitable powder base such as lactose or starch.

The pharmaceutical composition may be formulated for parenteral administration, e.g., by bolus injection or continuous infusion. Formulations for injection may be presented in unit dosage form, e.g., in ampoules or in multidose containers with optionally, an added preservative. The compositions may be suspensions, solutions or emulsions in oily or aqueous vehicles, and may contain formulatory agents such as suspending, stabilizing and/or dispersing agents.

A pharmaceutical composition for parenteral administration may include an aqueous solution of the active ingredients in water-soluble form. Additionally, suspensions of the active ingredients may be prepared as appropriate oily or water based injection suspensions. Suitable lipophilic solvents or vehicles include fatty oils such as sesame oil, or synthetic fatty acids esters such as ethyl oleate, triglycerides or liposomes. Aqueous injection suspensions may contain substances, which increase the viscosity of the suspension, such as sodium carboxymethyl cellulose, sorbitol or dextran. Optionally, the suspension may also contain suitable stabilizers or agents which increase the solubility of the active ingredients to allow for the preparation of highly concentrated solutions.

Alternatively, the active ingredients may be in powder form for constitution with a suitable vehicle, e.g., sterile, pyrogen-free water based solution, before use.

The pharmaceutical composition may also be formulated in rectal compositions such as suppositories or retention enemas, using, e.g., conventional suppository bases such as cocoa butter or other glycerides.

The pharmaceutical composition should contain the active ingredients in an amount effective to achieve disease treatment.

Determination of a therapeutically effective amount is well within the capability of those skilled in the art, especially in light of the detailed disclosure provided herein.

For any preparation used in the methods of the invention, the therapeutically effective amount or dose can be estimated initially from in vitro and cell culture and in vivo assays. For example, a dose can be formulated in animal models to achieve a desired concentration or titer. Such information can be used to more accurately determine useful doses in humans.

Toxicity and therapeutic efficacy of the active ingredients described herein can be determined by standard pharmaceutical procedures in vitro, in cell cultures or experimental animals. The data obtained from these in vitro and cell culture assays and animal studies can be used in formulating a range of dosage for use in human. The dosage may vary depending upon the dosage form employed and the route of administration utilized. The exact formulation, route of administration and dosage can be chosen by the individual physician in view of the patient's condition. (See e.g., Fingl, et al., 1975, in "The Pharmacological Basis of Therapeutics", Ch. 1 p. 1).

Dosage amount and interval may be adjusted individually to provide plasma or brain levels of the active ingredients which are sufficient to achieve the desired therapeutic effect (minimal effective concentration, MEC). The MEC will vary for each preparation, but can be estimated from in vitro data. Dosages necessary to achieve the MEC will depend on individual characteristics and route of administration. Detection assays can be used to determine plasma concentrations.

Depending on the severity and responsiveness of the condition to be treated, dosing can be of a single or a plurality of administrations, with course of treatment lasting from several days to several weeks or until cure is effected or diminution of the disease state is achieved.

The amount of the composition to be administered will be dependent on the subject being treated, the severity of the affliction, the manner of administration, the judgment of the prescribing physician, etc.

Compositions of the present invention may, if desired, be presented in a pack or dispenser device, such as an FDA approved kit, which may contain one or more unit dosage forms containing the active ingredients. The pack may, for example, comprise metal or plastic foil, such as a blister pack. The pack or dispenser device may be accompanied by instructions for administration. The pack or dispenser may also be accommodated by a notice associated with the container in a form prescribed by a governmental agency regulating the manufacture, use or sale of pharmaceuticals, which notice is reflective of approval by the agency of the form of the compositions or human or veterinary administration. Such notice, for example, may be of labeling approved by the U.S. Food and Drug Administration for prescription drugs or of an approved product insert.

As used herein the term "about" refers to ±10%.

The terms "comprises", "comprising", "includes", "including", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals there between.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

As used herein, the term "treating" includes abrogating, substantially inhibiting, slowing or reversing the progression of a condition, substantially ameliorating clinical or aesthetical symptoms of a condition or substantially preventing the appearance of clinical or aesthetical symptoms of a condition.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Various embodiments and aspects of the present invention as delineated hereinabove and as claimed in the claims section below find experimental support in the following examples.

EXAMPLES

Reference is now made to the following examples, which together with the above descriptions illustrate some embodiments of the invention in a non limiting fashion.

Generally, the nomenclature used herein and the laboratory procedures utilized in the present invention include molecular, biochemical, microbiological and recombinant DNA techniques. Such techniques are thoroughly explained in the literature. See, for example, "Molecular Cloning: A laboratory Manual" Sambrook et al., (1989); "Current Protocols in Molecular Biology" Volumes I-III Ausubel, R. M., ed. (1994); Ausubel et al., "Current Protocols in Molecular Biology", John Wiley and Sons, Baltimore, Md. (1989); Perbal, "A Practical Guide to Molecular Cloning", John Wiley & Sons, New York (1988); Watson et al., "Recombinant DNA", Scientific American Books, New York; Birren et al. (eds) "Genome Analysis: A Laboratory Manual Series", Vols. 1-4, Cold Spring Harbor Laboratory Press, New York (1998); methodologies as set forth in U.S. Pat. Nos. 4,666,828; 4,683,202; 4,801,531; 5,192,659 and 5,272,057; "Cell Biology: A Laboratory Handbook", Volumes I-III Cellis, J. E., ed. (1994); "Current Protocols in Immunology" Volumes I-III Coligan J. E., ed. (1994); Stites et al. (eds), "Basic and Clinical Immunology" (8th Edition), Appleton & Lange, Norwalk, Conn. (1994); Mishell and Shiigi (eds), "Selected Methods in Cellular Immunology", W. H. Freeman and Co., New York (1980); available immunoassays are extensively described in the patent and scientific literature, see, for example, U.S. Pat. Nos. 3,791,932; 3,839,153; 3,850,752; 3,850,578; 3,853,987; 3,867,517; 3,879,262; 3,901,654; 3,935,074; 3,984,533; 3,996,345; 4,034,074; 4,098,876; 4,879,219; 5,011,771 and 5,281,521; "Oligonucleotide Synthesis" Gait, M. J., ed. (1984); "Nucleic Acid Hybridization" Hames, B. D., and Higgins S. J., eds. (1985); "Transcription and Translation" Hames, B. D., and Higgins S. J., Eds. (1984); "Animal Cell Culture" Freshney, R. I., ed. (1986); "Immobilized Cells and Enzymes" IRL Press, (1986); "A Practical Guide to Molecular Cloning" Perbal, B., (1984) and "Methods in Enzymology" Vol. 1-317, Academic Press; "PCR Protocols: A Guide To Methods And Applications", Academic Press, San Diego, Calif. (1990); Marshak et al., "Strategies for Protein Purification and Characterization—A Laboratory Course Manual" CSHL Press (1996); all of which are incorporated by reference as if fully set forth herein. Other general references are provided throughout this document. The procedures therein are believed to be well known in the art and are provided for the convenience of the reader. All the information contained therein is incorporated herein by reference.

Example 1

Characterization of MSC Migratory and Targeting Abilities

Human MSCs were purchased from Lonza® (Switzerland) and characterized using Giemsa staining and FACS analysis for human mesenchymal stem cells (hMSCs) typical cell surface markers. As seen from FIGS. 1A-1C the cells appear to be positive for CD90, CD105, CD44, and CD29 and negative for CD133, CD31, CD34 and CD144, as expected for hMSCs.

The migratory abilities of the hMSCs towards cancer cells were tested as well. For these experiments, hMSCs were labeled by a red-fluorescent dye (DiI) while several other cell lines (including a prostate cancer cell-line—PC3) were labeled by a green fluorescent dye (DiO). Labeled cells were drop-wise seeded on tissue culture plates, incubated for 72 hrs and imaged using the Maestro in vivo Imager (FIG. 2). As seen, specific migration of hMSCs towards PC3 cancer cells was demonstrated while "avoiding" interaction with other cell-lines (BHK, Cf2Th, and COS-7). Additional experiments were conducted to validate the targeting abilities of conditioned hMSCs to breast cancer cell-line MCF7. For that, human hMSCs were cultured with or without MCF7-derived conditioning media, labeled with DiI (red) and co-cultured with MCF7 cells labeled with DiO (green). Following 2 hr incubation, cultures were washed and the coverage areas of each cell type and cell overlay (yellow) were determined using fluorescent microscopy image analysis. Assuming that the overlay of DiI and DiO is a consequence of physical interaction between the two cell types, the percent of overlay may represent the amount of membranal interactions between the two cell types. As can be seen from FIG. 3, the incubation of conditioned hMSCs with MCF7 cells resulted in 7% overlay, out of the total cell coverage area, compared to no overlay when using unconditioned hMSCs ($p<0.001$). This apparent targeting evidently differs from the migration described in FIG. 2 as it is mainly governed by membranal interactions between the hMSCs and the cancerous cells and not based on the migratory abilities of hMSCs that is largely mediated by soluble factors.

Example 2

Characterization of Cell Derived Liposomes Prepared from hMSCs

Cell Derived Liposome Preparation

About $10^7$ Cells were harvested and washed with PBS. Cells were then hypotonically treated by re-suspension in ice cold Tris-magnesium (TM buffer, 0.01 M Tris, 0.001 M $MgCl_2$) pH 7.4 for 15 min at 4° C. Following hypotonic treatment, the cells were homogenized by rotor-stator mechanical homogenizer (IKA®, Taquara, RJ, Brazil) for 1 min at 22,000 rpm and turned into ghosts (95% ruptured cell membranes as confirmed by phase-contrast microscopy). For stabilizing the ghosts' suspension, 60% (w/w) sucrose solution was immediately added to the suspension to make a final concentration of 0.25M or 10% by volume. Ghosts were then centrifuged at 3000 rpm for 15 min at 4° C. The supernatant was discarded and the pellet of ghosts was then washed twice with 0.25 M sucrose in TM-buffer pH 7.4, by repeated suspension and centrifugation at 3,000 rpm for 15 min at 4° C. In order to create sonicated ghosts, the re-suspended pellet was then sonicated for 5 seconds at 27% amplitude using VibraCell VCX750 (Sonics & Materials Inc., Newtown, Conn.) and centrifuged at 3,000 rpm for 15 min at 4° C. The pellet of sonicated ghosts was then washed twice again with 0.25 M sucrose in TM-buffer pH 8.6, by repeated suspension and centrifugation at 3,000 rpm for 15 min at 4° C. For the formation of unilamellar liposomes, the resuspeded pellet of sonicated ghosts was manually extruded by 21 successive passages trough polycarbonate membranes with pore sizes of 0.4 µm and 0.1 µm (Osmonics Inc., Minnesota USA). The extruded liposomes were then centrifuged for 45 min at 150,000 g at 4° C. The supernatant was discarded and the resulting liposomes pellet was resuspended with TM buffer pH 8.6.

Cell Derived Liposomes Surface Protein PEGylation (According to the Method of Croyle, M. A. Et al., 2004)—

About $10^7$ Cells were harvested and washed with PBS. Cells were then hypotonically treated by re-suspension in ice cold Tris-magnesium (TM buffer, 0.01 M Tris, 0.001 M $MgCl_2$) pH 7.4 for 15 min at 4° C. Following hypotonic treatment, the cells were homogenized by rotor-stator mechanical homogenizer (IKA®, Taquara, RJ, Brazil) for 1 min at 22,000 rpm and turned into ghosts (95% ruptured cell membranes as confirmed by phase-contrast microscopy). For stabilizing the ghosts' suspension, 60% (w/w) sucrose solution was immediately added to the suspension to make a final concentration of 0.25M or 10% by volume. Ghosts were then centrifuged at 3000 rpm for 15 min at 4° C. The supernatant was discarded and the pellet of ghosts was then washed twice with 0.25 M sucrose in TM-buffer pH 7.4, by repeated suspension and centrifugation at 3,000 rpm for 15 min at 4° C. In order to create sonicated ghosts, the re-suspended pellet was then sonicated for 5 seconds at 27% amplitude using VibraCell VCX750 (Sonics & Materials Inc., Newtown, Conn.) and centrifuged at 3,000 rpm for 15 min at 4° C. The pellet of sonicated ghosts was then washed twice again with 0.25 M sucrose in TM-buffer pH 8.6, by repeated suspension and centrifugation at 3,000 rpm for 15 min at 4° C. For the formation of unilamellar liposomes, the resuspeded pellet of sonicated ghosts was manually extruded by 21 successive passages trough polycarbonate membranes with pore sizes of 0.4 µm and 0.1 µm (Osmonics Inc., Minnesota USA). The extruded liposomes were then centrifuged for 45 min at 150,000 g at 4° C. The supernatant was discarded and the resulting liposomes pellet was resuspended with TM buffer pH 8.6.

The protein content on the liposome's surface was determined using the Bradford protein assay, referring to bovine serum albumin (BSA) as standard. Succinimidyl succinate activated Monomethoxy-PEG was obtained from Sigma Chemicals (St. Louis, Mo.) and was added to the resuspended liposomes at a 10:1 ratio relative to the liposomes' protein content as previously determined by the Bradford assay. For example, 10 µg of Monomethoxy-PEG were added for each 1 µg of protein. The conjugation reaction between the Monomethoxy-PEG and the liposomes was performed at 25° C. with gentle agitation. The reaction was stopped by the addition of 10× L-lysine (Sigma Chemicals) with respect to the amount of Monomethoxy-PEG added. Un-reacted free PEG, excess lysine, and reaction byproducts were eliminated by buffer exchange over a Micro-Bio Spin P-30 chromatography column (Bio-Rad) equilibrated with TM buffer pH 8.6.

CDL FACS Analysis. Materials—

Coupling Buffer—used for pre-washing and conjugating Dynabeads M-280 to the liposomes. The buffer was composed of 0.1M Na-phosphate buffer pH 7.4, 2.62 g $NaH_2PO_4 \times H_2O$ (MW 137.99) and 14.42 g $Na2HPO4 \times 2H2O$ (MW 177.99) dissolved in distilled water and adjusted to 1 liter. Washing, blocking and Storage Buffer—PBS pH 7.4 with 0.1% (w/v) BSA: Add 0.88 g NaCl (MW 58.4) and 0.1% (w/v) BSA to 80 ml 0.01M Na-phosphate pH 7.4. Mix thoroughly and adjust volume to 100 ml with 0.01M Na-phosphate pH 7.4.

Method:

Liposomes were created form $2 \times 10^7$ hMSCs as previously described. Tosyl-activated paramagnetic Dynabeads® M-280 (invitrogen) were used as they were able to non-specifically and covalently bind any protein and/or liposomes conjugated with proteins and to be later analyzed by flow-cytometry. Using magnetic separation device (MACS, Dynal™ Magnetic Particle Separator—Invitrogen), the beads were washed with the coupling buffer. To increase their ability to conjugate proteins, the beads were then further washed with 3M ammonium sulfate added to the coupling Buffer. later, 4 samples were prepared containing $10^7$ beads each: Beads only, beads with liposomes, beads with liposomes to be labeled with secondary antibody (isotype control) and beads conjugated with liposomes to be labeled with primary and secondary antibody (test sample). About $5 \times 10^6$ cell equivalent liposomes were added to each sample. Liposomes and beads were then incubated for at least 12 hr at 4° C. After attachment, samples were re-suspended in the washing\blocking buffer. Each sample was suspended in total volume of 200 μl. First, mouse MABs anti-human CD29, CD44, CD90 or CD105 were added to the appropriate samples in a ratio 1:100. Samples were incubated for 30 min in RT. Next, samples were washed twice using the magnetic device. Then secondary ABs (FITC-conjugated goat anti mouse) were added and the samples were incubated for 30 min at RT in the dark. All antibodies, primary and secondary, were purchased from BD—Becton, Dickinson and Company. Following washing of the samples as mentioned before, the samples were run and analyzed using FACSCalibur and CellQuest Pro (BD).

Results

PEGylated Cell-Derived Liposomes (PEG-CDLs) are expected to be protected from opsonization and degradation, thus, having stealth properties and longer circulation time in vivo. Also, PEGylation may reduce the risk of non-specific binding and fusion of liposomes as with non-target cells[17-19].

Cryo-TEM imaging of the CDLs demonstrated that the PEGylation had no apparent effect on the desirable small unilamellar morphology of the CDLs (FIGS. 4A-4B). However, the PEGylated liposomes (FIG. 4A) seemed more dispersed and less coagulated than the un-PEGylated liposomes (FIG. 4B), that were imaged at the same concentration and under the same conditions. Apparently, not only that the PEGylation does not damage liposomes' morphology but it may also improve their dispersion and stability. The size and size distribution of the CDLs were further analyzed using number and volume weighing DLS analysis (Dynamic Light Scattering, Malvern Nanosize). While number-weight DLS analysis (FIG. 5A) demonstrated an increase in liposomes' size following PEGylation (from ~30 nm to ~100 nm), volume-weight DLS analysis (FIG. 5B) demonstrated that the addition of PEG had a homogenizing effect on the system, exhibiting a significant reduction in the liposomes' size distribution. Evidently, the addition of PEG groups stabilized the system and prevented aggregation even though the Zeta-potential decreased from −17.9 mV to −10.2 mV (FIG. 5C).

Finally, the expression of MSC-specific surface markers, on the surface of hMSCs derived liposomes, was validated by FACS analysis (FIG. 6). As seen, the CDLs retained their cytoplasmatic membrane symmetry and the expression of correctly oriented typical hMSCs surface markers (i.e., CD44, CD29, CD90 and CD105).

Example 3

Binding and Specific Targeting of Cancerous Cell-Lines by CDLs

Confocal microscopy imaging and flow cytometry analysis were used to determine the binding of fluorescently labeled CDLs prepared from hMSCs to prostate cancer cells (PC3). As can be seen from FIG. 7A, most vesicles favored cell binding. In addition, the vesicles were detected inside and fused with the cell membranes (FIG. 7A).

Flow cytometry analysis demonstrates that most cells bind the vesicles (FIG. 8A) in a concentration-dependent manner (FIG. 8A), thus allowing to determine the extent of liposomal binding according to the cells' mean fluorescence intensity.

To test the specific targeting of cancerous cell-lines, DiI-labeled CDLs were prepared from hMSCs, which were previously incubated for 24 hrs with condition media derived from a prostate cancer cell-line (PC3) and from a non-human cell-line (BHK). The resulting "conditioned" CDLs, as well as CDLs prepared from unconditioned hMSCs (control), were incubated with PC3 and BHK cells for 15 min, 1 hr and 3 hrs. Following incubation, cells were washed, harvested and analyzed by flow cytometry (FIG. 9).

The specificity index for every experiment, given a certain conditioning media (NO CM, BHK-derived and PC3-derived) and incubation time (15 min, 1 hr and 3 hrs), was calculated according to the following equation:

$$\text{(Specificity index)} = \frac{\dfrac{\% \ PC3 \ \text{cells in the marker following incubation with } CDLs}{\% \ PC3 \ \text{cells in the marker withot } CDLs}}{\dfrac{\% \ BHK \ \text{cells in the marker following incubation with } CDLs}{\% \ BHK \ \text{cells in the marker withot } CDLs}}$$

The specificity index results, summarized in Table 3 below, not only illustrates that the system exhibits specificity towards cancerous cells but that this specificity, as excepted, decreases with incubation time. In addition, the specificity index values show that the system's specific affinity towards cancer cells can be largely affected by subjecting the cells to various conditioning media prior to CDLs preparation.

TABLE 3

Specificity index of CDLs binding to prostate cancer PC3 cell-line

| hMSCs Conditioning media | CDL incubation time with PC3 and BHK cells | | |
|---|---|---|---|
| | 15 min | 1 hr | 3 hr |
| No CM | 1.91 | 1.50 | 1.25 |
| BHK derived | 3.45 | 3.43 | 1.10 |
| PC3 derived | 2.92 | 2.31 | 1.50 |

Example 4

Protein Entrapment within CDLs sTRAIL Production

Mediums and Buffers—

1 L 2YT medium was prepared from 16 gr Bacto™ Tryptone (BD number 211705), 10 gr Bacto™ Yeast Extract (DIFCO number 212750) and 5 gr NaCl (Chemically Pure). Medium used for culturing in Petri dished contained 16 gr Agar Granulated (DIFCO number 214530) on top of the above components. The medium was autoclaved for sterility. PBSX10 was prepared from 2 gr KCl, 2.4 gr $KH_2PO_4$, 14.4 gr $Na_2HPO_4.7H_2O$ and 80 gr NaCl. Volume was adjusted to 1 L with DDW and the buffer was filter sterilized through 0.2 µm filter.

Plasmids, DNA, Bacteria and Antibiotics—

GST-sTRAIL coding DNA was kindly supplied by Dr. Stanley Lipkowitz, Bethesda, Md. in pGEX-2TK plasmid introduced into E. coli BL21 using Ampicillin 100 µg/ml as a selection agent. Ampicillin stock was prepared from ampicillin Sodium Salt (Sigma number A9518) dissolved in Ultra Pure DDW (UP-water) to a final concentration of 100 mg/ml and filtered through 0.2 µm filters.

Additional Materials:

Ethyl Alcohol 99% Dehydrated (FRUTAROM number 2355516400); D(+)GLUCOSE (Sigma number G5146); IPTG (Ornat Biochemicals number INA-1758-1400); Complete Mini EDTA-Free Protease inhibitor cocktail tablets (Roche Applied Science number 04693159001); DTT—DL-Dithiothereitol solution (Sigma number 43816); GSH BEADS (GE Healthcare); Glutathione Sepharose 4B (10 ml, Danyel Biotech number 17-0756-01); and L-Glutathione-reduced (Sigma number G4251).

Equipment—

Amicon Ultra-15 centrifugal filters (Millipore number UFC901024); and French Press cell disruption system. All solutions were filtered for sterility through a 0.2 µm filters; all procedures up to Day 2 (step 4, pellet of bacteria after IPTG 0/N induction) were carried out in a Sterile Hood.

Swith 1/100 GST-TRAIL glycerol stock (e.g., 400 µl GST-trail glycerol stock in 40 ml medium). The solution was incubated O/N 37° C. in a shaking incubator at 250 RPM.

Day 2

STEP 2: The "starter" culture was spun down at 1000 g for 15 min to remove the antibiotics. The supernatant was discarded and resuspended in 40 ml of fresh 2YT. In a Sterile Hood, the resuspended 40 ml of the O/N preparation from step number 1 was added to 2 L of 2YT in a 4 L flask (alternatively add the resuspended pellet of 20 ml of the O/N preparation from step number 1 to two 2 L flasks each containing 1 L of 2YT). The solution was incubated for 2-3 hours in a 37° C. shaking incubator at 250 RPM. Measures are taken not incubate for more than 3 hours until O.D. is 2.5-3.0 (it is recommended to measure $O.D._{595}$ after 2 hours).

STEP 3: Just before IPTG induction, PBS was added to a final concentration of 0.1× to maintain the pH of the culture. EtOH (99% Dehydrated) was added to a final concentration of 2% (40 ml in 2 L culture) to increase the solubility of the protein. 10 ml/L of 0.5M Glucose was added as a carbon source to a final concentration of 5 mM.

STEP 4: 500 µM IPTG were added to the supplemented culture. The culture was incubated over night in a shaking incubator (250 RPM) at 20-25° C.

Day 3

STEP 5: Bacteria was pelleted at 6,000 g for 10 min and the supernatant was discarded. All bacteria were resuspended in a 50 ml Falcon Tube using 40 ml PBS supplemented with 4 protease inhibitor tablets (Roche Applied Science) 1 tablet per 10 ml PBS.

STEP 6: Cells were lyzed by running the bacteria from step number 5 twice through a French Press cell disruption system. Alternatively, 10 ml aliquots in 50 ml tubes were sonicated on ice at 30% power by 4 bursts of 10 sec each. After Cell disruption, the following was added to each 40 ml of cell lysate: 0.1% Triton-X (40 µl of TritonX100), 1 mM $MgCl_2$ (40 µl of 1M stock $MgCl_2$) and 1 mM DTT (40 µl of 1M stock DTT). The solution was mixed thoroughly and incubated at RT for 15 min on a rocker or shaker.

STEP 7: The bacterial lysate was spun down for 10 min at 16,900 g and 4° C. Supernatants were aspirated and collected in 50 ml tubes.

STEP 8: Binding to GSH (Glutathione—Sepharose 4B Beads)—In a 15 ml Falcon Tube, 3 ml of GSH Beads were washed three times with PBS. Collected supernatant was centrifuged again because of mass bead loss. The washed beads were added to the bacterial cell lysate from step number 7 and incubated with tumbling for 1 hour at 4° C.

STEP 9: The bacterial cell lysate, containing the sepharose beads from step number 8, was spun down at 2000 RPM for 1 min in a MULTI CENTRIFUGE CM 6M ELMI to separate the protein-conjugated beads from the cell-lysate. The supernatant was collected and was centrifuged again to pellet the remaining sepharose beads in the supernatant (that might have not pelleted during the first centrifugation). The pellet from both centrifugations, containing the sTRAIL-conjugated beads, was washed 5 times with 5 ml of PBS supplemented with 0.1% Triton-X100, 150 mM NaCl and 1 proteinase inhibitor tablets per 20 ml PBS.

STEP 10: Elution of GST-sTRAIL—The beads were spun down as before and the supernatant was aspirated. 3 ml of 50 mM Glutathione (pH 8.5) in 10 mM Tris-HCl and 100 mM NaCl were added. Each 3 ml was vortexed for 2 min and the protein was eluted into the supernatant. The supernatant was aspirated as before and the supernatant kept. The procedure of elution was repeated 3-4 times.

STEP 11: The protein was concentrated using Amicon Ultra-15 10K NMWLnumber UFC9010, giving a protein yield of about 5 mg/L culture. sTRAIL was produced at a final concentration of 0.2 mg/ml sTRAIL Entrapment—

About $10^7$ Cells were Harvested and Washed with PBS. Cells were then hypotonically treated by re-suspension in ice cold Tris-magnesium (TM buffer, 0.01 M Tris, 0.001 M $MgCl_2$) pH 7.4 for 15 min at 4° C. Following hypotonic treatment, the cells were homogenized by rotor-stator mechanical homogenizer (IKA®, Taquara, RJ, Brazil) for 1 min at 22,000 rpm and turned into ghosts (95% ruptured cell membranes as confirmed by phase-contrast microscopy).

For stabilizing the ghosts' suspension, 60% (w/w) sucrose solution was immediately added to the suspension to make a final concentration of 0.25M or 10% by volume. Ghosts were then centrifuged at 3000 rpm for 15 min at 4° C. The supernatant was discarded and the pellet of ghosts was then washed twice with 0.25 M sucrose in TM-buffer pH 7.4, by repeated suspension and centrifugation at 3,000 rpm for 15 min at 4° C. In order to create sonicated ghosts, the re-suspended pellet was then sonicated for 5 seconds at 27% amplitude using VibraCell VCX750 (Sonics & Materials Inc., Newtown, Conn.) and centrifuged at 3,000 rpm for 15 min at 4° C. The pellet of sonicated ghosts was then washed twice again with 0.25 M sucrose in TM-buffer pH 8.6, by repeated suspension and centrifugation at 3,000 rpm for 15 min at 4° C. After, sTRAIL was added to the suspended sonicated ghosts (in TM buffer pH 8.6) to a final concentration of 1 µg per 1 ml of ghost suspension. For the formation of unilamellar liposomes containing sTRAIL, the sTRAIL-containing resuspeded pellet of sonicated ghosts was manually extruded by 21 successive passages trough polycarbonate membranes with pore sizes of 0.4 µm and 0.1 µm (Osmonics Inc., Minnesota USA). The extruded liposomes containing sTRAIL were then centrifuged for 45 min at 150,000 g at 4° C. The supernatant containing excess non-encapsulated sTRAIL was discarded and the resulting liposomes pellet was resuspended with TM buffer pH 8.6.

Results

TRAIL—tumor necrosis factor-related apoptosis-inducing agent is a type II transmembrane protein that induces apoptosis in tumor cells of diverse origins, while sparing most normal cells[20-24]. Delivery of both full length and truncated, secreted forms of TRAIL (sTRAIL) were shown to induce apoptosis in a variety of cancer cells both in culture and in vivo[25, 26]. Our preliminary experiments with sTRAIL included its production and passive encapsulation within hMSCs CDLs at a final concentration of 1 µg/ml. Cryo-TEM imaging of the resulting sTRAIL-containing CDLs (FIG. 10A left pane), compared to empty CDLs (FIG. 10B, left pane) prepared and imaged under the same conditions, demonstrates the accumulation of 14-20 nm protein micelles within the CDLs. The sTRAIL micelles are even more clearly visible after digitally re-coloring the images from grey-scale to black-and-white (FIGS. 10A and 10B, right panel).

Example 5

Preparation of "Hybrid CDLs" by Fusion with Other Liposomes

Various molecules (e.g., proteins, lipids, additives and even encapsulates) can be introduced, conjugated or attached onto the surface of the CDLs by means of fusion between the CDLs and other liposomes (synthetic or cell-derive), thus creating—"Hybrid CDLs". For example, a liposomal formulation made from synthetic well characterized lipids may be conjugated with a protein on its surface or may contain a desirable encapsulate. Then, by means of induced membrane fusion between the said synthetic liposomes and CDLs a hybrid CDL may be formed. These hybrid CDLs contain both lipids and proteins from the cell-membrane they derive from and the lipids and proteins that were originally formulated on the fused synthetic liposomes. Such introduction of 'non-native' materials onto the Hybrid CDLs may be used to attach or conjugate any molecule or moieties related, but not limited to, liposomal targeting, therapeutic effect, diagnostic effect, stealth-rendering properties etc. Such fusion may be also used to change the biochemical or chemophysical properties of the CDLs membranes by introduction of synthetic lipids, additives (e.g., cholesterol, ceramides) etc. Such fusion may be also used to increase the encapsulation efficiency in the said CDLs. Since encapsulation in CDLs is mainly limited to passive encapsulation, fusion with synthetic liposomes that were actively loaded with high concentration of encapsulates may significantly improve the CDLs' encapsulation efficiency.

Methods for preparation of synthetic liposomes are well known in the art and mainly include hydration of dehydrated lipids to form lamellar structures and consequent homogenization of those lamellar structures to create liposomes. Synthetic liposomes of the said application can be produced by any method known in the art including, but not limited to, solvent evaporation, solvent replacement, detergent dialysis, extrusion, sonication, freeze-drying, reverse phase evaporation, ethanol/ether injection, agitation and/or any other form of mechanical homogenization. Liposomes can be prepared from a variety of synthetic and naturally derived lipids and may or may not contain additional additives (e.g., cholesterol, ceramides etc.). Methods for active encapsulation of matter in such synthetic liposomes, which are mainly based on membrane pH gradient or active transporters, are also well known in the art and may be used to create synthetic liposomes with high encapsulation efficiency.

Fusion between CDLs and other liposomes to create "Hybrid CDLs" can be readily and easily accomplished by adding short chain free PEG (~200-500 Da) to the liposomes. The mechanism of PEG-induced vesicle fusion is believed to be related to the reduction of water activity and the dehydration of the lipid headgroups which consequently leads to vesicle coagulation and fusion. Fusion can also be artificially induced through electroporation in a process known as electrofusion. It is believed that this phenomenon results from the energetically active edges formed during electroporation, which can act as the local defect point to nucleate stalk growth between two bilayers. Fusion can also be achieved by addition of detergents (usually under 2%) to the liposomal mixture (e.g., Cymal-S™, 1-S-Octyl Beta-D-thioglucopyranoside etc.), incubation with mild agitation and consequent detergent dialysis.

Example 6

Proteomics Analysis of hMSCc Ghost and Derived CDLs

Method

Proteomics analysis was conducted on 4 samples containing ghost cells and CDLs derived from hMSCc that were either conditioned or unconditioned by a medium derived from a prostate cancer cell-line (PC3). For the production of conditioned ghosts and CDLs, hMSCs were incubated for 24 prior to harvesting in medium composed of 50% conditioning media derived from PC3 cells. Cells were then harvested and sonicated ghosts and CDLs were prepared thereof by the method previously described. Sonicated ghosts from conditioned and unconditioned hMSCs ($10^6$ cells) were resuspended for analysis in 1 ml TM-buffer, pH 7.4. Cell-derived liposomes derived from $7 \times 10^6$ conditioned and unconditioned hMSCc were resuspended in 50 µL TM buffer, pH 8.6.

The samples were sent for proteomics analysis at the proteomics center of the TECHNION—Israel Institute of Technology. Briefly, the samples were digested by Trypsin and the resulting peptides were analyzed by LC-MS/MS. Peptide mix was fractionated by HPLC and electro-sprayed onto an ion-trap mass spectrometer (Orbitrap™). Mass spectrometry was performed in order to analyze the peptides' mass to charge ratio spectra and to determine the proteins' mass. For additional analysis and identification, the peptides were further fragmented by collision induced dissociation (CID) and analyzed again. The peptides were identified by Sequest 3.31 software against the human part of the uniprot database. All protein results are given as Uniport Accession Numbers. The following values were determined for each protein/accession number:

MW—Molecular weight
$P_{pro}$—The probability of finding a match as good as or better than the observed match by chance. The value displayed for the protein is the probability of the best peptide match (the peptide with the lowest score).
Pep Count—The total number of identified peptides.
Mean—The Average of the peak areas of top 3 identified peptides per protein.
Mean.SE—Mean standard error.
Med—Median of the peak area of all identified peptides per protein
MedErr—Median absolute deviation.
Protein Name.

Results

The hundreds of proteins that were identified on one or more of the four samples can be divided into 4 distinct groups:

1. Proteins that were prevalent in all four samples (Table 7), i.e. conditioned and unconditioned ghosts and CDLs.
2. Proteins that were prevalent in the ghosts or conditioned ghosts but were missing from the CDLs (Table 5). These proteins are probably or mostly the remains of cytoplasmatic matter that was not completely removed from the ghosts.
3. Proteins that were prevalent only on the conditioned ghosts and CDLs (Table 6). These proteins are probably or mostly membarnal proteins which are only expressed after induction or exposure to condition media.
4. Proteins that were prevalent in all samples but CDLs that were produced from unconditioned hMSCs (Table 7). These proteins are probably or mostly membarnal proteins which are expressed in lower levels on unconditioned hMSCs and which are completely depleted on their derived CDLs. Inducing the hMSCs with condition media probably elevates these proteins level to the extent they become more apparent on the conditioned CDLs.

TABLE 4

Proteins prevalent on conditioned and unconditioned ghosts and CDLs.

| Uniport Accession Number | MW | Fold expression on conditioned CDLs relative to unconditioned CDLS | Protein name |
|---|---|---|---|
| P04179 | 24706.6 | 30 | Moesin |
| P62899 | 14453.9 | 26 | Myosin regulatory light chain 12A |
| P09622 | 54143.1 | 26 | Sodium/potassium-transporting ATPase subunit alpha-1 |
| P02545 | 74094.8 | 24 | 40S ribosomal protein S28 |
| P05023 | 112824.1 | 14 | Integrin beta-1 |
| P11142 | 70854.4 | 14 | Cathepsin D |
| P62701 | 29579.1 | 12 | Sulfide:quinone oxidoreductase |
| P07602 | 58073.9 | 12 | Histone H4 |
| P21589 | 63327.6 | 11 | Major vault protein |
| P27797 | 48111.9 | 10 | Keratin |
| O75396 | 24724.8 | 10 | Elongation factor 2 |
| P13674 | 61011.1 | 10 | Erlin-2 |
| P24752 | 45170.7 | 9 | 60S ribosomal protein L4 |
| P30044 | 22012.5 | 9 | 60S ribosomal protein L18a |
| P51659 | 79636.4 | 9 | 40S ribosomal protein S21 |
| P61604 | 10924.9 | 8 | Actin |
| P17301 | 129213.8 | 8 | Acetyl-CoA acetyltransferase |
| P38117 | 27826.2 | 8 | Leucine-rich PPR motif-containing protein |
| P10809 | 61016.5 | 8 | Ras-related protein Rab-7a |
| P14314 | 59387.9 | 7 | Dolichyl-diphosphooligosaccharide--protein glycosyltransferase subunit 2 |
| P62736 | 41981.8 | 7 | 60S ribosomal protein L14 |
| Q96D15 | 37470 | 7 | Voltage-dependent anion-selective channel protein 3 |
| P62241 | 24190.2 | 7 | Annexin A4 |
| Q9Y2Q3 | 25480.3 | 7 | Dolichyl-diphosphooligosaccharide--protein glycosyltransferase subunit 1 |
| P02786 | 84818 | 7 | Pyruvate kinase isozymes M1/M2 |
| P38646 | 73634.8 | 7 | 40S ribosomal protein S19 |
| P62829 | 14856.1 | 7 | Annexin A2 |
| Q9H4B7 | 50294.6 | 7 | Reticulocalbin-3 |
| P40926 | 35480.7 | 7 | Peroxiredoxin-1 |
| P08648 | 114464.9 | 7 | Malate dehydrogenase |
| P07237 | 57080.8 | 7 | Prenylcysteine oxidase 1 |
| Q70UQ0 | 39285 | 7 | 40S ribosomal protein S4 |
| Q9NZM1 | 234558.8 | 7 | Proactivator polypeptide |
| Q07020 | 21621.1 | 7 | Heat shock cognate 71 kDa protein |
| P30040 | 28975.2 | 6 | Integrin alpha-V |
| Q09666 | 628705.2 | 6 | Annexin A11 |
| Q32P28 | 83341.2 | 6 | 60S ribosomal protein L7a |
| Q15155 | 134267.4 | 6 | Serine hydroxymethyltransferase |

TABLE 4-continued

Proteins prevalent on conditioned and unconditioned ghosts and CDLs.

| Uniport Accession Number | MW | Fold expression on conditioned CDLs relative to unconditioned CDLS | Protein name |
| --- | --- | --- | --- |
| P04040 | 59718.9 | 6 | Tubulin alpha-1B chain |
| P30048 | 27675.2 | 6 | 60S ribosomal protein L26-like 1 |
| P68104 | 50109.2 | 6 | Integrin alpha-2 |
| Q00325 | 40068.8 | 6 | Myoferlin |
| P30443 | 40820.2 | 6 | Trifunctional enzyme subunit beta |
| P06756 | 115964.5 | 6 | Thioredoxin-dependent peroxide reductase |
| Q15149 | 531465.9 | 6 | ATP synthase subunit O |
| P16615 | 114682.7 | 6 | Elongation factor Tu |
| P14625 | 92411.2 | 6 | 60S ribosomal protein L11 |
| P19105 | 19781.5 | 6 | 60S acidic ribosomal protein P0-like |
| P34897 | 55957.8 | 6 | 40S ribosomal protein S3 |
| P45880 | 31546.5 | 6 | Signal recognition particle receptor subunit beta |
| O15118 | 142073.5 | 6 | Serpin H1 |
| P62805 | 11360.4 | 6 | Isocitrate dehydrogenase [NADP] |
| Q99536 | 41893.5 | 6 | Endoplasmin |
| P36957 | 48698.6 | 6 | Tubulin beta chain |
| P02751 | 262439.5 | 5 | CD44 antigen |
| P13639 | 95277.1 | 5 | 60S ribosomal protein L30 |
| P49411 | 49510.2 | 5 | 60S ribosomal protein L12 |
| Q00610 | 191491.7 | 5 | Plectin-1 |
| P55072 | 89265.9 | 5 | Aldehyde dehydrogenase X |
| P21281 | 56465 | 5 | ATP synthase subunit alpha |
| Q16698 | 36044.8 | 5 | Collagen alpha-1(I) chain |
| P26038 | 67777.9 | 5 | 40S ribosomal protein S8 |
| P14854 | 10185.7 | 5 | ATP synthase subunit d |
| P50454 | 46411.3 | 5 | Erlin-1 |
| P08670 | 53619.2 | 5 | Vesicle-trafficking protein SEC22b |
| Q13423 | 113822.9 | 5 | Procollagen-lysine |
| P62847 | 15413.4 | 5 | Synaptic vesicle membrane protein VAT-1 homolog |
| P00505 | 47445.3 | 5 | Protein disulfide-isomerase A6 |
| P05556 | 88357 | 5 | Niemann-Pick C1 protein |
| P30837 | 57202.3 | 5 | Annexin A1 |
| P13667 | 72887.1 | 5 | Cytochrome c oxidase subunit 6B1 |
| P06733 | 47139.4 | 5 | Voltage-dependent anion-selective channel protein 2 |
| P68363 | 50119.6 | 5 | 10 kDa heat shock protein |
| Q15084 | 48091.3 | 5 | Heme oxygenase 1 |
| P04844 | 69241.1 | 5 | Lysosome membrane protein 2 |
| P36578 | 47667.5 | 5 | 60S ribosomal protein L22 |
| P11021 | 72288.5 | 5 | Dipeptidyl peptidase 4 |
| O60568 | 84731.7 | 5 | ATP synthase subunit beta |
| P04406 | 36030.4 | 5 | Keratin |
| O95816 | 23757.2 | 5 | Calreticulin |
| Q04837 | 17249 | 5 | 60S acidic ribosomal protein P2 |
| P09601 | 32798 | 5 | Transitional endoplasmic reticulum ATPase |
| Q06830 | 22096.3 | 5 | Lamin-A/C |
| Q9H9B4 | 35596.4 | 5 | Protein disulfide-isomerase A3 |
| P09525 | 35860.1 | 5 | 40S ribosomal protein S5 |
| P16070 | 81503.4 | 5 | Tubulin beta-1 chain |
| P04075 | 39395.3 | 5 | Annexin A5 |
| P14649 | 22749.7 | 5 | Electron transfer flavoprotein subunit beta |
| Q02809 | 83497.5 | 5 | Peptidyl-prolyl cis-trans isomerase B |
| P10606 | 13686.9 | 5 | Collagen alpha-1(VI) chain |
| P48735 | 50876.9 | 5 | Translocon-associated protein subunit delta |
| P07339 | 44523.7 | 5 | Keratin |
| Q9Y6N5 | 49928.9 | 5 | Peroxisomal multifunctional enzyme type 2 |
| Q7KZF4 | 101933.6 | 5 | Prohibitin-2 |
| P50213 | 39566.1 | 5 | Leucine-rich repeat-containing protein 59 |
| Q9UNX3 | 17245.6 | 5 | Prolyl 3-hydroxylase 1 |
| P14618 | 57900.2 | 5 | Lysosome-associated membrane glycoprotein 2 |
| Q96AG4 | 34908.9 | 5 | 40S ribosomal protein S18 |
| P07355 | 38579.8 | 4 | Guanine nucleotide-binding protein G(I)/G(S)/G(T) subunit beta-1 |
| P61803 | 12488.6 | 4 | Dihydrolipoyl dehydrogenase |
| Q13162 | 30520.8 | 4 | 60S ribosomal protein L5 |
| P63220 | 9105.6 | 4 | Guanine nucleotide-binding protein subunit beta-2-like 1 |
| P62263 | 16262.5 | 4 | 60S ribosomal protein L18 |
| Q14108 | 54255.6 | 4 | Histone H2B type 1-B |
| P63244 | 35054.6 | 4 | 5'-nucleotidase |
| P49748 | 70345.5 | 4 | ADP/ATP translocase 2 |
| P55084 | 51261.6 | 4 | Aminopeptidase N |
| P42704 | 157804.6 | 4 | L-lactate dehydrogenase A chain |
| P00338 | 36665.4 | 4 | Voltage-dependent anion-selective channel protein 1 |

TABLE 4-continued

Proteins prevalent on conditioned and unconditioned ghosts and CDLs.

| Uniport Accession Number | MW | Fold expression on conditioned CDLs relative to unconditioned CDLS | Protein name |
| --- | --- | --- | --- |
| Q02543 | 20748.9 | 4 | Glucosidase 2 subunit beta |
| Q13885 | 49875 | 4 | Annexin A6 |
| P30101 | 56746.8 | 4 | ATP synthase subunit delta |
| P35268 | 14777.8 | 4 | Peroxiredoxin-5 |
| Q9P2E9 | 152380 | 4 | Very long-chain specific acyl-CoA dehydrogenase |
| P62424 | 29977 | 4 | Prolow-density lipoprotein receptor-related protein 1 |
| P36543 | 26128.8 | 4 | Inhibitor of nuclear factor kappa-B kinase-interacting protein |
| P62857 | 7836.2 | 4 | 40S ribosomal protein S24 |
| P62753 | 28663 | 4 | Elongation factor 1-alpha 1 |
| Q9UHG3 | 56603.8 | 4 | Aspartate aminotransferase |
| P50914 | 23417 | 4 | 60S ribosomal protein L13 |
| P60174 | 26652.7 | 4 | Adipocyte plasma membrane-associated protein |
| P27487 | 88222.5 | 4 | Fibronectin |
| P62269 | 17707.9 | 4 | Myosin light chain 6B |
| P36542 | 32975.3 | 4 | Transgelin |
| P39656 | 50769 | 4 | Staphylococcal nuclease domain-containing protein 1 |
| Q99623 | 33275.9 | 4 | Sideroflexin-3 |
| P26373 | 24246.5 | 4 | 60S ribosomal protein L31 |
| Q9HDC9 | 46450.9 | 4 | Phosphate carrier protein |
| Q71U36 | 50103.7 | 4 | ADP/ATP translocase 1 |
| P08865 | 32833.4 | 4 | Lysosome-associated membrane glycoprotein 1 |
| P00387 | 34212.7 | 4 | Hexokinase-1 |
| Q9Y5M8 | 29683.8 | 4 | Protein disulfide-isomerase A4 |
| P25705 | 59713.7 | 4 | Catalase |
| P23284 | 23727.5 | 4 | Cytochrome c oxidase subunit 5A |
| P05387 | 11657.9 | 4 | 40S ribosomal protein SA |
| P43307 | 32215.4 | 4 | Isocitrate dehydrogenase [NAD] subunit alpha |
| P49755 | 24960 | 4 | 2 |
| P04083 | 38690 | 4 | Tubulin beta-2C chain |
| P04843 | 68526.9 | 4 | V-type proton ATPase subunit E 1 |
| P08133 | 75825.7 | 4 | 40S ribosomal protein S6 |
| P68371 | 49799 | 4 | V-type proton ATPase catalytic subunit A |
| O75477 | 38901.4 | 4 | Trifunctional enzyme subunit alpha |
| P21796 | 30753.6 | 4 | Ribosome-binding protein 1 |
| P62873 | 37353 | 4 | Vimentin |
| P12235 | 33043.2 | 4 | Protein S100-A11 |
| P20674 | 16751.7 | 4 | Procollagen-lysine |
| Q9BWM7 | 35480.5 | 4 | Mitochondrial inner membrane protein |
| P23396 | 26671.4 | 4 | 60S ribosomal protein L23 |
| P05141 | 32874.2 | 4 | 60 kDa heat shock protein |
| P61247 | 29925.8 | 3 | Alpha-enolase |
| Q16891 | 83626.5 | 3 | Transmembrane emp24 domain-containing protein 9 |
| P51571 | 18986.6 | 3 | Collagen alpha-2(I) chain |
| O75489 | 30222.7 | 3 | Endoplasmic reticulum resident protein 29 |
| P31930 | 52612.5 | 3 | Cytochrome b-c1 complex subunit 1 |
| P48047 | 23262.7 | 3 | NADH dehydrogenase [ubiquinone] iron-sulfur protein 3 |
| P62888 | 12775.7 | 3 | Neuroblast differentiation-associated protein AHNAK |
| P12111 | 343450.3 | 3 | Prohibitin |
| Q8NHW5 | 34342.7 | 3 | 40S ribosomal protein S14 |
| P12109 | 108462 | 3 | V-type proton ATPase subunit B |
| P30050 | 17807.5 | 3 | Triosephosphate isomerase |
| P40939 | 82947 | 3 | Integrin alpha-5 |
| O75947 | 18479.5 | 3 | Fructose-bisphosphate aldolase A |
| P31040 | 72645.4 | 3 | Calnexin |
| P19367 | 102420.2 | 3 | Cytochrome b-c1 complex subunit 2 |
| P30049 | 17479.2 | 3 | Prolyl 4-hydroxylase subunit alpha-1 |
| P46782 | 22862.1 | 3 | Transmembrane emp24 domain-containing protein 10 |
| P39019 | 16050.5 | 3 | Peroxiredoxin-4 |
| Q07065 | 65982.9 | 3 | Stomatin-like protein 2 |
| P35232 | 29785.9 | 3 | BAG family molecular chaperone regulator 2 |
| P62913 | 20239.7 | 3 | Sarcoplasmic/endoplasmic reticulum calcium ATPase 2 |
| P06576 | 56524.7 | 3 | Clathrin heavy chain 1 |
| P51149 | 23474.9 | 3 | Collagen alpha-3(VI) chain |
| P27824 | 67526 | 3 | 60S ribosomal protein L9 |
| P31949 | 11732.8 | 3 | HLA class I histocompatibility antigen |
| P35579 | 226390.6 | 3 | NADH-ubiquinone oxidoreductase 75 kDa subunit |
| P02452 | 138826.8 | 3 | Dolichyl-diphosphooligosaccharide--protein glycosyltransferase 48 kDa subunit |
| Q01995 | 22596.4 | 3 | Dolichyl-diphosphooligosaccharide--protein glycosyltransferase subunit DAD1 |
| Q14764 | 99266.1 | 3 | Transferrin receptor protein 1 |

TABLE 4-continued

Proteins prevalent on conditioned and unconditioned ghosts and CDLs.

| Uniport Accession Number | MW | Fold expression on conditioned CDLs relative to unconditioned CDLS | Protein name |
| --- | --- | --- | --- |
| Q9UJZ1 | 38510.2 | 3 | 40S ribosomal protein S3a |
| P08123 | 129209.8 | 3 | NADH-cytochrome b5 reductase 3 |
| P50995 | 54355.1 | 2 | Sideroflexin-1 |
| P11279 | 44853.9 | 2 | Actin |
| Q9BVK6 | 27260.2 | 2 | Myosin-9 |
| P38606 | 68260.6 | 2 | NAD(P) transhydrogenase |
| P08758 | 35914.4 | 2 | 60S ribosomal protein L7 |
| P28331 | 79416.7 | 2 | CD59 glycoprotein |
| P15144 | 109470.8 | 2 | Cytochrome c oxidase subunit 5B |
| P22695 | 48412.9 | 2 | Glyceraldehyde-3-phosphate dehydrogenase |
| P35908 | 65393.2 | 2 | Glutathione S-transferase kappa 1 |
| P35527 | 62026.7 | 2 | Tubulin alpha-1A chain |
| Q07954 | 504243.2 | 2 | Dihydrolipoyllysine-residue succinyltransferase component of 2-oxoglutarate dehydrogenase complex |
| P33778 | 13941.6 | 2 | Succinate dehydrogenase [ubiquinone] flavoprotein subunit |
| P13645 | 58791.6 | 1 | Cytoskeleton-associated protein 4 |
| P60709 | 41709.7 | 1 | Keratin |
| P46777 | 34340.7 | 1 | Stress-70 protein |
| Q9Y277 | 30639.3 | 1 | Protein disulfide-isomerase |
| P32969 | 21849.8 | 1 | ATP synthase subunit gamma |
| P18124 | 29207.2 | 1 | Translocon-associated protein subunit alpha |
| O94905 | 37815.5 | 1 | Single-stranded DNA-binding protein |
| P13987 | 14167.8 | 1 | 78 kDa glucose-regulated protein |
| P07437 | 49639 | 1 | Nodal modulator 1 |
| P13473 | 44932.3 | 1 | Superoxide dismutase [Mn] |
| P04264 | 65998.9 | 1 | Tubulin beta-2A chain |

TABLE 5

Proteins that were prevalent in the ghosts or conditioned ghosts but were missing from the CDLs

| Uniport Accession Number | MW | Prevalent in ghosts | Prevalent in conditioned ghosts | Protein name |
| --- | --- | --- | --- | --- |
| P78527 | 468786.9 | + | + | Actin-related protein 2/3 complex subunit 1B |
| Q99715 | 332939.7 | + | + | rRNA 2'-O-methyltransferase fibrillarin |
| Q14573 | 303910.4 | + | + | NADH dehydrogenase [ubiquinone] 1 alpha subcomplex subunit 8 |
| P24821 | 240697.7 | + | + | E3 ubiquitin-protein ligase MARCH5 |
| P35580 | 228856.9 | + | + | Acyl carrier protein |
| P07942 | 197935.7 | + | + | Fibrillin-1 |
| P55268 | 195853.3 | + | + | Extracellular sulfatase Sulf-1 |
| Q8WWI1 | 192589.5 | + | + | Protein kinase C alpha type |
| P20908 | 183446.3 | + | + | Cytosol aminopeptidase |
| P11047 | 177487.9 | + | + | Beta-galactosidase |
| Q6YHK3 | 161586.8 | + | + | Histone H3.1t |
| Q7L576 | 145088.6 | + | + | GDP-fucose protein O-fucosyltransferase 1 |
| Q08211 | 140868.9 | + | + | Protein S100-A6 |
| P23634 | 137832.9 | + | + | Protein tyrosine phosphatase-like protein PTPLAD1 |
| Q12768 | 134200.9 | + | + | 39S ribosomal protein L43 |
| P00533 | 134190.2 | + | + | Radixin |
| O43795 | 131901.9 | + | + | Putative ribosomal RNA methyltransferase NOP2 |
| Q9BSJ8 | 122780.1 | + | + | Trophoblast glycoprotein |
| P26006 | 118680.2 | + | + | Galectin-3 |
| P54707 | 115437.2 | + | + | ATP synthase subunit f |
| Q8N766 | 111689.2 | + | + | Calponin-2 |
| O60313 | 111560.7 | + | + | Tumor necrosis factor receptor superfamily member 10B |
| Q9Y4L1 | 111266.2 | + | + | Probable glutathione peroxidase 8 |
| Q6P179 | 110391.1 | + | + | Hydroxyacyl-coenzyme A dehydrogenase |
| P22413 | 104856.7 | + | + | Medium-chain specific acyl-CoA dehydrogenase |
| Q6ZXV5 | 103941.9 | + | + | SH3 domain-binding glutamic acid-rich-like protein 3 |
| A0FGR8 | 102294.1 | + | + | V-type proton ATPase 116 kDa subunit a isoform 3 |
| P11586 | 101495.6 | + | + | U5 small nuclear ribonucleoprotein 200 kDa helicase |
| Q15063 | 93255.4 | + | + | Transducin beta-like protein 2 |
| Q13488 | 92908.6 | + | + | Extended synaptotagmin-2 |

TABLE 5-continued

Proteins that were prevalent in the ghosts or conditioned ghosts but were missing from the CDLs

| Uniport Accession Number | MW | Prevalent in ghosts | Prevalent in conditioned ghosts | Protein name |
|---|---|---|---|---|
| O95479 | 88836.6 | + | + | Mitochondrial import inner membrane translocase subunit Tim8 A |
| Q9UBV2 | 88698.6 | + | + | Histone H1.2 |
| Q9NR30 | 87290.5 | + | + | Vesicular integral-membrane protein VIP36 |
| Q15436 | 86105.3 | + | + | SRA stem-loop-interacting RNA-binding protein |
| Q99798 | 85372 | + | + | Nuclear pore complex protein Nup205 |
| P08238 | 83212.2 | + | + | DnaJ homolog subfamily B member 1 |
| P13010 | 82652.4 | + | + | HEAT repeat-containing protein 1 |
| Q96TA1 | 82631.1 | + | + | Pyruvate dehydrogenase E1 component subunit alpha |
| Q8IVL6 | 81785.8 | + | + | Pre-mRNA-processing-splicing factor 8 |
| Q9UH99 | 80261.7 | + | + | Collagen alpha-1(XIV) chain |
| Q9BU23 | 79647.6 | + | + | Probable saccharopine dehydrogenase |
| Q96AC1 | 77810.7 | + | + | Nucleoside diphosphate kinase B |
| P21980 | 77279.8 | + | + | Protein DEK |
| Q6NUQ4 | 77101.6 | + | + | Nascent polypeptide-associated complex subunit alpha |
| P17252 | 76714.3 | + | + | LIM domain only protein 7 |
| P23246 | 76101.8 | + | + | NADH dehydrogenase [ubiquinone] iron-sulfur protein 6 |
| Q99805 | 75725.7 | + | + | Peptidyl-tRNA hydrolase 2 |
| O75746 | 74715 | + | + | Deoxyribonuclease-2-alpha |
| P46063 | 73410 | + | + | Alpha-L-iduronidase |
| Q8NBJ5 | 71590.6 | + | + | Cytochrome c oxidase subunit 6C |
| P17066 | 70984.4 | + | + | Signal peptidase complex subunit 2 |
| O43390 | 70899.2 | + | + | 60S ribosomal protein L35 |
| P43155 | 70812.5 | + | + | Adenosine 3'-phospho 5'-phosphosulfate transporter 1 |
| P34931 | 70331.5 | + | + | Proliferation-associated protein 2G4 |
| P54652 | 69978 | + | + | Splicing factor |
| P17844 | 69104.8 | + | + | Ras-related protein Ral-A |
| Q96CM8 | 68080.8 | + | + | 60S ribosomal protein L10-like |
| Q03252 | 67647.6 | + | + | ATP-binding cassette sub-family E member 1 |
| O94826 | 67412.2 | + | + | Actin-related protein 2/3 complex subunit 2 |
| P20700 | 66367.7 | + | + | Cathepsin Z |
| Q5JTV8 | 66208.4 | + | + | Acyl-coenzyme A thioesterase 1 |
| O00567 | 66008.8 | + | + | Signal peptidase complex catalytic subunit SEC11A |
| P23368 | 65402 | + | + | Acetyl-coenzyme A transporter 1 |
| Q10471 | 64691.5 | + | + | 4F2 cell-surface antigen heavy chain |
| Q10472 | 64177.5 | + | + | Tropomyosin beta chain |
| P14866 | 64092.4 | + | + | Coiled-coil domain-containing protein 47 |
| Q14956 | 63882 | + | + | Myb-binding protein 1A |
| P07686 | 63071.3 | + | + | ADP-ribosylation factor 1 |
| O95302 | 63043.6 | + | + | Synaptonemal complex protein SC65 |
| Q969V3 | 62934.7 | + | + | Signal peptidase complex subunit 3 |
| P30038 | 61680.7 | + | + | NADH dehydrogenase [ubiquinone] iron-sulfur protein 2 |
| Q96S52 | 61617.3 | + | + | Ras-related protein Rab-8A |
| Q9HCC0 | 61294.5 | + | + | EH domain-containing protein 2 |
| Q5SSJ5 | 61169.3 | + | + | Rho GTPase-activating protein 1 |
| Q9P0J1 | 61015.7 | + | + | Putative 40S ribosomal protein S26-like 1 |
| Q9H857 | 60679.8 | + | + | Mitochondrial chaperone BCS1 |
| P04062 | 59678.4 | + | + | Calcium-binding mitochondrial carrier protein Aralar2 |
| Q9Y2X3 | 59540.6 | + | + | Ribosome-releasing factor 2 |
| Q7Z4H8 | 58535.3 | + | + | 39S ribosomal protein L46 |
| Q13217 | 57544.3 | + | + | Cytochrome c1 |
| P49257 | 57513.1 | + | + | Transmembrane 9 superfamily member 4 |
| P26599 | 57185.8 | + | + | 60S ribosomal protein L36a |
| P05091 | 56345.7 | + | + | Metaxin-2 |
| Q96A33 | 55838.4 | + | + | Heterogeneous nuclear ribonucleoprotein L |
| Q9UMS4 | 55146.4 | + | + | ES1 protein homolog |
| O60701 | 54989.3 | + | + | Replication protein A 14 kDa subunit |
| O76021 | 54939 | + | + | 60S ribosomal protein L37a |
| P10619 | 54431.2 | + | + | Neuron-specific calcium-binding protein hippocalcin |
| Q96HE7 | 54358.1 | + | + | Translocation protein SEC63 homolog |
| Q15233 | 54197.4 | + | + | Protein transport protein Sec61 subunit beta |
| Q02818 | 53846.4 | + | + | Torsin-1A-interacting protein 2 |
| P22570 | 53803.1 | + | + | NADH dehydrogenase [ubiquinone] iron-sulfur protein 7 |
| Q96N66 | 52730.3 | + | + | Fatty aldehyde dehydrogenase |
| P20073 | 52705.8 | + | + | All-trans-retinol 13 |
| P61619 | 52230.6 | + | + | H/ACA ribonucleoprotein complex subunit 4 |
| Q9Y512 | 51943.4 | + | + | Multidrug resistance-associated protein 1 |
| O43615 | 51323.6 | + | + | Neuroplastin |
| Q07960 | 50404.3 | + | + | Heterochromatin protein 1-binding protein 3 |
| Q13509 | 50400.3 | + | + | Transmembrane emp24 domain-containing protein 3 |
| Q9P2R7 | 50285.3 | + | + | Phosphoglycerate mutase 1 |
| P80303 | 50164.4 | + | + | Putative heterogeneous nuclear ribonucleoprotein A1-like 3 |
| P36551 | 50120.1 | + | + | Isovaleryl-CoA dehydrogenase |

TABLE 5-continued

Proteins that were prevalent in the ghosts or conditioned ghosts but were missing from the CDLs

| Uniport Accession Number | MW | Prevalent in ghosts | Prevalent in conditioned ghosts | Protein name |
| --- | --- | --- | --- | --- |
| P13489 | 49941.2 | + | + | ATP synthase subunit b |
| Q9Y305 | 49869.6 | + | + | Ras-related protein Rab-5A |
| Q9BUF5 | 49825 | + | + | Poly(rC)-binding protein 2 |
| P04350 | 49553.9 | + | + | Actin-related protein 2/3 complex subunit 5 |
| P31943 | 49198.4 | + | + | 60S ribosomal protein L13a |
| P62495 | 49000.2 | + | + | Mitochondrial import inner membrane translocase subunit Tim13 |
| P82675 | 47976.2 | + | + | Beta-actin-like protein 2 |
| P09543 | 47548.7 | + | + | Protein disulfide-isomerase TMX3 |
| P45954 | 47455.3 | + | + | Acid ceramidase |
| Q8NBX0 | 47121.5 | + | + | Lipase maturation factor 2 |
| O60664 | 47018 | + | + | Ras-related C3 botulinum toxin substrate 1 |
| P28300 | 46914.5 | + | + | Golgin subfamily B member 1 |
| P11310 | 46558.6 | + | + | Ectonucleotide pyrophosphatase/phosphodiesterase family member 1 |
| O75718 | 46532 | + | + | Ras-related protein Rab-18 |
| O14979 | 46409 | + | + | High mobility group protein B1 |
| P26440 | 46289.7 | + | + | Coproporphyrinogen-III oxidase |
| P60842 | 46124.6 | + | + | Contactin-associated protein 1 |
| Q58FF3 | 45829.9 | + | + | Protein S100-A16 |
| Q96HD1 | 45408.9 | + | + | Isocitrate dehydrogenase [NAD] subunit beta |
| Q6YN16 | 45365.5 | + | + | CDP-diacylglycerol--inositol 3-phosphatidyltransferase |
| Q8NC51 | 44938.5 | + | + | Follistatin-related protein 1 |
| Q96G23 | 44847.4 | + | + | Ribose-phosphate pyrophosphokinase 1 |
| Q9BTV4 | 44847.3 | + | + | Eukaryotic initiation factor 4A-III |
| P61160 | 44732.3 | + | + | Probable cation-transporting ATPase 13A1 |
| P09110 | 44263.9 | + | + | High mobility group protein HMGI-C |
| P07093 | 43974.3 | + | + | Mesoderm-specific transcript homolog protein |
| Q9H488 | 43927.2 | + | + | Cytoplasmic FMR1-interacting protein 1 |
| O75521 | 43557.4 | + | + | Matrin-3 |
| Q6NVY1 | 43454.4 | + | + | Polypeptide N-acetylgalactosaminyltransferase 1 |
| P17302 | 42980.9 | + | + | 39S ribosomal protein L1 |
| Q13336 | 42499.8 | + | + | Dolichol-phosphate mannosyltransferase |
| Q16795 | 42482.6 | + | + | Peptidyl-prolyl cis-trans isomerase C |
| P35613 | 42174.1 | + | + | Gamma-glutamyl hydrolase |
| P29992 | 42096.6 | + | + | V-type proton ATPase 16 kDa proteolipid subunit |
| Q9BYX7 | 41988.9 | + | + | Ribosome biogenesis regulatory protein homolog |
| Q562R1 | 41976 | + | + | 28S ribosomal protein S5 |
| Q9BRK5 | 41780.5 | + | + | Lanosterol synthase |
| P30533 | 41440.9 | + | + | Glyoxylate reductase/hydroxypyruvate reductase |
| P82650 | 41254.4 | + | + | Transforming growth factor-beta-induced protein ig-h3 |
| Q15050 | 41168.2 | + | + | Beta-actin-like protein 3 |
| Q12907 | 40203.1 | + | + | Nucleolar RNA helicase 2 |
| O75367 | 39592.5 | + | + | CAAX prenyl protease 1 homolog |
| Q9NYL9 | 39570.3 | + | + | RNA-binding protein FUS |
| P09972 | 39431.3 | + | + | ADP-ribosylation factor-like protein 6-interacting protein 1 |
| Q5EB52 | 38805.5 | + | + | Glia-derived nexin |
| Q15366 | 38555.6 | + | + | Tubulin beta-6 chain |
| Q9H0U3 | 38011.4 | + | + | Magnesium transporter protein 1 |
| O15121 | 37841.1 | + | + | 60S ribosomal protein L6 |
| Q9UDY4 | 37783.2 | + | + | Peptidyl-prolyl cis-trans isomerase FKBP3 |
| P62136 | 37487.8 | + | + | Up-regulated during skeletal muscle growth protein 5 |
| Q14257 | 36853.7 | + | + | Thioredoxin-related transmembrane protein 1 |
| P05198 | 36089.4 | + | + | 28S ribosomal protein S31 |
| Q9NZ01 | 36010.8 | + | + | High mobility group protein HMG-I/HMG-Y |
| P27695 | 35532.2 | + | + | Antigen peptide transporter 1 |
| P08574 | 35367 | + | + | DnaJ homolog subfamily C member 3 |
| P31937 | 35305.8 | + | + | Peroxisomal acyl-coenzyme A oxidase 1 |
| Q08257 | 35184.6 | + | + | Chloride intracellular channel protein 1 |
| Q15006 | 34811.4 | + | + | N-acetylglucosamine-6-sulfatase |
| P09486 | 34609.7 | + | + | Probable transcription factor PML |
| O15144 | 34311.5 | + | + | Mitochondrial import receptor subunit TOM70 |
| Q16836 | 34255.9 | + | + | Endoplasmic reticulum aminopeptidase 2 |
| Q9UHQ9 | 34073.2 | + | + | LDLR chaperone MESD |
| P53007 | 33991 | + | + | Acyl-coenzyme A thioesterase 13 |
| Q9UBR2 | 33846.2 | + | + | Lamin-B1 |
| Q8NBJ7 | 33835.8 | + | + | 116 kDa U5 small nuclear ribonucleoprotein component |
| P62995 | 33645.6 | + | + | Proteolipid protein 2 |
| Q9BPW8 | 33288.9 | + | + | Collagen triple helix repeat-containing protein 1 |
| P07951 | 32830.6 | + | + | Isocitrate dehydrogenase [NAD] subunit gamma |
| P42126 | 32795.2 | + | + | RNA-binding Raly-like protein |
| Q02878 | 32707.6 | + | + | Sphingolipid delta(4)-desaturase DES1 |
| Q86SE5 | 32310.6 | + | + | 3 |

TABLE 5-continued

Proteins that were prevalent in the ghosts or conditioned ghosts but were missing from the CDLs

| Uniport Accession Number | MW | Prevalent in ghosts | Prevalent in conditioned ghosts | Protein name |
|---|---|---|---|---|
| Q9Y639 | 31271.9 | + | + | Mitochondrial import inner membrane translocase subunit TIM44 |
| P15559 | 30848 | + | + | Mammalian ependymin-related protein 1 |
| O75431 | 29744.1 | + | + | Aldehyde dehydrogenase |
| O60762 | 29615.8 | + | + | Urea transporter 1 |
| P22090 | 29437 | + | + | Retinol dehydrogenase 11 |
| P62258 | 29155.4 | + | + | T-complex protein 1 subunit delta |
| P24539 | 28890.3 | + | + | Ribonuclease inhibitor |
| P18669 | 28785.9 | + | + | Splicing factor |
| P67936 | 28504.5 | + | + | 60S ribosomal protein L28 |
| Q9UFN0 | 28448.5 | + | + | Calpain small subunit 1 |
| Q9UHQ4 | 28302.2 | + | + | Histone H1.1 |
| P30042 | 28152.7 | + | + | Pre-mRNA-processing factor 19 |
| P57088 | 27959.8 | + | + | NADH dehydrogenase [ubiquinone] iron-sulfur protein 5 |
| Q9P0L0 | 27875.2 | + | + | OCIA domain-containing protein 2 |
| Q07955 | 27727.8 | + | + | Histone H1.0 |
| P63104 | 27727.7 | + | + | Glycylpeptide N-tetradecanoyltransferase 1 |
| Q9NR28 | 27113.7 | + | + | Putative 60S ribosomal protein L13a-like MGC87657 |
| P33316 | 26689.7 | + | + | Major facilitator superfamily domain-containing protein 10 |
| O75352 | 26620.5 | + | + | Transmembrane emp24 domain-containing protein 1 |
| P54819 | 26460.8 | + | + | Cystatin-B |
| P17931 | 26136.1 | + | + | Integrin alpha-3 |
| P60033 | 25792.1 | + | + | Signal peptidase complex subunit 1 |
| Q9UM22 | 25420.6 | + | + | NAD(P)H dehydrogenase [quinone] 1 |
| Q13445 | 25189.7 | + | + | Mannose-P-dolichol utilization defect 1 protein |
| Q00688 | 25161.3 | + | + | DnaJ homolog subfamily B member 4 |
| Q15005 | 24986.7 | + | + | Heat shock 70 kDa protein 6 |
| P09429 | 24878.2 | + | + | Heterogeneous nuclear ribonucleoprotein D-like |
| P62906 | 24815.5 | + | + | Protein Mpv17 |
| Q9Y3Q3 | 24761.3 | + | + | Tubulin beta-3 chain |
| P27635 | 24587.9 | + | + | Anoctamin-10 |
| Q96L21 | 24502.7 | + | + | Acyl-CoA synthetase family member 2 |
| P62826 | 24407.6 | + | + | Heat shock protein beta-1 |
| B2RPK0 | 24222.8 | + | + | Peptidyl-prolyl cis-trans isomerase FKBP7 |
| O43402 | 23757.7 | + | + | Thioredoxin reductase 2 |
| P20339 | 23643.8 | + | + | Acyl-coenzyme A thioesterase 9 |
| P40429 | 23562.4 | + | + | Heterogeneous nuclear ribonucleoprotein H |
| P11233 | 23552 | + | + | Probable ATP-dependent RNA helicase DDX5 |
| O14735 | 23523.1 | + | + | Hydroxysteroid dehydrogenase-like protein 2 |
| Q8N983 | 23416.2 | + | + | WASH complex subunit strumpellin |
| P45877 | 22748.8 | + | + | NADH dehydrogenase [ubiquinone] 1 alpha subcomplex subunit 9 |
| P46781 | 22577.6 | + | + | Nucleosome assembly protein 1-like 1 |
| P84074 | 22413 | + | + | Lysosomal protective protein |
| Q96AB3 | 22322.8 | + | + | Beta-hexosaminidase subunit alpha |
| O43399 | 22224.3 | + | + | Serum albumin |
| Q02539 | 21828.9 | + | + | B-cell receptor-associated protein 29 |
| O75915 | 21600.4 | + | + | Mitochondrial import inner membrane translocase subunit TIM50 |
| Q9H061 | 21513.5 | + | + | NADH dehydrogenase [ubiquinone] flavoprotein 2 |
| P16403 | 21351.8 | + | + | Protein sel-1 homolog 1 |
| P84077 | 20683.7 | + | + | Beta-hexosaminidase subunit beta |
| P67812 | 20612.1 | + | + | Nucleolar protein 56 |
| P18085 | 20497.7 | + | + | Sterol-4-alpha-carboxylate 3-dehydrogenase |
| P24844 | 19814.5 | + | + | WASH complex subunit 7 |
| O60831 | 19245.5 | + | + | Glycine cleavage system H protein |
| P46778 | 18553.1 | + | + | Putative hexokinase HKDC1 |
| P62280 | 18419 | + | + | SWI/SNF complex subunit SMARCC2 |
| P62277 | 17211.7 | + | + | 39S ribosomal protein L38 |
| Q9BX68 | 17151.2 | + | + | Ganglioside GM2 activator |
| P15531 | 17137.7 | + | + | Oligosaccharyltransferase complex subunit OSTC |
| P62841 | 17029.2 | + | + | Small nuclear ribonucleoprotein-associated proteins B and B' |
| P63241 | 16821.4 | + | + | Regulator of chromosome condensation |
| Q9NRP0 | 16817.8 | + | + | Nucleoside diphosphate kinase A |
| Q86SX6 | 16617.5 | + | + | 60S ribosomal protein L34 |
| O15511 | 16310.3 | + | + | Tubulin beta-4 chain |
| P46779 | 15737.7 | + | + | Tropomyosin alpha-4 chain |
| P26885 | 15639.3 | + | + | Receptor expression-enhancing protein 5 |
| O60361 | 15519 | + | + | Putative pre-mRNA-splicing factor ATP-dependent RNA helicase DHX15 |
| Q9NS69 | 15511.8 | + | + | Four and a half LIM domains protein 2 |

TABLE 5-continued

Proteins that were prevalent in the ghosts or conditioned ghosts but were missing from the CDLs

| Uniport Accession Number | MW | Prevalent in ghosts | Prevalent in conditioned ghosts | Protein name |
|---|---|---|---|---|
| Q9Y3E0 | 15415.4 | + | + | ATP-dependent RNA helicase DHX29 |
| P69905 | 15247.9 | + | + | Leucyl-cystinyl aminopeptidase |
| P42766 | 14542.6 | + | + | Heterogeneous nuclear ribonucleoprotein R |
| P55769 | 14164.6 | + | + | Histidyl-tRNA synthetase |
| P04908 | 14127 | + | + | Small nuclear ribonucleoprotein Sm D3 |
| P61769 | 13705.9 | + | + | Prostacyclin synthase |
| Q5JNZ5 | 12994 | + | + | [Pyruvate dehydrogenase [acetyl-transferring]]-phosphatase 1 |
| Q9GZT3 | 12341.4 | + | + | Protein transport protein Sec23A |
| P84090 | 12251 | + | + | Abhydrolase domain-containing protein 10 |
| Q96FQ6 | 11794 | + | + | Putative endoplasmin-like protein |
| P99999 | 11741.1 | + | + | 60S acidic ribosomal protein P1 |
| P17096 | 11669.2 | + | + | Trans-2 |
| O60220 | 10991.3 | + | + | GDH/6PGL endoplasmic bifunctional protein |
| P56134 | 10910.7 | + | + | Potassium-transporting ATPase alpha chain 2 |
| Q9Y5L4 | 10493 | + | + | Eukaryotic peptide chain release factor subunit 1 |
| Q9H299 | 10431.3 | + | + | Transmembrane and TPR repeat-containing protein 3 |
| P61513 | 10268.5 | + | + | Ribosomal L1 domain-containing protein 1 |
| O75531 | 10052 | + | + | Regulator of microtubule dynamics protein 1 |
| P60468 | 9968.1 | + | + | Adenylate kinase 2 |
| P62979 | 9411.9 | + | + | Alpha-2-macroglobulin |
| P63173 | 8212.7 | + | + | 72 kDa type IV collagenase |
| P04732 | 6009.2 | + | + | SUN domain-containing protein 1 |
| P35555 | 312082 | + | − | Laminin subunit beta-1 |
| Q05707 | 193393 | + | − | SUN domain-containing protein 2 |
| Q7Z478 | 155138.3 | + | − | Vesicle transport protein GOT1B |
| Q9HD20 | 132869.9 | + | − | Actin-related protein 2 |
| Q9UIQ6 | 117274.2 | + | − | Hemoglobin subunit alpha |
| Q9UGP8 | 87941.5 | + | − | ERO1-like protein alpha |
| Q9UJS0 | 74128.8 | + | − | Glucosylceramidase |
| P51970 | 20092.1 | + | − | Inositol 1 |
| P84103 | 19317.9 | + | − | Malignant T cell-amplified sequence 1 |
| Q9Y6H1 | 15502.7 | + | − | U1 small nuclear ribonucleoprotein C |
| Q9NPJ3 | 14950.9 | + | − | Tricarboxylate transport protein |
| P35244 | 13559.9 | + | − | UDP-glucose 6-dehydrogenase |
| O43920 | 12509.4 | + | − | Transmembrane protein 33 |
| Q6NVV1 | 12126.9 | + | − | Diablo homolog |
| P04080 | 11132.6 | + | − | Non-POU domain-containing octamer-binding protein |
| O43678 | 10914.8 | + | − | Ankycorbin |
| P09669 | 8775.7 | + | − | Procollagen galactosyltransferase 1 |
| Q15738 | NA | − | + | ADP-ribosylation factor 4 |
| P17900 | NA | − | + | Histidine triad nucleotide-binding protein 2 |
| P46087 | NA | − | + | Myosin-Ib |
| O00299 | NA | − | + | Quinone oxidoreductase |
| P39210 | NA | − | + | 60S ribosomal protein L10a |
| Q9P035 | NA | − | + | Plasma membrane calcium-transporting ATPase 4 |
| Q9NUJ1 | NA | − | + | Enhancer of rudimentary homolog |
| O43837 | NA | − | + | Cysteine-rich with EGF-like domain protein 1 |
| Q9Y5S1 | NA | − | + | Ribosome production factor 2 homolog |
| Q16647 | NA | − | + | Beta-2-microglobulin |
| Q96JJ7 | NA | − | + | 2' |
| P23434 | NA | − | + | PRA1 family protein 2 |
| P0C7M2 | NA | − | + | Nucleobindin-2 |
| P15289 | NA | − | + | Serine palmitoyltransferase 1 |
| O75844 | NA | − | + | Core histone macro-H2A.1 |
| P09234 | NA | − | + | Coiled-coil-helix-coiled-coil-helix domain-containing protein 2 |
| P08253 | NA | − | + | 60S ribosomal protein L38 |
| P04632 | NA | − | + | Protein NipSnap homolog 3A |
| Q03518 | NA | − | + | DNA-(apurinic or apyrimidinic site) lyase |
| Q8NFQ8 | NA | − | + | Nucleobindin-1 |
| P07305 | NA | − | + | Splicing factor |
| Q15029 | NA | − | + | Sulfatase-modifying factor 2 |
| O75643 | NA | − | + | C-1-tetrahydrofolate synthase |
| Q9Y276 | NA | − | + | 5'-nucleotidase domain-containing protein 2 |
| Q9BYD6 | NA | − | + | Gap junction alpha-1 protein |
| Q8IWU6 | NA | − | + | Laminin subunit beta-2 |
| Q9UBQ7 | NA | − | + | Alpha-2-macroglobulin receptor-associated protein |
| P61221 | NA | − | + | Lamin-B2 |
| P63027 | NA | − | + | Periostin |
| Q9Y4P3 | NA | − | + | Phosphatidylethanolamine-binding protein 1 |
| P30419 | NA | − | + | 14-3-3 protein zeta/delta |
| P50991 | NA | − | + | 14-3-3 protein epsilon |

TABLE 5-continued

Proteins that were prevalent in the ghosts or conditioned ghosts but were missing from the CDLs

| Uniport Accession Number | MW | Prevalent in ghosts | Prevalent in conditioned ghosts | Protein name |
|---|---|---|---|---|
| O94901 | NA | − | + | Metallothionein-1E |
| Q9H7Z7 | NA | − | + | Procollagen C-endopeptidase enhancer 1 |
| P22087 | NA | − | + | Collagen alpha-1(XII) chain |
| P28288 | NA | − | + | 4-trimethylaminobutyraldehyde dehydrogenase |
| Q13505 | NA | − | + | Collagen alpha-1(VIII) chain |
| Q9Y3E5 | NA | − | + | Transmembrane 9 superfamily member 2 |
| P27449 | NA | − | + | Guanine nucleotide-binding protein subunit alpha-11 |
| Q13510 | NA | − | + | Short/branched chain specific acyl-CoA dehydrogenase |
| P62318 | NA | − | + | Histone H2A type 1-B/E |
| O00115 | NA | − | + | Calcium-binding mitochondrial carrier protein Aralar1 |
| P33527 | NA | − | + | Sorting and assembly machinery component 50 homolog |
| Q8NE86 | NA | − | + | Dynactin subunit 2 |
| O60832 | NA | − | + | Protein transport protein Sec61 subunit alpha isoform 1 |
| Q15582 | NA | − | + | 28S ribosomal protein S22 |
| Q13740 | NA | − | + | Inorganic pyrophosphatase 2 |
| Q9NVP1 | NA | − | + | 15 kDa selenoprotein |
| P22392 | NA | − | + | Fermitin family homolog 2 |
| P43243 | NA | − | + | Peroxisomal 3 |
| P38919 | NA | − | + | Transmembrane protein 43 |
| Q04941 | NA | − | + | Transformer-2 protein homolog beta |
| P05386 | NA | − | + | Cytochrome c |
| Q8NHP8 | NA | − | + | 40S ribosomal protein S11 |
| Q8TAQ2 | NA | − | + | Valacyclovir hydrolase |
| O15145 | NA | − | + | Protein LYRIC |
| Q86TX2 | NA | − | + | Torsin-1A-interacting protein 1 |
| Q16629 | NA | − | + | Alpha-centractin |
| P35637 | NA | − | + | Tropomodulin-3 |
| Q9NX47 | NA | − | + | Cartilage-associated protein |
| Q9NP72 | NA | − | + | Tenascin |
| Q9NZN4 | NA | − | + | Methylcrotonoyl-CoA carboxylase beta chain |
| P51648 | NA | − | + | Lysophospholipid acyltransferase 7 |
| O15143 | NA | − | + | DNA-dependent protein kinase catalytic subunit |
| Q92820 | NA | − | + | Basigin |
| Q9Y6A9 | NA | − | + | CD81 antigen |
| P29590 | NA | − | + | SPARC |
| Q6P2Q9 | NA | − | + | Prolyl 3-hydroxylase 3 |
| Q13641 | NA | − | + | 60S ribosomal protein L21 |
| Q2TB90 | NA | − | + | Extended synaptotagmin-1 |
| Q14789 | NA | − | + | Protein-lysine 6-oxidase |
| P15586 | NA | − | + | Tetratricopeptide repeat protein 35 |
| O75694 | NA | − | + | Myosin light chain 1/3 |
| Q56VL3 | NA | − | + | Vesicle-associated membrane protein-associated protein A |
| P61006 | NA | − | + | GPI transamidase component PIG-S |
| P49207 | NA | − | + | Glutaredoxin-related protein 5 |
| P14678 | NA | − | + | 40S ribosomal protein S15 |
| Q96IX5 | NA | − | + | Serine/threonine-protein phosphatase PP1-alpha catalytic subunit |
| O75380 | NA | − | + | Splicing factor |
| Q969S9 | NA | − | + | Nucleolar protein 58 |
| P52926 | NA | − | + | 3-ketoacyl-CoA thiolase |
| Q9H2W6 | NA | − | + | KDEL motif-containing protein 2 |
| Q08170 | NA | − | + | Heat shock-related 70 kDa protein 2 |
| O14763 | NA | − | + | Dynamin-like 120 kDa protein |
| Q15067 | NA | − | + | 3-hydroxyisobutyrate dehydrogenase |
| Q2M389 | NA | − | + | Myosin regulatory light polypeptide 9 |
| Q3ZCQ8 | NA | − | + | PRA1 family protein 3 |
| Q9BRR6 | NA | − | + | 2-oxoisovalerate dehydrogenase subunit alpha |
| P78357 | NA | − | + | Eukaryotic initiation factor 4A-I |
| P19404 | NA | − | + | Transmembrane protein 126A |
| P35659 | NA | − | + | Protein-glutamine gamma-glutamyltransferase 2 |
| P16278 | NA | − | + | Laminin subunit gamma-1 |
| Q9P0K7 | NA | − | + | NADH dehydrogenase [ubiquinone] 1 alpha subcomplex subunit 2 |
| P18754 | NA | − | + | Eukaryotic translation initiation factor 5A-1 |
| P62273 | NA | − | + | Glutathione S-transferase P |
| Q14728 | NA | − | + | Deoxyuridine 5'-triphosphate nucleotidohydrolase |
| O75251 | NA | − | + | Reticulocalbin-2 |
| Q9H3N1 | NA | − | + | NADPH:adrenodoxin oxidoreductase |
| P06703 | NA | − | + | ATP-dependent RNA helicase A |
| O96005 | NA | − | + | 7-dehydrocholesterol reductase |
| P28838 | NA | − | + | Collagen alpha-1(V) chain |
| P83881 | NA | − | + | Polypyrimidine tract-binding protein 1 |
| O43143 | NA | − | + | Putative nucleoside diphosphate kinase |

TABLE 5-continued

Proteins that were prevalent in the ghosts or conditioned ghosts but were missing from the CDLs

| Uniport Accession Number | MW | Prevalent in ghosts | Prevalent in conditioned ghosts | Protein name |
|---|---|---|---|---|
| O00400 | NA | − | + | NAD-dependent malic enzyme |
| Q8TED1 | NA | − | + | Hypoxia up-regulated protein 1 |
| Q9H583 | NA | − | + | X-ray repair cross-complementing protein 5 |
| Q16695 | NA | − | + | CD109 antigen |
| Q96DB5 | NA | − | + | Barrier-to-autointegration factor |
| Q9NW15 | NA | − | + | 60S ribosomal protein L10 |
| P01023 | NA | − | + | 40S ribosomal protein S27a |
| Q92544 | NA | − | + | Protein ERGIC-53 |
| Q9BQG0 | NA | − | + | Transmembrane glycoprotein NMB |
| P48449 | NA | − | + | Fructose-bisphosphate aldolase C |
| P06865 | NA | − | + | 45 kDa calcium-binding protein |
| O14561 | NA | − | + | Isochorismatase domain-containing protein 2 |
| Q15041 | NA | − | + | Aconitate hydratase |
| Q92621 | NA | − | + | Myosin-10 |

TABLE 6

Proteins that were prevalent only on the conditioned ghosts and CDLs

| Uniport Accession Number | MW | Ratio of expression: conditioned CDLs/ conditioned ghost | Protein name |
|---|---|---|---|
| Q15717 | NA | 100% | Endoplasmic reticulum lectin 1 |
| P14136 | NA | 100% | Signal recognition particle receptor subunit alpha |
| Q32P51 | NA | 17% | Long-chain-fatty-acid--CoA ligase 3 |
| Q9NVA2 | NA | 16% | Cation-independent mannose-6-phosphate receptor |
| O75131 | NA | 11% | Granulins |
| Q96DZ1 | NA | 10% | Heterogeneous nuclear ribonucleoprotein K |
| P01889 | NA | 9% | DnaJ homolog subfamily C member 10 |
| Q16270 | NA | 9% | Copine-3 |
| P61978 | NA | 7% | Flotillin-1 |
| P21912 | NA | 6% | Metalloproteinase inhibitor 3 |
| P28799 | NA | 6% | Glial fibrillary acidic protein |
| Q8IXB1 | NA | 6% | Translational activator GCN1 |
| Q5KU26 | NA | 5% | Heterogeneous nuclear ribonucleoprotein A1-like 2 |
| O75955 | NA | 4% | Protein FAM98A |
| P35625 | NA | 4% | Septin-11 |
| Q92616 | NA | 4% | Succinate dehydrogenase [ubiquinone] iron-sulfur subunit |
| O95573 | NA | 3% | Collectin-12 |
| Q8NCA5 | NA | 3% | Insulin-like growth factor-binding protein 7 |
| P11717 | NA | 2% | HLA class I histocompatibility antigen |

TABLE 7

Proteins that were prevalent in ghosts, conditioned ghosts and conditioned CDLs but were missing from unconditioned CDLs.

| Uniport Accession Number | MW | Ratio of expression | | Protein name |
| | | Cond Ghosts/Ghosts | Cond. CDLs/Cond. Ghosts | |
|---|---|---|---|---|
| Q53EP0 | 132803.2 | 302% | 2% | Calumenin |
| P52272 | 77464.3 | 262% | 2% | Nucleophosmin |
| P12956 | 69799.2 | 248% | 1% | Cytochrome c oxidase subunit 2 |
| O60716 | 108103.3 | 220% | 4% | Glutaminase kidney isoform |
| P05121 | 45031.1 | 218% | 5% | Integrin beta-5 |
| P18621 | 21383.3 | 218% | 13% | Plasma membrane calcium-transporting ATPase 1 |
| Q9H845 | 68716.8 | 209% | 7% | Nucleolin |
| Q14103 | 38410.3 | 198% | 0% | 60S acidic ribosomal protein P0 |
| P61916 | 16559.5 | 195% | 2% | Atlastin-3 |
| Q02978 | 34039.9 | 193% | 3% | NADH dehydrogenase [ubiquinone] iron-sulfur protein 8 |
| Q969X5 | 32571.5 | 186% | 8% | Neutral alpha-glucosidase AB |
| P07858 | 37796.8 | 179% | 2% | Cytochrome c oxidase subunit 4 isoform 1 |
| O95831 | 66859 | 176% | 4% | Complement component 1 Q subcomponent-binding protein |

TABLE 7-continued

Proteins that were prevalent in ghosts, conditioned ghosts and conditioned CDLs but were missing from unconditioned CDLs.

| Uniport Accession Number | MW | Ratio of expression | | Protein name |
|---|---|---|---|---|
| | | Cond Ghosts/Ghosts | Cond. CDLs/Cond. Ghosts | |
| P51148 | 23467.8 | 161% | 6% | 3-hydroxyacyl-CoA dehydrogenase type-2 |
| Q9H0U4 | 22157.2 | 161% | 1% | AP-2 complex subunit alpha-1 |
| O75390 | 51679.6 | 157% | 3% | Adenylyl cyclase-associated protein 1 |
| Q8TCJ2 | 93613.8 | 155% | 1% | Collagen alpha-1(III) chain |
| P21964 | 30017.6 | 148% | 0% | Mitochondrial carrier homolog 2 |
| O43852 | 37083.6 | 143% | 2% | Fibronectin type III domain-containing protein 3B |
| O95782 | 107477.9 | 142% | 5% | Ras-related protein Rab-1B |
| P50416 | 88310.8 | 142% | 2% | Alpha-actinin-1 |
| Q9NYU2 | 177077.4 | 140% | 1% | Hydroxymethylglutaryl-CoA lyase |
| P46977 | 80476.9 | 138% | 3% | 40S ribosomal protein S12 |
| P49821 | 50784.9 | 137% | 5% | Actin-related protein 3 |
| Q12797 | 85809.5 | 135% | 5% | 40S ribosomal protein S20 |
| P46940 | 189132.9 | 133% | 1% | Thy-1 membrane glycoprotein |
| Q9ULV4 | 53215.1 | 131% | 3% | Coronin-1C |
| O00159 | 121648.1 | 129% | 4% | NADH dehydrogenase [ubiquinone] 1 alpha subcomplex subunit 10 |
| P07996 | 129299.2 | 129% | 2% | Mitochondrial-processing peptidase subunit beta |
| O14773 | 61209.7 | 129% | 6% | Mesencephalic astrocyte-derived neurotrophic factor |
| P10620 | 17587.2 | 128% | 3% | 60S ribosomal protein L8 |
| Q9NSE4 | 113719.1 | 121% | 4% | Peptidyl-prolyl cis-trans isomerase A |
| O00469 | 84631.8 | 120% | 2% | 39S ribosomal protein L49 |
| P20340 | 23577.9 | 100% | 100% | 60S ribosomal protein L3 |
| P80723 | 22680 | 100% | 33% | Endoplasmic reticulum resident protein 44 |
| Q96AQ6 | 80594.2 | 100% | 27% | 40S ribosomal protein S7 |
| P08962 | 25619.1 | 100% | 25% | Prolyl 4-hydroxylase subunit alpha-2 |
| P50281 | 65842 | 100% | 25% | Transmembrane emp24 domain-containing protein 4 |
| P62988 | 8559.6 | 100% | 23% | Electron transfer flavoprotein subunit alpha |
| P21291 | 20553.8 | 100% | 21% | Protein S100-A10 |
| P62879 | 37307.1 | 100% | 21% | 40S ribosomal protein S23 |
| Q92499 | 82379.9 | 100% | 15% | Myosin-11 |
| P05388 | 34251.8 | 100% | 14% | Heterogeneous nuclear ribonucleoprotein D0 |
| O96000 | 20763.2 | 100% | 12% | Catenin beta-1 |
| P23528 | 18490.7 | 100% | 12% | Seprase |
| P15313 | 56797 | 100% | 12% | Translocation protein SEC62 |
| Q9UBS4 | 40488.7 | 100% | 12% | Mitochondrial 2-oxoglutarate/malate carrier protein |
| P62917 | 28007.3 | 100% | 12% | Microsomal glutathione S-transferase 1 |
| P00403 | 25548.2 | 100% | 12% | X-ray repair cross-complementing protein 6 |
| P17813 | 70533.2 | 100% | 11% | Talin-1 |
| P61353 | 15787.8 | 100% | 11% | Mannosyl-oligosaccharide glucosidase |
| Q00341 | 141368 | 100% | 11% | Neutral cholesterol ester hydrolase 1 |
| P0C7P4 | 30796.1 | 100% | 11% | Probable ATP-dependent RNA helicase DDX17 |
| P49368 | 60495.4 | 100% | 11% | Cytochrome b-c1 complex subunit 7 |
| Q9NQC3 | 129851.2 | 100% | 10% | 40S ribosomal protein S15a |
| Q9NX63 | 26136.2 | 100% | 10% | Interleukin enhancer-binding factor 3 |
| P84098 | 23451.3 | 100% | 10% | Protein ETHE1 |
| Q12906 | 95279.2 | 100% | 10% | Coiled-coil-helix-coiled-coil-helix domain-containing protein 3 |
| P11166 | 54048.7 | 100% | 9% | Estradiol 17-beta-dehydrogenase 12 |
| P06748 | 32554.9 | 100% | 9% | Heterogeneous nuclear ribonucleoprotein M |
| Q99584 | 11464.1 | 100% | 9% | Mitochondrial import receptor subunit TOM40 homolog |
| P14927 | 13522 | 100% | 8% | T-complex protein 1 subunit gamma |
| Q9UBI6 | 8001.2 | 100% | 8% | Pyruvate dehydrogenase E1 component subunit alpha |
| P83731 | 17767.9 | 100% | 8% | Protein canopy homolog 2 |
| Q02218 | 115861.5 | 100% | 8% | Spectrin alpha chain |
| P61026 | 22526.6 | 100% | 7% | Filamin-A |
| O95299 | 40725 | 100% | 7% | Myosin-Ic |
| P22626 | 37406.7 | 100% | 7% | Ras-related protein Rap-1A |
| Q9UBG0 | 166548.2 | 100% | 7% | Succinyl-CoA ligase [GDP-forming] subunit beta |
| P07099 | 52915 | 100% | 7% | RNA-binding protein Raly |
| O95182 | 12543.6 | 100% | 7% | Collagen alpha-2(VI) chain |
| P04216 | 17923.4 | 100% | 7% | Ras GTPase-activating-like protein IQGAP1 |
| P62266 | 15797.7 | 100% | 7% | Guanine nucleotide-binding protein G(I)/G(S)/G(T) subunit beta-2 |
| P35221 | 100008.6 | 100% | 7% | V-type proton ATPase subunit B |
| Q13405 | 19186 | 100% | 7% | Procollagen-lysine |
| P18859 | 12579.6 | 100% | 7% | 60S ribosomal protein L32 |
| P25398 | 14505.5 | 100% | 7% | Dolichyl-diphosphooligosaccharide--protein glycosyltransferase subunit STT3A |
| O00571 | 73198.1 | 100% | 7% | Alpha-soluble NSF attachment protein |
| P00367 | 61359.3 | 100% | 7% | ATPase family AAA domain-containing protein 3A |
| P62081 | 22113.3 | 100% | 6% | Pre-B-cell leukemia transcription factor-interacting protein 1 |
| Q15293 | 38866.2 | 100% | 6% | Delta-1-pyrroline-5-carboxylate synthase |
| P21333 | 280561.4 | 100% | 6% | Ras-related protein Rab-10 |

TABLE 7-continued

Proteins that were prevalent in ghosts, conditioned ghosts and conditioned CDLs but were missing from unconditioned CDLs.

| Uniport Accession Number | MW | Ratio of expression | | Protein name |
|---|---|---|---|---|
| | | Cond Ghosts/Ghosts | Cond. CDLs/Cond. Ghosts | |
| P54920 | 33211.3 | 100% | 6% | ATP-dependent RNA helicase DDX3X |
| P62249 | 16435 | 100% | 6% | DnaJ homolog subfamily B member 11 |
| P62834 | 20973.7 | 100% | 6% | Heterogeneous nuclear ribonucleoproteins A2/B1 |
| O00264 | 21657.8 | 100% | 6% | Thioredoxin domain-containing protein 5 |
| Q16718 | 13450.2 | 100% | 6% | Calmodulin |
| Q9Y3B3 | 25155.6 | 100% | 6% | 40S ribosomal protein S27-like |
| Q01518 | 51822.8 | 100% | 6% | Citrate synthase |
| P35222 | 85442.3 | 100% | 6% | NADH dehydrogenase [ubiquinone] 1 beta subcomplex subunit 10 |
| Q9UKM9 | 32443.6 | 100% | 6% | Epoxide hydrolase 1 |
| P51991 | 39570.5 | 100% | 6% | 60S ribosomal protein L36 |
| P04899 | 40425.1 | 100% | 6% | UPF0027 protein C22orf28 |
| P62244 | 14830 | 100% | 6% | Reticulon-4 |
| P32322 | 33339.6 | 100% | 5% | Sarcoplasmic/endoplasmic reticulum calcium ATPase 1 |
| P52815 | 21334.7 | 100% | 5% | Peptidyl-prolyl cis-trans isomerase FKBP11 |
| Q15019 | 41461.3 | 100% | 5% | Histone H2A type 1-A |
| Q13011 | 35793.4 | 100% | 5% | Gelsolin |
| P00558 | 44586.2 | 100% | 5% | ATP synthase subunit g |
| O75439 | 54331.6 | 100% | 5% | Thrombospondin-1 |
| P43304 | 80801.7 | 100% | 5% | Histone H1.5 |
| P18084 | 87996.2 | 100% | 5% | Plasminogen activator inhibitor 1 |
| Q7Z7H5 | 25926.4 | 100% | 5% | Matrix metalloproteinase-14 |
| Q14554 | 59556.2 | 100% | 5% | Peptidyl-prolyl cis-trans isomerase FKBP10 |
| O60506 | 69559.6 | 100% | 5% | Enoyl-CoA hydratase |
| Q9Y3U8 | 12245.9 | 100% | 5% | Heterogeneous nuclear ribonucleoprotein A3 |
| P62820 | 22663.4 | 100% | 5% | Fumarate hydratase |
| Q13813 | 284362.5 | 100% | 5% | 2-oxoglutarate dehydrogenase |
| Q6P587 | 24826.7 | 100% | 5% | Interleukin enhancer-binding factor 2 |
| O75964 | 11421.2 | 100% | 5% | Phosphoglycerate kinase 1 |
| Q9Y2B0 | 20639.2 | 100% | 4% | 60S ribosomal protein L24 |
| Q12931 | 80059.8 | 100% | 4% | Myeloid-associated differentiation marker |
| P51572 | 27974 | 100% | 4% | Alpha-actinin-4 |
| Q5JRX3 | 117380.3 | 100% | 4% | Ornithine aminotransferase |
| P36776 | 106422.5 | 100% | 4% | UPF0556 protein C19orf10 |
| O95571 | 27855.1 | 100% | 4% | 60S ribosomal protein L19 |
| P61158 | 47341 | 100% | 4% | NADH dehydrogenase [ubiquinone] flavoprotein 1 |
| Q9BS26 | 46941.5 | 100% | 4% | NADH dehydrogenase [ubiquinone] 1 alpha subcomplex subunit 7 |
| P10515 | 68953.3 | 100% | 4% | 40S ribosomal protein S2 |
| Q71UM5 | 9470.9 | 100% | 4% | Transmembrane emp24 domain-containing protein 7 |
| Q12905 | 43035.2 | 100% | 4% | Fumarylacetoacetate hydrolase domain-containing protein 1 |
| P54886 | 87247.7 | 100% | 4% | Reticulocalbin-1 |
| P13073 | 19564.1 | 100% | 4% | Cathepsin B |
| P15880 | 31304.6 | 100% | 4% | Dihydrolipoyllysine-residue acetyltransferase component of pyruvate dehydrogenase complex |
| P60866 | 13364.3 | 100% | 4% | Aspartyl/asparaginyl beta-hydroxylase |
| Q96I99 | 46481.5 | 100% | 3% | Catechol O-methyltransferase |
| O96008 | 37869.2 | 100% | 3% | Protein S100-A13 |
| P61313 | 24131.1 | 100% | 3% | Alpha-aminoadipic semialdehyde dehydrogenase |
| Q6PIU2 | 45778.8 | 100% | 3% | Vigilin |
| Q8NBS9 | 47598.7 | 100% | 3% | Membrane-associated progesterone receptor component 1 |
| Q14165 | 32213.6 | 100% | 3% | Galectin-1 |
| P04181 | 48504.3 | 100% | 3% | Presequence protease |
| Q9NVI7 | 71324.8 | 100% | 3% | Glutamate dehydrogenase 1 |
| Q92896 | 134463.3 | 100% | 3% | Pyruvate dehydrogenase E1 component subunit beta |
| Q99653 | 22442.4 | 100% | 3% | Profilin-1 |
| P54709 | 31492.1 | 100% | 3% | Serine beta-lactamase-like protein LACTB |
| Q92520 | 24664.6 | 100% | 3% | 40S ribosomal protein S17 |
| P53597 | 36226.9 | 100% | 3% | 3-ketoacyl-CoA thiolase |
| P15311 | 69369.8 | 100% | 3% | Myosin light polypeptide 6 |
| P13804 | 35057.6 | 100% | 3% | Ubiquitin |
| O00217 | 23689.6 | 100% | 3% | 40S ribosomal protein S16 |
| Q9UIJ7 | 25549.6 | 100% | 3% | Microsomal glutathione S-transferase 3 |
| P62158 | 16826.8 | 100% | 3% | NADH dehydrogenase [ubiquinone] 1 alpha subcomplex subunit 5 |
| Q969H8 | 18783.3 | 100% | 3% | Lon protease homolog |
| P83111 | 60655.1 | 100% | 3% | Sodium/potassium-transporting ATPase subunit beta-3 |
| Q12884 | 87656.8 | 100% | 3% | Cofilin-1 |
| P07954 | 54602.2 | 100% | 3% | Ras-related protein Rab-1A |
| Q14697 | 106806.8 | 100% | 3% | Endoplasmic reticulum-Golgi intermediate compartment protein 1 |

TABLE 7-continued

Proteins that were prevalent in ghosts, conditioned ghosts and conditioned CDLs but were missing from unconditioned CDLs.

| Uniport Accession Number | MW | Ratio of expression Cond Ghosts/Ghosts | Cond. CDLs/Cond. Ghosts | Protein name |
| --- | --- | --- | --- | --- |
| O14983 | 110181.8 | 100% | 2% | Pyrroline-5-carboxylate reductase 1 |
| Q99714 | 26906.1 | 100% | 2% | Ras-related protein Rab-5C |
| P20020 | 138667.9 | 100% | 2% | 60S ribosomal protein L17 |
| P62910 | 15849.8 | 100% | 2% | ATP synthase-coupling factor 6 |
| P39023 | 46079.8 | 100% | 2% | Ras-related protein Rab-6A |
| Q9NYL4 | 22166.3 | 100% | 2% | 39S ribosomal protein L12 |
| O14880 | 16505.6 | 100% | 2% | GTP:AMP phosphotransferase mitochondrial |
| Q92841 | 72326 | 100% | 2% | Putative cytochrome b-c1 complex subunit Rieske-like protein 1 |
| Q96QV6 | 14224.9 | 100% | 2% | Septin-2 |
| Q9Y224 | 28050.7 | 100% | 2% | Catenin alpha-1 |
| P55809 | 56122 | 100% | 2% | Transmembrane emp24 domain-containing protein 2 |
| Q13724 | 91860.9 | 100% | 1% | 60S ribosomal protein L27 |
| Q6DD88 | 60503.5 | 100% | 1% | Epididymal secretory protein E1 |
| Q96AY3 | 64204.3 | 100% | 1% | Protein disulfide-isomerase A5 |
| Q9Y6C9 | 33308.9 | 100% | 1% | C-type mannose receptor 2 |
| O15460 | 60863.7 | 100% | 1% | CD63 antigen |
| Q53GQ0 | 34302.2 | 100% | 1% | Solute carrier family 2 |
| Q07021 | 31342.6 | 100% | 1% | Apoptosis-inducing factor 1 |
| P60660 | 16919.1 | 100% | 0% | Ezrin |
| P35749 | 227197.9 | 100% | 0% | ATP-dependent RNA helicase DDX1 |
| P08559 | 43267.7 | 100% | 0% | Guanine nucleotide-binding protein G(I)/G(S)/G(O) subunit gamma-12 |
| O15260 | 30373.8 | 100% | 0% | Tropomyosin alpha-1 chain |
| P16401 | 22566.5 | 100% | 0% | Glycerol-3-phosphate dehydrogenase |
| P11177 | 39208.1 | 82% | 4% | Golgi apparatus protein 1 |
| P12110 | 108511.9 | 81% | 3% | Brain acid soluble protein 1 |
| P42765 | 41897.7 | 79% | 2% | Succinyl-CoA ligase [GDP-forming] subunit alpha |
| O94925 | 73414 | 76% | 3% | Catenin delta-1 |
| Q9Y3I0 | 55175 | 72% | 8% | Guanine nucleotide-binding protein G(i) subunit alpha-2 |
| P55145 | 20243.6 | 71% | 2% | Tripeptidyl-peptidase 1 |
| O43707 | 104788.5 | 71% | 4% | B-cell receptor-associated protein 31 |
| P12814 | 102992.7 | 70% | 4% | Carnitine O-palmitoyltransferase 1 |
| P49419 | 58450.2 | 66% | 3% | 60S ribosomal protein L15 |
| P09493 | 32688.7 | 66% | 27% | Surfeit locus protein 4 |
| P35914 | 34337.8 | 62% | 8% | UDP-glucose:glycoprotein glucosyltransferase 1 |
| P37802 | 22377.2 | 61% | 4% | 60S ribosomal protein L23a |
| P07737 | 15044.6 | 57% | 7% | Calcium-binding protein p22 |
| P08708 | 15540.4 | 57% | 5% | Protein FAM3C |
| P30084 | 31367.1 | 57% | 3% | Heterogeneous nuclear ribonucleoprotein Q |
| P62937 | 18000.9 | 54% | 9% | Isoleucyl-tRNA synthetase |
| P19338 | 76568.5 | 50% | 42% | Acyl-CoA dehydrogenase family member 9 |
| P09382 | 14706.2 | 45% | 28% | Malectin |
| P06396 | 85644.3 | 36% | 2% | Delta(3 |
| P02461 | 138479.2 | 35% | 6% | Dolichyl-diphosphooligosaccharide--protein glycosyltransferase subunit STT3B |
| Q9Y490 | 269596.3 | 34% | 5% | Endoglin |
| P62750 | 17684.1 | 24% | 31% | Transgelin-2 |

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

REFERENCE (OTHER REFERENCES ARE CITED THROUGHOUT THE APPLICATION)

1. Petersson, B. The dry mass of the pancreatic B-cells in relation to their content of secretion granules. *The Histochemical Journal* 1, 55-58 (1968).
2. Loewenstein, J. E. & Cohen, A. I. Dry Mass, Lipid Content and Protein Content of the Intact and Zona-Free Mouse Ovum. *J Embryol Exp Morphol* 12, 113-121 (1964).
3. Lapidus, R. G., Tiffany, C. W., Isaacs, J. T. & Slusher, B. S. Prostate-specific membrane antigen (PSMA) enzyme activity is elevated in prostate cancer cells. *Prostate* 45, 350-354 (2000).
4. Hur, E. M. et al. LIME, a novel transmembrane adaptor protein, associates with p56lck and mediates T cell activation. *J Exp Med* 198, 1463-1473 (2003).
5. Lewis, L. A. et al. The Lck SH2 phosphotyrosine binding site is critical for efficient TCR-induced processive tyrosine phosphorylation of the zeta-chain and IL-2 production. *J Immunol* 159, 2292-2300 (1997).
6. Crowther, M., Brown, N. J., Bishop, E. T. & Lewis, C. E. Microenvironmental influence on macrophage regulation of angiogenesis in wounds and malignant tumors. *J Leukoc Biol* 70, 478-490 (2001).
7. Martinez-Palomo, A., G. H. Bourne, J. F. D. & Jeon, K. W. in International Review of Cytology, Vol. Volume 29 29-75 (Academic Press, 1970).
8. Marquez, M. et al. Charge-dependent targeting: results in six tumor cell lines. *Anticancer Res* 24, 1347-1351 (2004).
9. Carter, H. B. & Coffey, D. S. Cell surface charge in predicting metastatic potential of aspirated cells from the Dunning rat prostatic adenocarcinoma model. *J Urol* 140, 173-175 (1988).
10. Bjellqvist, B., Basse, B., Olsen, E. & Celis, J. E. Reference points for comparisons of two-dimensional maps of proteins from different human cell types defined in a pH scale where isoelectric points correlate with polypeptide compositions. *Electrophoresis* 15, 529-539 (1994).
11. Bjellqvist, B. et al. The focusing positions of polypeptides in immobilized pH gradients can be predicted from their amino acid sequences. *Electrophoresis* 14, 1023-1031 (1993).
12. Link, A. J., Hays, L. G., Carmack, E. B. & Yates, J. R., 3rd Identifying the major proteome components of *Haemophilus influenzae* type-strain NCTC 8143. *Electrophoresis* 18, 1314-1334 (1997).
13. Link, A. J., Robison, K. & Church, G. M. Comparing the predicted and observed properties of proteins encoded in the genome of *Escherichia coli* K-12. *Electrophoresis* 18, 1259-1313 (1997).
14. Campbell, R. B. et al. Cationic charge determines the distribution of liposomes between the vascular and extravascular compartments of tumors. *Cancer Res* 62, 6831-6836 (2002).
15. Krasnici, S. et al. Effect of the surface charge of liposomes on their uptake by angiogenic tumor vessels. *Int J Cancer* 105, 561-567 (2003).
16. Croyle, M. A. et al. PEGylation of a vesicular stomatitis virus G pseudotyped lentivirus vector prevents inactivation in serum. *J Virol* 78, 912-921 (2004).
17. Immordino, M. L., Dosio, F. & Cattel, L. Stealth liposomes: review of the basic science, rationale, and clinical applications, existing and potential. *Int J Nanomedicine* 1, 297-315 (2006).
18. Peeters, L., Sanders, N. N., Jones, A., Demeester, J. & De Smedt, S. C. Post-pegylated lipoplexes are promising vehicles for gene delivery in RPE cells. *J Control Release* 121, 208-217 (2007).
19. Rivest, V. et al. Novel liposomal formulation for targeted gene delivery. *Pharm Res* 24, 981-990 (2007).
20. Degli-Esposti, M. A. et al. Cloning and characterization of TRAIL-R3, a novel member of the emerging TRAIL receptor family. *J Exp Med* 186, 1165-1170 (1997).
21. Lee, H. O., Herndon, J. M., Barreiro, R., Griffith, T. S. & Ferguson, T. A. TRAIL: a mechanism of tumor surveillance in an immune privileged site. *J Immunol* 169, 4739-4744 (2002).
22. LeBlanc, H. N. & Ashkenazi, A. Apo2 L/TRAIL and its death and decoy receptors. *Cell Death Differ* 10, 66-75 (2003).
23. Walczak, H. et al. Tumoricidal activity of tumor necrosis factor-related apoptosis-inducing ligand in vivo. *Nat Med* 5, 157-163 (1999).
24. Rieger, J., Naumann, U., Glaser, T., Ashkenazi, A. & Weller, M. APO2 ligand: a novel lethal weapon against malignant glioma? *FEBS Lett* 427, 124-128 (1998).
25. Wu, X., He, Y., Falo, L. D., Jr., Hui, K. M. & Huang, L. Regression of human mammary adenocarcinoma by systemic administration of a recombinant gene encoding the hFlex-TRAIL fusion protein. *Mol Ther* 3, 368-374 (2001).
26. Griffith, T. S., Anderson, R. D., Davidson, B. L., Williams, R. D. & Ratliff, T. L. Adenoviral-mediated transfer of the TNF-related apoptosis-inducing ligand/Apo-2 ligand gene induces tumor cell apoptosis. *J Immunol* 165, 2886-2894 (2000).

What is claimed is:

1. A composition-of matter comprising a liposome composed of a whole cell membrane fraction, wherein the liposome exhibits native membrane symmetry and expression of native markers, said liposome encapsulating or conjugated to a pharmaceutical agent being exogenous to the cell from which said whole cell membrane is obtained and said liposome being devoid of the cytoplasmic content of said cell.

2. The composition-of-matter of claim 1, wherein said cell is a genetically modified cell.

3. The composition-of-matter of claim 1, wherein said liposome is 30-1000 nm in size.

4. The composition-of-matter of claim 1, wherein said liposome further comprises synthetic lipids.

5. The composition-of-matter of claim 1, wherein said liposome is attached to a synthetic polymer at an external surface thereof.

6. A pharmaceutical composition comprising as an active ingredient the composition-of-matter of claim 1 and a pharmaceutically acceptable carrier.

7. The composition-of-matter of claim 1, wherein said cell is genetically modified to express an exogenous protein such that the whole cell membrane fraction comprises the exogenous protein.

8. A composition-of matter comprising a liposome composed of a whole cell membrane fraction of a cell, wherein said liposome exhibits native membrane symmetry and expression of native markers and wherein said liposome is devoid of the cytoplasmic content of said cell.

9. The composition-of-matter of claim 8, wherein said liposome encapsulates or conjugated to a pharmaceutical agent being exogenous to said cell.

10. The composition-of-matter of claim 8, wherein said liposome is attached to a synthetic polymer at an external surface thereof.

11. The composition-of-matter of claim 8, wherein said liposome is 30-1000 nm in size.

12. A pharmaceutical composition comprising as an active ingredient the composition-of-matter of claim 8 and a pharmaceutically acceptable carrier.

13. A method of producing liposomes exhibiting native membrane symmetry and expression of native markers, the method comprising,
    (a) subjecting cells to hypotonic conditions, so as to obtain ruptured cell membranes and/or ghosts; and
    (b) homogenizing said ruptured cell membranes and/or ghosts to thereby produce liposomes, wherein the method is devoid of membrane solubilizaton in the presence of a detergent,
thereby producing the liposomes exhibiting native membrane symmetry and expression of native markers.

14. The method of claim 13, wherein said homogenizing is effected by:

(c) sonicating said ruptured cell membrane and/or ghosts; and optionally
(d) extruding said ruptured membrane and/or ghosts through a matrix of pre-determined porosity.

15. The method of claim 13 further comprising conjugating a synthetic polymer to said liposomes following step (c).

16. A method of encapsulating a pharmaceutical agent in a liposome, the method comprising making the liposomes according to the method of claim 13 and adding the pharmaceutical agent prior to the step of homogenizing.

* * * * *